(12) United States Patent
Schröder

(10) Patent No.: US 11,479,587 B2
(45) Date of Patent: Oct. 25, 2022

(54) CATIONIC INTRINSICALLY DISORDERED ANTIMICROBIAL PEPTIDES

(71) Applicant: Christian-Albrechts-Universität zu Kiel, Kiel (DE)

(72) Inventor: Jens-Michael Schröder, Blumenthal (DE)

(73) Assignee: Christian-Albrechts-Universität zu Kiel, Kiel (DE)

( * ) Notice: Subject to any disclaimer, the term of this patent is extended or adjusted under 35 U.S.C. 154(b) by 0 days.

(21) Appl. No.: 16/462,498

(22) PCT Filed: Nov. 15, 2017

(86) PCT No.: PCT/EP2017/079307
§ 371 (c)(1),
(2) Date: May 20, 2019

(87) PCT Pub. No.: WO2018/091523
PCT Pub. Date: May 24, 2018

(65) Prior Publication Data
US 2020/0115426 A1    Apr. 16, 2020

(30) Foreign Application Priority Data
Nov. 21, 2016    (EP) .................... 16199780

(51) Int. Cl.
*C07K 14/47*    (2006.01)
*A23K 20/147*    (2016.01)
*A61P 31/04*    (2006.01)
*A61K 38/00*    (2006.01)
*A01N 37/46*    (2006.01)
*A61K 8/64*    (2006.01)

(52) U.S. Cl.
CPC .......... *C07K 14/4723* (2013.01); *A01N 37/46* (2013.01); *A23K 20/147* (2016.05); *A61K 8/64* (2013.01); *A61P 31/04* (2018.01); *A61K 38/00* (2013.01)

(58) Field of Classification Search
CPC ... C07K 14/4723; A23K 20/147; A61P 31/04; A61K 38/00
See application file for complete search history.

(56) References Cited

U.S. PATENT DOCUMENTS

| | | | | |
|---|---|---|---|---|
| 5,637,454 A | * | 6/1997 | Harley | G01N 33/56983 435/5 |
| 5,958,684 A | * | 9/1999 | Van Leeuwen | C07K 14/4711 435/6.14 |
| 7,157,419 B2 | * | 1/2007 | Sebti | C07K 7/56 514/8.1 |
| 8,470,976 B2 | * | 6/2013 | Chook | C12N 15/62 530/358 |
| 9,061,059 B2 | * | 6/2015 | Chakraborty | A61P 3/00 |
| 9,404,097 B2 | * | 8/2016 | Pack | C12Y 207/01 |
| 2004/0002457 A1 | * | 1/2004 | Hovanessian | C07K 14/705 514/3.8 |
| 2009/0318366 A1 | * | 12/2009 | Edens | C07K 5/1008 514/1.1 |
| 2011/0218156 A1 | | 9/2011 | Chucholowski et al. | |
| 2013/0018000 A1 | * | 1/2013 | Stout | C07K 14/4713 514/18.8 |
| 2014/0120074 A1 | * | 5/2014 | Miller | A61K 45/06 424/94.3 |
| 2015/0017227 A1 | * | 1/2015 | Kim | A61K 31/05 424/450 |

FOREIGN PATENT DOCUMENTS

| | | | | |
|---|---|---|---|---|
| WO | WO 03/067212 | * | 8/2003 | |
| WO | WO-2004/110341 | | 12/2004 | |
| WO | WO-2007/107587 | | 9/2007 | |
| WO | WO-2011/077133 | | 6/2011 | |
| WO | WO-2011/119484 | | 9/2011 | |
| WO | WO 2013/048222 | * | 4/2013 | ............... C12N 9/12 |
| WO | WO 2015/077342 | * | 5/2015 | ......... A61K 31/7105 |
| WO | WO-2015/118028 | | 8/2015 | |
| WO | WO-2016/172722 | | 10/2016 | |

OTHER PUBLICATIONS

De Smet et al., 2005, Human antimicrobial peptides: defensins, cathelicidins and histatins, Biotechnology Letters, 27: 1337-1347.*
Zhang et al., 2012, Converting Peptides into Drug Leads by Lipidation, Current Medicinal Chemistry, 19: 1602-1618.*
Docherty et al., 1987, Inactivation of Herpes Simplex Virus Types 1 and 2 by Synthetic Histidine Peptides, Antimicrobial Agents and Chemotherapy, 31(10): 1562-1566.*
Guzman et al., 2013, Inhibitory effect of short cationic homopeptides against Gram-positive bacteria, J Pept Sci, 19: 792-800.*
Hyldgaard et al., 2014, The Antimicrobial Mechanism of Action of Epsilon-Poly-L-Lysine, Applied and Environmental Microbiology, 80(24): 7758-7770.*
Van Drongelen et al., 2014, Reduced filaggrin expression is accompanied by increased *Staphylococcus aureus* colonization of epidermal skin models, Clinical & Experimental Allergy, 44: 1515-1524.*
Harding et al., 2013, Filaggrin—revisited, International Journal of Cosmetic Science, 35: 412-423.*
Oh et al., 2014, Antibacterial Activities of Amphiphilic Cyclic Cell-Penetrating peptides against Multidrug-Resistant Pathogens, Molecular Pharmaceutics, 11: 3528-3536.*

(Continued)

*Primary Examiner* — Amber D Steele
(74) *Attorney, Agent, or Firm* — Sheppard Mullin Richter & Hampton LLP

(57) ABSTRACT

The present invention generally relates to the field of antimicrobial peptides (AMPs), and more specifically to cationic intrinsically disordered antimicrobial peptides (CI-DAMPs) and their use as disinfectants and therapeutic agents for the treatment of infections, especially as a therapeutic alternative for the treatment of infectious diseases caused by antibiotic resistant microorganisms.

9 Claims, 16 Drawing Sheets

Specification includes a Sequence Listing.

(56) References Cited

OTHER PUBLICATIONS

Wu et al., 2009, Highly Complex Peptide Aggregates of the S100 Fused-Type Protein Hornerin Are Present in Human Skin, Journal of Investigative Dermatology, 129: 1446-1458.*

Xue et al., 2014, intrinsic Disorder in Proteins Involved in the Innate Antiviral Immunity: Another Flexible Side of a Molecular Arms Race, J Mol Biol, 426: 1322-1350.*

Jackson et al., 2005, Late Cornified Envelope Family in Differentiating Epithelia-Response to Calcium and Ultraviolet Irradiation, J Invest Dermatol, 124: 1062-1070.*

Niehues et al., 2017, Psoriasis-associated Late Cornified Envelope (LCE) Proteins Have Antibacterial Activity, J Invest Dermatol, 137(11): 2380-2388.*

Hansmann et al., 2015, Skin-Derived C-Terminal Filaggrin-2 Fragments Are Pseudomonas aeruginosa-Directed Antimicrobials Targeting Bacterial Replication, PLoS Pathogens, 11(9): e1005159 (21 pages).*

Makovitzki et al., 2008, Antimicrobial Lipopolypeptides Composed of Palmitoyl Di- and Tricationic Peptides: In Vitro and in Vivo Activites, Self-Asselbly to Nanostructures, and a Plausible Mode of Action, Biochemistry, 47: 10630-10636.*

Database UniProt[Online] Mar. 15, 2004, "RecName: Full= Hornerin", retrieved from EBI accession No. UniProt:Q86YZ3, XP-002768148.

Extended European Search Report for EP Appln. No. 16199780.4 dated Mar. 22, 2017, 14 pages.

International Search Report and Written Opinion for PCT/EP2017/079307 dated Mar. 21, 2018, 19 pages.

Libardo et al., "Improved Bioactivity of Antimicrobial Peptides by Addition of Amino-Terminal Copper and Nickel (ATCUN) Binding Motifs", ChemMedChem, 2014, vol. 9, pp. 1892-1901.

Martino et al., "Elastin-Based Biopolymers: Chemical Synthesis and Structural Characterization of Linear and Cross-Linked Poly(OrnGlyGlyOrnGly)", Biomacromolecules, 2002, vol. 3, pp. 297-304.

Novak et al., "Interaction of Tyrosyl, Histidyl, and Tryptophanyl Peptides with DNA: Specificity and Mechanism of the Interaction", Nucleic Acids Research, 1974, vol. 1, No. 6, p. 761-766.

Olsson et al., "Molecular Parameters That Control The Association Of Low Density Lipoprotein APO B-100 with Chondroitin Sulphate", Biochimica et Biophysica Act, 1991, vol. 1097, No. 1, pp. 37-44.

Tossi et al., "Amphipathic, alpha-Helical Antimicrobial Peptides", Biopolymers, 2000, vol. 55, No. 1, pp. 4-30.

Wu, "Analysis of Two Human Gene Clusters Involved in Innate Immunity" Dissertation zur Erlangung des Doktorgrades der Mathematisch Naturwissenschaftlichen Fakultät der Christian-Albrechts-Universität zu Kiel, Dec. 8, 2005, 126 pages.

* cited by examiner

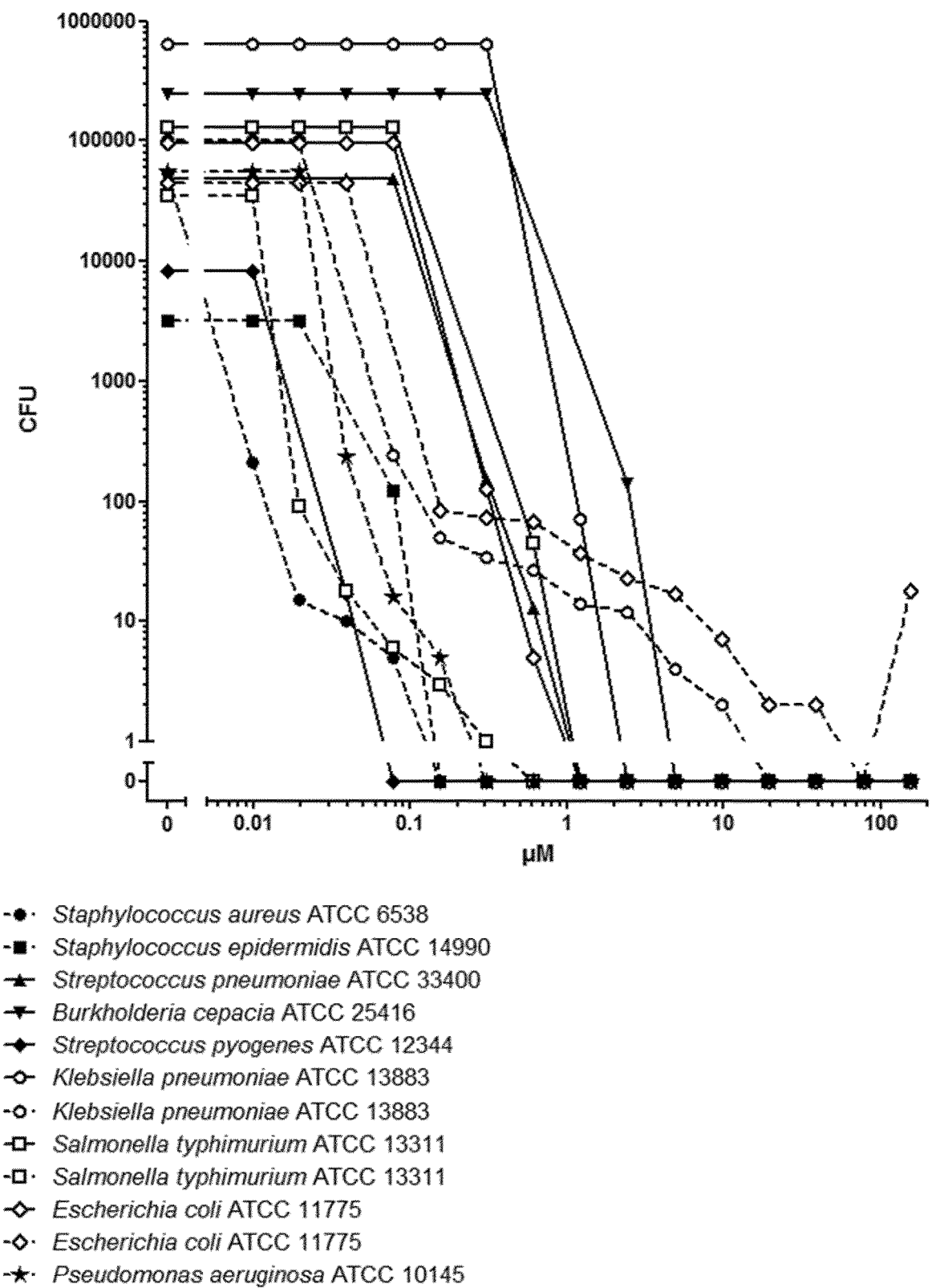

- • Staphylococcus aureus ATCC 6538
- ■ Staphylococcus epidermidis ATCC 14990
- ★ Streptococcus pneumoniae ATCC 33400
- ▼ Burkholderia cepacia ATCC 25416
- ♦ Streptococcus pyogenes ATCC 12344
- ○ Klebsiella pneumoniae ATCC 13883
- ○ Klebsiella pneumoniae ATCC 13883
- □ Salmonella typhimurium ATCC 13311
- □ Salmonella typhimurium ATCC 13311
- ◇ Escherichia coli ATCC 11775
- ◇ Escherichia coli ATCC 11775
- ★ Pseudomonas aeruginosa ATCC 10145

Fig. 14

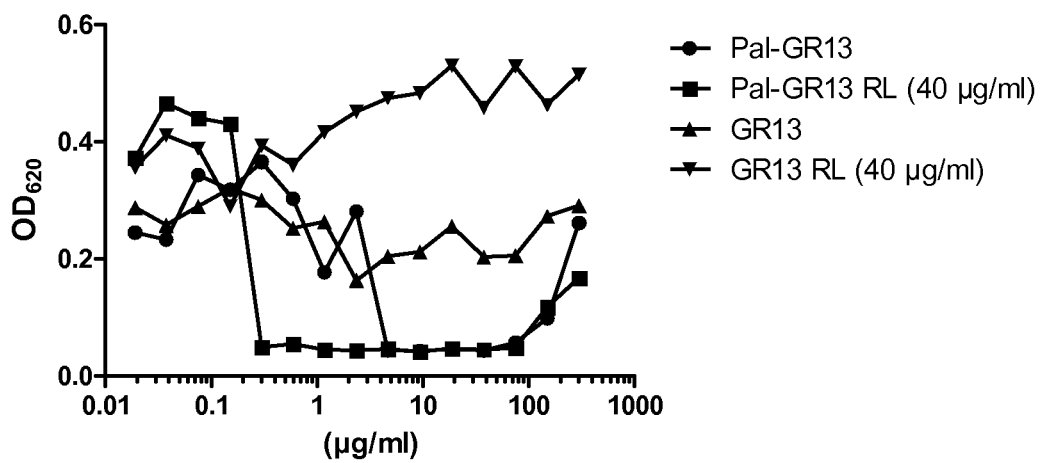
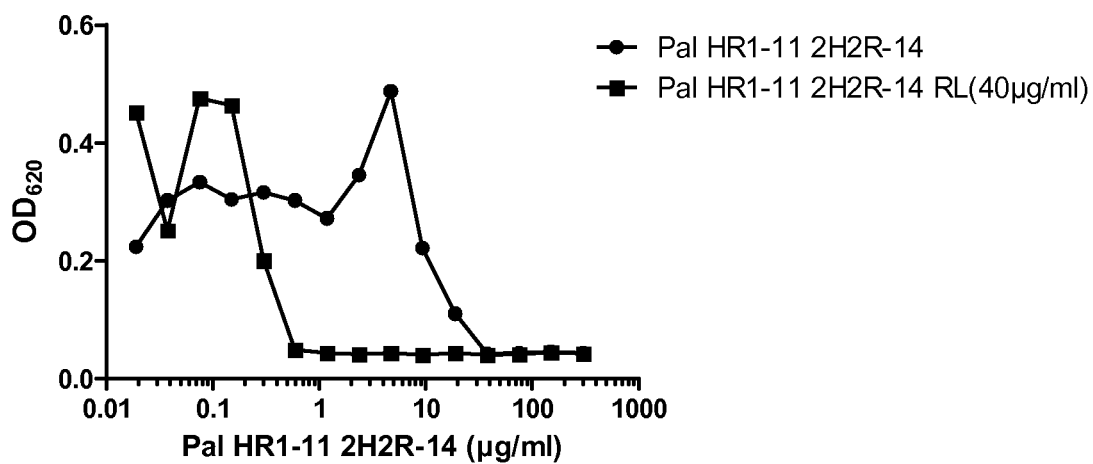
Fig. 15

CATIONIC INTRINSICALLY DISORDERED ANTIMICROBIAL PEPTIDES

CROSS-REFERENCE TO RELATED APPLICATIONS

This application is a U.S. National Stage Application under 35 U.S.C. § 371 of International Application No. PCT/EP2017/079307, filed Nov. 15, 2017, which application claims the benefit of European Application No. 16199780.4, filed Nov. 21, 2016.

SEQUENCE LISTING

The instant application contains a Sequence Listing which has been submitted electronically in ASCII format and is hereby incorporated by reference in its entirety. Said ASCII copy, created on Jan. 11, 2021, is named 297659US_ST25.txt and is 50 KB in size.

FIELD OF THE INVENTION

The present invention generally relates to the field of antimicrobial peptides (AMPs), and more specifically to cationic intrinsically disordered antimicrobial peptides (CI-DAMPs) and their use as disinfectants and therapeutic agents for the treatment of infections, especially as a therapeutic alternative for the treatment of infectious diseases caused by antibiotic resistant microorganisms.

BACKGROUND OF THE INVENTION

The widespread use of antibiotics (e.g., in food and livestock industrial products) during the last decades has promoted the development of antibiotic resistance. Today, antibiotic resistance is a serious and life-threatening clinical and public health problem of world-wide relevance.

Antibiotics are a diverse group of compounds that may be categorized according to their principal modes of action, including interference with cell wall synthesis (e.g., beta-lactams and glycopeptide agents), inhibition of protein synthesis (macrolides and tetracyclines), interference with nucleic acid synthesis (fluoroquinolones and rifampin), inhibition of metabolic pathways (trimethoprim-sulfamethoxazole), and disruption of bacterial membrane structure (polymyxins and daptomycin) (Tenover, F., 2006, *Am. J. Med.*, 119, S3-S10).

While antibiotics are being successfully used in a wide variety of infectious diseases, various pathogenic bacteria may be intrinsically resistant to different types of antimicrobial agents, or may acquire resistance by de novo mutation or via the acquisition of resistance genes from other organisms. The acquisition of new genetic material may occur through conjugation, transformation, or transduction, with transposons often facilitating the incorporation of the multiple resistance genes into the host's genome or plasmids (Tenover, supra, and Davies and Stone, 1986, *Eur. J. Clin. Microbiol.* 5, 277-281).

The main mechanisms of antibiotic resistance include inactivation of the antibiotic, alteration of the antibiotic's target site, blockage in the transport of the antibiotic, expression of efflux systems, use of alternative metabolic pathways, expression of increased levels of the target (e.g., the inhibited enzyme), and inhibiting the antibiotic-sensitive step by endogenous or exogenous products (Davies and Stone, supra). A major disadvantage of antibiotics is their activity against commensals with the consequence of disrupting the microflora and subsequent post-antibiotic-treatment side effects.

Intense efforts have been made in the past to discover and develop new and improved antibiotics against strains of bacteria that are resistant to conventionally used antibiotics. It was found that antimicrobial peptides (AMPs) can provide a therapeutic alternative for the treatment of infectious diseases caused by antibiotic resistant microorganisms (Cruz et al., 2014, *Curr. Med. Chem.*, 21, 1-23; Hancock et al. 2006, *Nat. Biotechnol.*, 24, 1551-1557).

AMPs are essential components of host defense against infections and are ubiquitous in nature, being widely distributed in microorganisms, plants and animals (Yeaman and Yount 2003, *Pharmacol. Rev.*, 55, 27-55; Zasloff, M., 2002, *Nature* 415, 389-395). They are relatively small (12 to 100 amino acids), cationic and amphipathic peptides of variable length, sequence and structure. AMPs display a broad spectrum of antimicrobial activity, being effective against both Gram-positive and Gram-negative bacteria, fungi, enveloped viruses, parasites and some types of cancer (Cruz et al., supra; Brown and Hancock, 2006, *Curr. Opin. Immunol.* 18, 24-30; Jenssen et al., 2006, *Clin. Rev. Microbiol.* 19, 491-511).

The vast majority of AMPs is, mostly inducibly, expressed in epithelial cells of multicellular organisms. Vertebrate skin, trachea and tongue epithelia are sources of these AMPs, which may in part explain the unexpected resistance of these tissues towards infection. Human skin is a particularly rich source of antimicrobial peptides. Their cellular source includes keratinocytes, which terminally differentiates, eventually forming the stratum corneum, the horny layer.

The easy availability of stratum corneum allowed the identification and characterization of a number of human antimicrobial peptides. Moreover, the availability of lesional scales of patients with psoriasis allowed to find inducible peptide antibiotics, which are absent in healthy skin. Specifically, the cationic and amphipathic beta-defensins hBD-2 (Harder et al., 1997, *Nature* 387, 861), hBD-3 (Harder et al., 2001, *J. Biol. Chem.* 276, 5707-13) and RNase-7 (Harder et al., 2002, *J. Biol. Chem.* 277, 46779-84) together with the cathelicidin LL-37 (Gudmundsson et al., 1996, *Eur. J. Biochem.*, 238, 325-32; Lande et al., 2007, *Nature* 449, 564-9; Lande et al., 2015, *Eur. J. Immunol.* 45, 203-13) have been identified as cationic human antimicrobial peptides and proteins in inflamed skin.

Unlike most antibiotics that typically target specific proteins, AMPs can act on bacterial membranes or other targets different to those of conventional antibiotics, and generally have a different mode of action as compared to that of conventional antibiotics (Stoop et al., 2010, *Mol. Cell Proteomics* 9, 2063-2075). This makes AMPs essentially insusceptible to microbial resistance. As a result, AMPs constitute promising candidates for clinical developments against microbial infections.

However, a major drawback to the use of many of these amphipathic and cationic antimicrobial peptides as antibiotics is their toxicity and/or ability to lyse eukaryotic cells (Hancock and Lehrer, 1998, *Trends Biotechnol.* 16, 82-8). For a peptide to be useful as an antibiotic, it should have an increased antimicrobial activity and a reduced toxicity to normal cells.

Another disadvantage of natural cationic AMPs is their relatively large molecular size, which requires costly recombinant biotechnical synthesis. A synthetic peptide approach to examining the effect of changes, including small or incremental changes, in hydrophobicity/hydrophilicity, amphipathicity, helicity and molecular size of cationic antimicrobial peptides can facilitate rapid progress in rational design of amphipathic peptide antibiotics. However, many of these peptides are still toxic and need micromolar to low millimolar concentration (depending on the size and structure) for effective bacteriostatic or bactericidal activity (Domalaon et al., 2016, *Curr. Top. Med. Chem.* 16, 1217-30), possibly because the formation of pores requires the amphipathic AMPs to be present in the micromolar range (Kurut et al., 2014, *Proteins* 82, 657-67; Roversi et al., 2014, *ACS Chem. Biol.* 19, 2003-7).

In the last years, there has been a shift in the paradigm that protein function always requires well-defined conformations. It was found that there are proteins or sizeable regions of proteins that lack a well-defined conformation, which are commonly referred to as "intrinsically disordered proteins" (IDPs) or "intrinsically disordered protein regions" (IDPRs). Many IDPs are functional and adopt a defined conformation upon interaction with a target molecule. It is estimated that long IDPRs are found in about 33% of eukaryotic proteins (Ward et al., 2004, *J. Mol. Biol.* 337, 635-645).

The structural disorder of IDPs/IDPRs is caused by their distinct amino acid content. Usually, they have a low hydrophobicity content combined with a high net charge content (Uversky V. N., 2013, *Protein Sci.* 22, 693-724). Comparison of amino acid sequences of IDPs/IDPRs with ordered proteins and domains revealed that IDPs/IDPRs are significantly depleted in order-promoting amino acids (e.g., Trp, Tyr, Phe, Ile, Leu, Val, Cys, and Asn), and are generally enriched in disorder-promoting residues (e.g., Ala, Arg, Gly, Gln, Ser, Glu, and Lys) (Uversky V. N., 2013, *Protein Sci.* 22, 693-724). Thus, in IDPs the amino acid composition, rather than the amino acid sequence determines the disorder promoting properties (Uversky V. N., 2002, *Protein Sci.* 11, 739-756).

Most of the functions of IDPs are related to molecular recognition of DNA, RNA, and other proteins (Hansen et al., 2006, *J. Biol. Chem.* 281, 1853-56). IDPs and IDPRs are highly susceptible towards proteolysis and are frequently involved in transcription, cell cycle regulation, signal transduction, chaperoning the folding of proteins and RNA etc. (Hansen et al., supra). Partially disordered regions are often found at the amino and carboxyl ends of proteins, but can also be present at internal sites. Based on their function, IDPs have been grouped into two main categories: mediators of macromolecular interactions and entropic connectors/springs (Tompa, P., 2005, *FEBS Lett.* 579, 3346-3354). Many IDPs appear to be involved in innate immunity against virus infections, suggesting that host cells use numerous advantages of IDPs to overcome viral infections (Xue and Uversky, 2014, *J. Mol. Biol.* 426, 1322-50).

Recently, it was discovered that recombinantly generated 8-16 kDa peptide fragments exhibit antimicrobial activity (Wu et al., 2009, *J. Invest. Dermatol.* 129, 1446-58). This led to the novel concept that cationic IDPs may also be antimicrobial peptides, challenging the dogma that antimicrobial peptides are amphipathic peptides having microbial membrane-active properties. Despite recent efforts to develop antimicrobials based on AMPs or IDPs, there remains an ongoing need for new and improved antimicrobial compounds.

OBJECT OF THE INVENTION

In view of the above, the object of the present invention is to provide antimicrobial peptides useful as disinfectants and/or for the treatment of infectious diseases.

SUMMARY OF THE INVENTION

According to the present invention, it was unexpectedly found that the above object is achieved by a novel class of cationic antimicrobial peptides having an intrinsically disordered structure (in the following referred to as "cationic intrinsically disordered antimicrobial peptides" or "CIDAMPs"). Surprisingly, contrary to the principle that the amino acid sequence determines the function of a peptide, the amino acid composition of the CIDAMPs was found to determine their activity.

In a first aspect, the present invention provides an antimicrobial peptide having an amino acid composition consisting of:
  (a) 70% to 100%, particularly 75% to 100%, of at least two disorder-promoting amino acids selected from the group consisting of arginine (Arg), glycine (Gly), histidine (His), glutamine (Gln), serine (Ser), lysine (Lys), diaminobutyric acid (Dab), diaminopropionic acid (Dap), ornithine (Orn), and amino acid derivatives thereof,
  (b) 0% to 20%, particularly 0% to 15%, of at least one disorder-promoting amino acid selected from the group consisting of proline (Pro), glutamic acid (Glu), and amino acid derivatives thereof,
  (c) 0% to 30%, particularly 0% to 25%, of at least one order-promoting amino acid selected from the group consisting of tryptophan (Trp), tyrosine (Tyr), phenylalanine (Phe), isoleucine (Ile), leucine (Leu), valine (Val), cysteine (Cys), asparagine (Asn), and amino acid derivatives thereof,
  (d) 0% to 30%, particularly 0% to 25%, of at least one order-neutral amino acid selected from the group consisting of alanine (Ala), threonine (Thr), aspartic acid (Asp), methionine (Met), and amino acid derivatives thereof,
  wherein the percentages of (a), (b), (c) and (d) add up to 100%, and the peptide has a positive net charge at pH 5.5, particularly at pH 7.0.

In another aspect, the present invention provides a method of increasing antimicrobial activity and/or chemical stability and/or decreasing cytotoxic activity of an antimicrobial peptide according to the present invention, wherein the method comprises one or more of the following steps:
  (a) replacing one or more His by Arg,
  (b) replacing one or more L-amino acids by the corresponding D-amino acid or vice versa,
  (c) replacing one or more amino acids that are either neutral or negatively charged at pH 7.0 by one or more amino acids that are positively charged at pH 7.0,
  (d) replacing one or more amino acids by an amino acid where the α-amino group is replaced by an α-hydroxy group,
  (e) adding the N-terminal sequence Gly-X-His (ATCUN-motif), where X can be any amino acid,
  (f) adding at the N-terminus an N-palmitoylated Gly or any other N-palmitoylated amino acid or at the C-terminus an S-palmitoyl-Cys-amide,
  (g) adding at any position within the peptide an O-palmitoyl-Ser, an O-palmitoyl-Thr or any other O-palmitoyl-group-containing amino acid, (h) adding any anionic detergent, particularly rhamnolipids, to increase affinity to lipophilic skin surfaces,
(i) adding gluconate to increase CIDAMP solubility and affinity to mucosal surfaces,
(j) replacing one, two, three or four amino acids by Cys, preferably for introducing a thiol-based high affinity zinc binding site, and
(k) replacing one, two or three Cys by His, to generate His-based zinc-, manganese- or iron(II)-binding sites in the peptide.

In a further aspect, the present invention relates to a composition, in particular a topical pharmaceutical composition, comprising at least one antimicrobial peptide as described herein and a carrier.

In a still further aspect, the present invention relates to an antimicrobial peptide or a mixture of antimicrobial peptides of the present invention for use as a medicament. In particular, the antimicrobial peptide of the present invention is suitable for use in the prevention and/or treatment of bacterial and fungal infections.

In yet another aspect, the present invention relates to the use of an antimicrobial peptide of the present invention for cosmetic applications.

In still another aspect, the present invention relates to the use of an antimicrobial peptide of the present invention for use as preservative, e.g., for use as preservative in cosmetic preparations or as agent of biocontrol in food and agriculture or as additive in feed for domestic animals like pigs and cattle.

In a yet further aspect, the present invention relates to an antimicrobial peptide of the present invention as commensal microbiota sparing, broad-spectrum disinfectant of skin and mucosal surfaces, in particular as disinfectant for sterilizing surfaces, e.g., for use as antiseptic or contact lens solutions or dental hygiene products or implantable medical devices.

Preferred embodiments of the present invention are set forth in the appended claims. Further embodiments and other objects, advantages and features of the present invention will become apparent from the following detailed description of the invention and the examples.

BRIEF DESCRIPTION OF THE DRAWINGS

The present invention is further illustrated by reference to the accompanying drawings, in which:

FIG. 14 shows the antimicrobial activity spectrum of Pal-LCE3B$_{56-68}$ against several bacterial strains. The CFU-assay was performed at pH 7.3 (-) or at pH 5.5 ( - - - );

FIG. 15 shows the *S. aureus*-cidal activity of Pal-GR13, GR13 and Pal-HR 1-11 2H2R-14 in the absence or in the presence of rhamnolipids (RL);

DETAILED DESCRIPTION OF THE INVENTION

Figure 1:
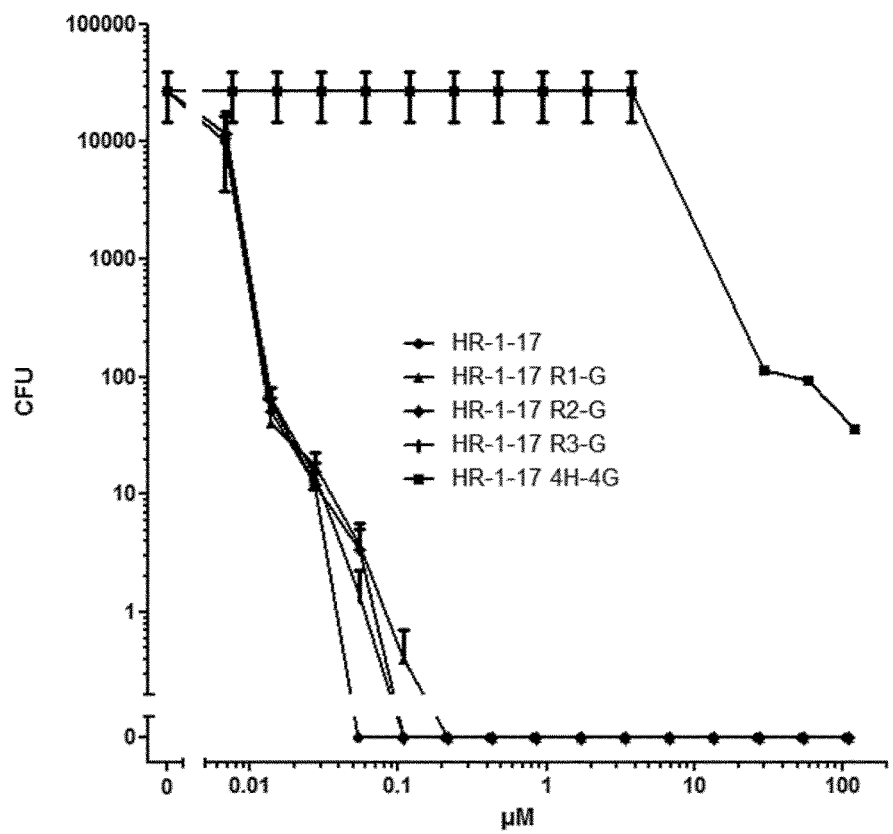
FIG. 1 shows the *P. aeruginosa* ATCC 10145-cidal activity of HR 1-17 peptides.

The inventors of the present invention have unexpectedly found that a specific class of cationic peptides having an intrinsically disordered structure are effective antimicrobial agents (in the following referred to as "cationic intrinsically disordered antimicrobial peptides" or "CIDAMPs"). These CIDAMPs have been found to exhibit high antimicrobial activity against a broad range of pathogenic microorganisms, including many Gram-negative and Gram-positive bacteria as well as fungi like *Candida albicans* and *Cryptococcus neoformans*.

Advantageously, these peptides can be highly specific for a given pathogenic microorganism or groups of pathogenic microorganisms, while sparing the commensal microflora, and having minimal side effects. Additionally, the CIDAMPs of the present invention offer the possibility to provide highly efficient preservatives (e.g., in cosmetic preparations), agents of biocontrol in food and agriculture, additives in feed for domestic animals, and disinfecting agents for sterilizing various surfaces.

A further advantage is that the different targets and mechanisms of action compared to conventional antibiotics render CIDAMPs practically insusceptible to antimicrobial resistance. This means that the CIDAMPs of the present invention provide a therapeutic alternative for the treatment or prevention of infectious diseases caused by antibiotic-susceptible or -resistant microorganisms. Moreover, since CIDAMPs represent highly hydrophilic proteins, lacking secondary amphipathic structures that could lead to membrane lysis, CIDAMS are expected to have low—if any—cytotoxic activity.

Furthermore, due to the dependence of the amino acid composition and independence of the amino acid sequence, CIDAMPs have a very high structural versatility and flexibility, to date not seen with any of the amphipathic AMPs nor with classical antibiotics. Still another advantageous aspect of the present invention is the possibility of preparing CIDAMPs in a cost-efficient manner using, for example, solid-phase chemical synthesis.

In a first aspect, the present invention provides an antimicrobial peptide having an amino acid composition consisting of:
(a) 70% to 100%, particularly 75% to 100%, of at least two disorder-promoting amino acids selected from the group consisting of arginine (Arg), glycine (Gly), histidine (His), glutamine (Gln), serine (Ser), lysine (Lys), diaminobutyric acid (Dab), diaminopropionic acid (Dap), ornithine (Orn), and amino acid derivatives thereof,
(b) 0% to 20%, particularly 0% to 15%, of at least one disorder-promoting amino acid selected from the group consisting of proline (Pro), glutamic acid (Glu), and amino acid derivatives thereof,
(c) 0% to 30%, particularly 0% to 25%, of at least one order-promoting amino acid selected from the group consisting of tryptophan (Trp), tyrosine (Tyr), phenylalanine (Phe), isoleucine (Ile), leucine (Leu), valine (Val), cysteine (Cys), asparagine (Asn), and amino acid derivatives thereof,
(d) 0% to 30%, particularly 0% to 25%, of at least one order-neutral amino acid selected from the group consisting of alanine (Ala), threonine (Thr), aspartic acid (Asp), methionine (Met), and amino acid derivatives thereof,
wherein the percentages of (a), (b), (c) and (d) add up to 100%, and the peptide has a positive net charge at pH 5.5, particularly at pH 7.0.

As used herein, the term "peptide" refers to amino acid sequences of a certain length. Usually, the peptides are between four and one hundred amino acids in length. The term "antimicrobial", as used herein, generally means having to do with the killing, growth inhibition or growth prevention of microorganisms. "Growth inhibition" means reduced growth of the microorganisms. "Growth prevention" means that growth is stopped. The term "microorganism" broadly refers to bacteria (including the domains Bacteria and Archaea), fungi (including unicellular and filamentous fungi, e.g. yeast), parasites (including unicellular and multicellular parasites), and viruses, and more specifically means bacteria and fungi, in particular bacteria.

The term "amino acid derivative" is intended to refer to non-proteinogenic amino acids derived from said disorder-promoting, order-promoting and order-neutral amino acids by replacing one or more individual atoms with a different atom or with a different functional group (e.g., a functional group of no more than 15 atoms), and/or by eliminating the amine group or carboxylic group linked to the α-carbon of the amino acid, and/or by modifying the side group of the amino acids by esterification, amidation or hydrolysis of functional groups. As used herein, the standard three-letter or one-letter abbreviations are used to identify specific amino acids. For the purpose of the present invention, however, cysteine (Cys) may include selenocysteine (Sec), but preferably is cysteine only.

Within the present invention, the percentage of (a) in the antimicrobial peptide as defined above is preferably 70% to 100%, 75% to 100%, 80% to 100%, 85% to 100%, 90% to 100%, 95% to 100%, 70% to 95%, 75% to 90%, 80% to 85%, or 100%. The percentage of (b) is preferably 0% to 20%, 0% to 15%, 0% to 10%, 0% to 5%, 5% to 20%, 10% to 15%, or 0%. The percentage of (c) is preferably 0% to 30%, 0% to 20%, 0% to 15%, 0% to 10%, 0% to 5%, 5% to 25%, 10% to 20%, or 0%. The percentage of (d) is preferably 0% to 30%, 0% to 20%, 0% to 15%, 0% to 10%, 0% to 5%, 5% to 25%, 10% to 20%, or 0%. It should be understood that this paragraph specifically discloses all possible combinations of the percentages or percentage ranges indicated above, and which are all within the scope of the present invention.

Furthermore, irrespective of the above, the two amino acids Gly and Ser may account for about 30% to 75%, preferably for about 40% to 70%, more preferably for about 50% to 70%, and most preferably about 55% to 65% of all amino acids in the antimicrobial peptide. In addition to, or independently from, the percent ratio of Gly and Ser, the amino acids Arg, Lys and His, preferably Arg and His, may account for about 20% to 75%, preferably for about 25% to 60%, more preferably for about 30% to 50%, and most preferably for about 35% to 45% of all amino acids in the antimicrobial peptide of the present invention.

In addition, the ratio of the total number of Arg, Lys and His to the total number of Arg, Lys, His, Orn, Dab and Dap is 0% to 100%, preferably 50% to 95%, more preferably 65% to 90%, and most preferably 75% to 85%. Moreover, the sum of Dab, Dap and Orn may account for 0% to 50%, in particular 25% or less or 15 or less of all amino acids in the antimicrobial peptide of the present invention.

It is further contemplated that the antimicrobial peptide of the present invention is a peptide in which 25% or less, preferably 20% or less, more preferably 15% or less, and most preferably 0% to 10% of each of said disorder-promoting amino acids of (a) and (b), said order-promoting amino acids of (c), and said order-neutral amino of (d) are replaced by (the same or different) amino acid derivatives.

Preferably, the at least two disorder-promoting amino acids of the antimicrobial peptide of the present invention are selected from the group consisting of:
Arg, Gly, His, Gln, Lys, Dab, Dap, Orn, and amino acid derivatives thereof,
Arg, Gly, His, Ser, Lys, Dab, Dap, Orn, and amino acid derivatives thereof,
Arg, Gly, His, Gln, Ser, Lys, and amino acid derivatives thereof, or of
Arg, Gly, His, Gln, Ser, and amino acid derivatives thereof, or of
Arg, Gly, His, Ser, Dab, Dap, Orn, and amino acid derivatives thereof, or of
Arg, Gly, His, Ser, and amino acid derivatives thereof.

Further, the at least one disorder-promoting amino acid of the antimicrobial peptide of the present invention is preferably Pro or Glu, in particular Pro, and amino acid derivatives thereof.

In addition, the at least one order-promoting amino acid of the antimicrobial peptide of the present invention is preferably selected from the group consisting of:
Tyr, Phe, Ile, Leu, Val, Cys, Asn, and amino acid derivatives thereof, or of
Tyr, Phe, Leu, Val, Cys, Asn, and amino acid derivatives thereof, or of
Tyr, Phe, Ile, Val, Cys, Asn, and amino acid derivatives thereof, or of
Tyr, Phe, Ile, Leu, Cys, Asn, and amino acid derivatives thereof, or of
Ile, Leu, Val, Cys, Asn, and amino acid derivatives thereof, or of
Tyr, Phe, Cys, Asn, and amino acid derivatives thereof, or of
Leu and amino acid derivatives thereof, or of
Cys and amino acid derivatives thereof.

Moreover, the at least one order-neutral amino acid of the antimicrobial peptide of the present invention is preferably selected from the group consisting of:
Ala, Thr, Asp, Met, and derivatives thereof, or of
Ala, Thr, Asp, and derivatives thereof, or of
Thr, Asp, and derivatives thereof, or of
Ala, Asp, and derivatives thereof, or of
Ala, Thr, and derivatives thereof, or of
Ala and derivatives thereof, or of
Asp and derivatives thereof.

Furthermore, the antimicrobial peptide of the present invention may contain 100% L-amino acids or 100% D-amino acids, or X % L-amino acids and Y % D-amino acids with X>1%, Y>1% and X+Y=100%. In one embodiment, the antimicrobial peptides of the present invention are characterized in that 50% to 100% of all Arg and/or Lys amino acids in the antimicrobial peptide are D-Arg and/or D-Lys amino acids.

The antimicrobial peptide of the present invention generally has a length of at least 4 amino acids. Preferably, the length is 7 to 100 or 9 to 50, more preferably 9 to 30, and most preferably 9 to 25 or 12 to 25 amino acids.

The net charge of the antimicrobial peptide of the present invention at pH 5.5 is at least +2, preferably +3, more preferably at least +4, and most preferably at least +5, and/or the net charge at pH 7.0 is at least +2, preferably at least +3, more preferably at least +4, and most preferably at least +5. Further, at least 20% of all amino acids of the antimicrobial peptide, preferably 20% to 75%, more preferably 20% to 65% or 20% to 40% or 20% to 30%, and most preferably 25% to 35%, are cationic at pH 5.5, preferably also at pH 7.0.

According to the present invention, the antimicrobial peptide may comprise covalently attached chemical moieties. The moieties may include fluorescence or other labels, sugars, lipids or the like, but exclude proteinogenic amino acids. In particular, the antimicrobial peptide may be modified by one or more hydrophobic moieties, preferably a group represented by —R or —C(=O)—O—R with R being a linear or branched, substituted or unsubstituted $C_8$-$C_{30}$, preferably $C_{10}$-$C_{22}$, more preferably $C_{12}$-$C_{20}$, and most preferably $C_{14}$-$C_{18}$ alkyl, alkenyl or alkinyl group. Preferably, the antimicrobial peptide is N- or S-acylated, and the acyl group preferably consists of a carbonyl group and a $C_8$-$C_{30}$, preferably, $C_{10}$-$C_{22}$, more preferably $C_{12}$-$C_{20}$, and most preferably $C_{14}$-$C_{18}$ alkyl group. More preferably, the antimicrobial peptide is N-palmitoylated, S-palmitoylated, O-palmitoylated, N-myristoylated, or any combination thereof, and most preferably N- or S- or O-palmitoylated. The palmitoyl and/or myristoyl modifications are preferably located at the N- and/or C-terminus of the peptide, in particular only at the N-terminus.

In one embodiment, the antimicrobial peptide of the present invention:
(i) has a length of between 4 to 25, preferably 4 to 22, more preferably 4 to 15, and most preferably 4 to 13 amino acids,
(ii) consists of at least two cationic amino acids and at least two other amino acids, the cationic amino acids being selected from Arg, Lys, His, Orn, Dab and Dap, preferably from Arg, His and Orn, more preferably from Arg and His, and most preferably from Arg, and the other amino acid being selected from Gly, Leu, Ser, Gln, Asp, Cys and Pro, preferably from Gly and Ser, more preferably from Gly, and optionally
(iii) has one or more covalently attached fatty acid residues, the peptide being preferably N- or S- or O-palmitoylated and/or N-myristoylated, more preferably N- or S- or O-palmitoylated.

The antimicrobial peptide of said one embodiment preferably contains at the N-terminus and/or C-terminus a fatty acid residue (e.g., a myristoyl or palmitoyl residue), preferably a N-palmitoyl-Gly and/or S-palmitoyl-Cys moiety. Moreover, the antimicrobial peptide of said one embodiment preferably consists of at least one Gly amino acid and at least one cationic amino acid selected from Arg His, Orn, Dab and Dap, preferably from Arg and His.

The antimicrobial peptide of said one embodiment may also preferably contain an O-palmitoyl-Ser residue. Such a residue may be localized at differing positions of the peptide, not only at the N-terminus and/or C-terminus. The flexible positioning of such an O-palmitoyl-Ser residue in the peptide chain can lead to the reduction or even the avoidance of cytotoxicity effects.

In another embodiment of the present invention, the antimicrobial peptide has an amino acid composition consisting of:
(a) 70% to 90%, particularly 75% to 85%, of at least two disorder-promoting amino acids selected from the group consisting of Arg, Gly, His, Gln, Ser, Lys, Dab, Dap, Orn, and amino acid derivatives thereof, the at least two disorder-promoting amino acids being particularly selected from the group consisting of Arg, His, Gln, Ser, and amino acid derivatives thereof,
(b) 0% to 10%, particularly 0% to 5%, of at least one disorder-promoting amino acid selected from the group consisting of Pro, Glu, and amino acid derivatives thereof, the at least one disorder-promoting amino acid being particularly Pro,
(c) 5% to 30%, particularly 10% to 25%, of at least one order-promoting amino acid selected from the group consisting of Trp, Tyr, Phe, Ile, Leu, Val, Cys, Asn, and amino acid derivatives thereof, the at least one order-promoting amino acid being preferably Asp,
(d) 0% to 15%, particularly 0% to 10% of at least one order-neutral amino acid selected from the group consisting of Ala, Thr, Asp, Met, and amino acid derivatives thereof,
wherein the percentages of (a), (b), (c) and (d) add up to 100%, and wherein the peptide has a positive net charge at pH 5.5, particularly at pH 7.0, and preferably contains at least two neighboring histidine residues. The explanations and definitions given above in relation to the optionally present chemical moieties, in particular the optionally present fatty acid residues, equally apply to this embodiment.

In accordance with the present invention, the antimicrobial peptide has antimicrobial activity against at least one bacterial species selected from the group consisting of *Staphylococcus* spp. (e.g., *Staphylococcus aureus*), *Streptococcus* spp. (e.g., *Streptococcus pneumoniae*), *Burkholderia* spp. (e.g., *Burkholderia cepacia*), *Pseudomonas* spp. (e.g., *Pseudomonas aeruginosa*), *Escherichia* spp. (e.g., *Escherichia coli*), *Klebsiella* spp. (e.g., *Klebsiella pneumoniae*), *Propionibacterium* spp. (e.g., *Propionibacterium acnes*), *Prevotella* spp. (e.g., *Prevotella oralis*), *Clostridium* spp. (e.g., *Clostridium perfringens*), *Corynebacterium* spp. (e.g., *Corynebacterium simulans*), *Salmonella* spp. (e.g., *Salmonella typhimurium*), *Acinetobacter* spp. (e.g., *Acinetobacter baumanii*), *Paenibacillus* spp. (e.g., *Paenibacillus larvae*) and/or wherein the peptide has antifungal activity, in particular against yeasts (e.g., *Candida albicans, Cryptococcus neoformans*), filamentous fungi such as dermatophytes (e.g., *Malassezia* spp.), or *Aspergillus* ssp. (e.g., *Aspergillus fumigatus*).

In particular, the antimicrobial peptide has antimicrobial activity against bacteria belonging to the genus *Pseudomonas* as the largest phylotype of human skin. *Pseudomonas* spp. are very frugal soil- and water born bacteria, thriving at moist conditions on skin niches of healthy persons, but can be opportunistic pathogens, particularly under conditions where the cutaneous barrier is completely missing as in burn wounds, where *P. aeruginosa* is a major cause of morbidity and mortality. Currently, drug resistance, especially against cephalosporins and carbapenems, among *P. aeruginosa* and other Gram-negative bacteria is an important challenge, which is further enhanced by the limited availability of drugs against these microorganisms.

There are certain antibiotics (colistin, fosfomycin, temocillin, and rifampicin) that have been revived from the past to tackle the menace of "superbugs". However, very few newer antibiotics, which mostly belong to known chemical antibiotic classes, have been added to the pool of existing drugs. Thus, the present invention represents a significant contribution to the field of antimicrobials by providing new antibiotics targeting *P. aeruginosa* and other Gram-negative bacteria.

The standard assay procedures for screening for antimicrobial activity outlined by the Clinical and Laboratory Standards Institute are optimized for the discovery of antibiotic-resistant bacteria present in blood (Steinberg and Lehrer, 1997, *Methods Mol. Biol.*, 78, 169-86). The media used are rich in artificial nutrients, have a neutral pH and physiologic ion concentrations—an environment which is far away from the environment of many microbes in their natural habitats. Thus, using the standard assay system, one will potentially miss antibiotics, which are only active at different, yet to be defined assay conditions.

Since healthy skin surface is acidic, low in ions, and limited in nutrients, an assay buffer mimicking natural skin conditions with low ion strength, at pH 5.5, without nutrients and containing only glucose as energy source, was developed and used by the inventors. This assay system enables the detection of antimicrobial activities otherwise undetectable with the standard procedures outlined by the Clinical and Laboratory Standards Institute and commonly used for antibiotic discovery. Human skin antimicrobial peptides, e.g., against *P. aeruginosa*, in general have the highest activity at pH 5.5 and are inhibited by the presence of nutrients.

Thus, within the present invention, the antimicrobial activity is generally measured in nutrient deficient 10 mM sodium phosphate buffer pH 5.5, containing 0.25% glucose, using the CFU-assay according to Steinberg and Lehrer, 1997 (supra), unless otherwise indicated. The CFU-assay allows determination of the minimal bactericidal concentration (MBC, e.g., $MBC_{90}$ and $MBC_{100}$; i.e. the concentration of compound required to achieve a specified reduction in bacterial cell number (microbial death or killing)).

A MIC test may also be used for characterization of the antimicrobial effects of the peptides of the present invention. This test determines growth inhibition by measuring the minimal inhibitory concentration (MIC) that inhibits microbial growth. It is usually performed in microtiter assay systems and determines cell viability. The MIC, however, does not distinguish between growth-arresting (bacteriostatic) and killing (bactericidal) activity. Most of the antibiotics in use are bacteriostatic and only a few are bactericidal.

The antimicrobial peptide of the present invention preferably has a minimal bactericidal concentration to kill 100% ($MBC_{100}$) of *P. aeruginosa* test strain ATCC10145 (or *Staphylococcus aureus* ATCC 6538) at pH 5.5 in nutrient-deficient 10 mM sodium phosphate buffer with 0.25% glucose, as measured by the microdilution assay and counting colony-forming units (CFU-assay; Steinberg and Lehrer, 1997, *Methods Mol Biol* 78, 169-186), of less than 1 µM, preferably less than 200 nM, more preferably less than 50 nM, and most preferably less than 10 nM. The minimal bactericidal concentration of the antimicrobial peptide of the present invention to kill 90% ($MBC_{90}$) of *P. aeruginosa* test strain ATCC10145 (or *Staphylococcus aureus* ATCC 6538) at pH 5.5 in nutrient-deficient 10 mM sodium phosphate buffer with 0.25% glucose, as measured by the CFU-assay, is preferably less than 100 nM, more preferably less than 30 nM, particularly preferably less than 10 nM, and most preferably less than 5 nM.

Several bactericidal broad-spectrum antibiotics like aminoglycosides, which have been extensively used for the treatment of Gram-negative and Gram-positive bacterial infections, have the disadvantage to be inherently toxic (ototoxicity and nephrotoxicity) upon long term use. Reduced target affinity caused by ribosomal modification, and decrease in their cellular concentration by efflux pumps leading to resistance towards aminoglycosides is another disadvantage which results in the emergence of resistant bacterial strains. Therefore, alternative bactericidal antimicrobials which have low, if any, cytotoxic properties, and are highly active against various pathogens, in particular against multi-drug-resistant Gram-negative bacteria like *P. aeruginosa, A. baumannii* and the *B. cepacia* complex, which is of highest relevance in cystic fibrosis, are urgently needed. The CIDAMPs of the present invention are highly activity against i.a. Gram-negative bacteria, having very low cytotoxic properties, thus presenting a solution for this problem.

Advantageously, the 50% cytotoxic concentration ($CC_{50}$) of the antimicrobial peptide of the present invention is usually ≥5 µM, preferably ≥20 µM, more preferably ≥50 µM, and most preferably ≥100 µM, as measured using normal human keratinocytes as test cells in accordance with the method described in Example 17.

The $CC_{50}/MBC_{90}$ ratio of the antimicrobial peptide of the present invention for *P. aeruginosa* is usually ≥150, preferably ≥300, more preferably ≥1000, and most preferably ≥3000, and/or the $CC_{50}/MBC_{90}$ ratio for *S. aureus* is usually ≥30, preferably ≥50, more preferably ≥100, and most preferably ≥300.

Surprisingly, the inventors of the present invention found that the novel CIDAMPs, unlike known amphipatic antimicrobial peptides, do not target the bacterial membrane, but the microbial ribosome with subsequent microbicidal effect. More specifically, it was unexpectedly found that the antimicrobial peptides of the present invention generally have the capacity of binding to prokaryotic ribosomes, in particular the capacity of binding to prokaryotic ribosomal proteins such as the 50S ribosomal proteins L13 and/or L22. Therefore, without being bound by theory, it is assumed that the observed antimicrobial activity of the peptides of the present invention is mediated, at least in part, by binding to prokaryotic ribosomal proteins.

Specific examples of the antimicrobial peptides of the present invention include the peptides having an amino acid sequence as shown in the attached Sequence Listing as SEQ ID NOs: 1 to 130. Particularly preferred antimicrobial peptides include those having an amino acid sequence as shown in Table 29, corresponding to SEQ ID NOs: 1 to 23.

Furthermore, the present invention also relates to antimicrobial peptides having a sequence identity of at least 80%, 84%, 88%, 92%, 95% or 98% to the amino acid sequence shown in one of SEQ ID NOs: 1 to 130, particularly one of SEQ ID NOs: 1 to 23.

For the purpose of the present invention, the "sequence identity" of two related amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. This is, the "changes" of two (optimally aligned) amino acid sequences are selected from amino acid substitutions, deletions or insertions, or a combination thereof.

The alignment of the two sequences can be performed as known to those skilled in the art, for example by the Needleman and Wunsch algorithm implemented in the EMBOSS software package (Rice et al. (2000), EMBOSS: the European Molecular Biology Open Software Suite, Trends. Genet. 16:276-277) to find optimum alignment over the entire length of the sequences, using default settings.

Furthermore, antimicrobial peptides within the scope of the present invention also include those having one, two, three, four or five of said changes (i.e. amino acid substitutions, deletions or insertions, or a combination thereof), particularly three or two changes and more particularly one change, compared to any one of the amino acid sequence shown in one of SEQ ID NOs: 1 to 130, particularly one of SEQ ID NOs: 1 to 23. Preferably, the number of said changes does not exceed 20%, 18%, 16%, 14%, 12%, 10%, 8% or 6% of all amino acids of any one of the amino acid sequence shown in one of SEQ ID NOs: 1 to 130, particularly one of SEQ ID NOs: 1 to 23. The "changes" of two related amino acid sequences refer to positions in the two optimally aligned sequences which have non-identical residues and/or a gap (i.e. a position in an alignment where a residue is present in one sequence but not in the other and which is regarded as a position with non-identical residues).

The changes (i.e. substitutions, deletions and/or insertions) may be at the N-terminal end, the C-terminal end or within the amino acid sequence. Furthermore, the changes may be at neighboring positions or non-neighboring positions or both. In a preferred embodiment, the amino acid substitution(s) and/or insertion(s) are selected from (a), (b), (c), (d), (e), (j), and (k) mentioned in connection with the method according to another aspect described below.

As mentioned above, the antimicrobial peptides of the present invention, in particular the antimicrobial peptides of SEQ ID NOs: 1 to 130 and related peptides described above, may optionally contain non-amino acid moieties and, in particular, may be N-palmitoylated, S-palmitoylated, 0-palmitoylated, N-myristoylated, or any combination thereof. Furthermore, the antimicrobial peptides may be modified as described below in connection with (f) and (g) of the method according to another aspect of the present invention.

In another aspect, the present invention provides a method of increasing antimicrobial activity and/or chemical stability and/or decreasing cytotoxic activity of an inventive antimicrobial peptide as described herein, wherein the method comprises one or more of the following steps:

(a) replacing one or more His by Arg (see Example 1),
(b) replacing one or more L-amino acids by the corresponding D-amino acid or vice versa (see Example 4),
(c) replacing one or more amino acids that are either neutral or negatively charged at pH 7.0 by one or more amino acids that are positively charged at pH 7.0 (see Example 6),
(d) replacing one or more amino acids by an amino acid where the α-amino group is replaced by an α-hydroxy group.
(e) adding the N-terminal sequence Gly-X-His (ATCUN-motif), where X can be any amino acid,
(f) adding at the N-terminus an N-palmitoylated Gly or any other N-palmitoylated amino acid or at the C-terminus an S-palmitoyl-Cys-amide (see Examples 5 and 7),
(g) adding at any position within the peptide an O-palmitoyl-Ser, an O-palmitoyl-Thr or any other O-palmitoyl-group-containing amino acid (see Examples 5 and 7),
(h) adding any anionic detergent, particularly rhamnolipids, to increase affinity to lipophilic skin surfaces (see Example 14),
(i) adding gluconate to increase solubility of CIDAMPs and their affinity to mucosal surfaces,
(j) replacing one, two, three or four amino acids by Cys, preferably for introducing a thiol-based high affinity zinc binding site,
(k) replacing one, two or three Cys by His, to generate His-based zinc-, manganese- or iron(II)-binding sites in the peptide.

According to the present invention, one or more amino acids of the antimicrobial peptide (CIDAMP) may be replaced by an amino acid where the α-amino group is replaced by an α-hydroxy group. The present invention thus includes depsipeptides. Depsipeptide-CIDAMPs may have the additional advantage of higher stability due to lower susceptibility to proteolysis. Furthermore, a mixture of different antimicrobial peptides of the present invention may increase potency and/or efficacy of antimicrobial activity in a synergistic manner (see Example 13).

It is known in the art that the addition of gluconate leads to increased peptide solubility and affinity towards mucosal surfaces (Davies et al., 1954, *Br. J. Pharmacol. Chemother.* 9, 192-6). Thus, according to the present invention, gluconate may be added to CIDAMPs in order to increase their solubility and affinity to mucosal surfaces.

In a further aspect, the present invention relates to a composition comprising at least one inventive antimicrobial peptide as described herein and a carrier.

The composition may be a pharmaceutical composition, in particular a topical pharmaceutical composition, or be in a form suitable for use as a cosmetic composition (topical or non-topical), as a disinfectant, an antiseptic, a preservative (e.g., a food preservative), an agent of biocontrol in food and agriculture, or an additive in animal feed. In one embodiment, only one antimicrobial peptide is present in the composition. The term "carrier", as used herein, describes an inert material with which the composition is mixed or formulated to facilitate its application, or its storage, transport and/or handling. The carrier can be solid (e.g., clays, silicates, silica, resins, sugars) or liquid (e.g., water, alcohols, ketones, aromatic and/or paraffinic hydrocarbons).

The form of the composition is not particularly limited and may include, but is not limited to, liquid dosage forms such as liquid dispersions, suspensions, solutions, emulsions, liposomes, sprays, spot-on, pour-on, gels, foams, propellant based or non-propellant based aerosols, ointments, creams, tinctures, mousses, or solid dosage forms such as powders, capsules (filled with powders, pellets, beads, mini-tablets, pills, micro-pellets, small tablet units, multi-unit pellet systems (MUPS), granules, microspheres, and/or multiparticulates), sachets (filled with powders, pellets, beads, mini-tablets, pills, micro-pellets, small tablet units, multi-unit pellet systems (MUPS), granules, microspheres, and/or multiparticulates) and sprinkles.

In a further aspect, the present invention provides a kit, comprising at least one antimicrobial peptide of the present invention and/or a composition of the present invention and, optionally, instructions for use.

The kit may comprise the antimicrobial peptide in the form of a lyophilized preparation, and may optionally comprise an aqueous solution for reconstitution. The kit may also comprise a liquid composition of the antimicrobial peptide. The instructions for use preferably prescribe that the intended use of the kit is for therapeutic use or use as a disinfectant, an antiseptic, a preservative (e.g., a food preservative), an agent of biocontrol in food and agriculture, or an additive in animal feed.

In a still further aspect, the present invention relates to an antimicrobial peptide or a mixture of antimicrobial peptides of the present invention for use as a medicament.

In particular, the antimicrobial peptide according to the present invention is suitable for use in the prevention and/or treatment of bacterial infections caused by at least one bacterial species selected from the group consisting of *Staphylococcus* spp. (e.g., *Staphylococcus aureus*), *Streptococcus* spp. (e.g., *Streptococcus pneumoniae*), *Burkholderia* spp. (e.g., *Burkholderia cepacia*), *Pseudomonas* spp. (e.g., *Pseudomonas aeruginosa*), *Escherichia* spp. (e.g., *Escherichia coli*), *Klebsiella* spp. (e.g., *Klebsiella pneumoniae*), *Propionibacterium* spp. (e.g., *Propionibacterium acnes*), *Prevotella* spp. (e.g., *Prevotella oralis*), *Clostridium* spp. (e.g., *Clostridium perfringens*), *Corynebacterium* spp. (e.g., *Corynebacterium simulans*), *Salmonella* spp. (e.g., *Salmonella typhimurium*), *Acinetobacter* spp. (e.g., *Acinetobacter baumanii*), and *Paenibacillus* spp. (e.g. *Paenibacillus larvae*).

Furthermore, the antimicrobial peptide according to the present invention is also suitable for use in the prevention and/or treatment of fungal infections, in particular fungal infections caused by yeasts (e.g., *Candida albicans, Cryptococcus neoformans*), filamentous fungi such as dermatophytes (e.g., *Malassezia* spp.), or *Aspergillus* ssp. (e.g., *Aspergillus fumigatus*).

Non-limiting examples of indications that can be suitably treated with the antimicrobial peptide of the present invention include skin infections in atopic dermatitis, acne and burn wounds, ulcera in psoriasis, aero-digestive-tract infections including cystic fibrosis, pneumonia, sinusitis, oral *Candida* ssp. infections, caries, chronic obstructive pulmonary disease, infections of the eye including *Pseudomonas*-keratitis of the cornea and its prophylaxis, otitis, vaginal infections (e.g., by *Candida* spp.), genito-urinary tract infections, inflammatory bowel diseases, infections by *Cryptococcus neoformans*, e.g., pulmonary cryptococcosis and cryptococcal meningitis, mastitis in cattle, or infections by *Paenibacillus larvae* causing American foulbrood in honey bees.

It is pointed out that the antimicrobial peptide of the present invention is equally usable for the therapy and/or prophylaxis of diseases and/or syndromes with similar genesis in both human and other animals, in particular in domestic and useful animals. Examples of such animals are dogs, cats, horses, camels, cattle or pigs without objective restriction. The term "treatment" or "therapy", as used herein, generally includes the curing of a disease or malfunction of the body and covers prophylactic treatment, unless otherwise stated.

Antimicrobial peptides of the present invention generated from intrinsically disordered protein precursors like hornerin, filaggrin-2 or LCE (Late Cornified Envelope), which are primarily found at body surfaces may be particularly suitable for the protection of body surfaces from microbial infection. Therefore, these peptides might be predestinated to protect body surfaces, such as the skin, aero-digestive-tract epithelia, genito-urinary tract epithelia and the eye, from infections by various microbes. The use of a particular peptide will depend on the microbe's sensitivity, the body location, the pH and the influence of nutrients and salt concentrations on the peptide's activity.

It is further contemplated that the antimicrobial peptides described herein are modified to, for example, increase the specific binding to the targeted microorganism, to block inhibitory plasma proteins and to optimize the uptake of the peptides, e.g. by using hybrid-CIDAMPs containing uptake-facilitating structures such as biotin.

It is further expected that changes in the amino acid composition or derivatization of the antimicrobial peptides allow for the generation of microbial target-selective antibiotics, which are able to eradicate the most challenging pathogens like *Pseudomonas aeruginosa, Klebsiella pneumoniae, Staphylococcus aureus* (MRSA), *Burkholderia cepacia* complex, *Acinetobacter baumannii, Escherichia coli, Streptococcus pneumoniae, Salmonella typhimurium* as well as fungi like *Cryptococcus neoformans* and *Candida albicans*, and are non-toxic for the host. In this respect, it is referred to the Examples which describe the generation of potent and efficient target-selective CIDAMPs, which are useful as topical anti-infectives and may also have the potential as systemically applied antibiotics.

In yet another aspect, the present invention relates to the use of an antimicrobial peptide of the present invention in cosmetic applications (e.g. as preservative in cosmetic products such as personal care products, and in anti-aging therapy, i.e. to counteract the aging process of the skin).

Furthermore, the present invention relates to the use of an antimicrobial peptide of the present invention as a disinfectant (e.g., in contact lens solutions or dental hygiene products or for coating implantable medical devices), antiseptic, preservative (e.g. food or feed preservative, or as preservative in cosmetic preparations), agent of biocontrol in food and agriculture, or additive in animal feed.

The term "disinfectant", as used herein, is intended to refer to antimicrobial agents that are applied to the surface of non-living objects to destroy microorganisms that are living on the objects. This is an important use of the antimicrobial peptides described herein since environmental contamination plays an important role in the transmission of several key health care-associated pathogens including methicillin-resistant *Staphylococcus aureus* (MRSA), vancomycin-resistant *Enterococcus* (VRE), *Acinetobacter*, and *Clostridium difficile*.

All these pathogens have been demonstrated to persist in the environment for hours to days (in some cases months), to frequently contaminate the environmental surfaces in rooms of colonized or infected patients, to transiently colonize the hands of health care personnel, to be transmitted by health care personnel, and to cause outbreaks in which environmental transmission was considered to play a role.

Furthermore, admission to a room in which the previous patient had been colonized or infected with MRSA, VRE, *Acinetobacter*, or *C. difficile* has been shown to be a risk factor for the newly admitted patient to develop colonization or infection. Efficient and safe environmental disinfection represents a major challenge in the face of the persistence of such pathogens.

Many substances used as low-level disinfectant have disadvantages such as being irritating, toxic, corrosive or flammable. Thus, it would be a significant progress in the art to have new disinfectants available for long lasting surface disinfection that is highly potent, killing a broad spectrum of microorganisms and, at the same time, is not toxic for humans or animals. This is achieved by the antimicrobial peptides of the present invention (CIDAMPs), which are optimized natural skin-disinfectants mimicking lipopeptide antibiotics and represent stable broad-spectrum bactericidal agents.

The term "antiseptic(s)", as used herein, broadly refers to antimicrobial substances that are applied to living tissue/skin to reduce the possibility of infection, sepsis, or putrefaction. The antimicrobial peptide of the present invention is suitable for use as commensal microbiota sparing, broad-spectrum antiseptic of skin- and mucosal surfaces. Such antiseptics with broad-spectrum anti-infective activity and low resistance potential offer an attractive option in both infection control and prevention.

There is evidence of benefit of antiseptics in a variety of clinical settings that include dental and oral hygiene, dermatology, oncology, and pulmonology, where they are extensively used in both prophylaxis and treatment of skin and wound infections, thus minimizing the use of antibiotics. The high rates of antibiotic misuse and subsequent development of bacterial resistance (e.g. increasing vancomycin-resistant Enterococci (VRE) and methicillin-resistant *Staphylococcus aureus* (MRSA)) in large parts of the world highlight the need for identifying alternative antimicrobials that would minimize the use of these medications. This further underlines the importance of an increasing armamentarium for infection prevention and control.

Furthermore, whereas, for example, in nosocomial rhinosinusitis or cystic fibrosis *P. aeruginosa* can be the major infecting agent, in atopic dermatitis *S. aureus* is the principal pathogen. Since local, especially long-term treatment with broad-spectrum antiseptics may generate resistant pathogens and also damages the local microflora, which is essential for local immune-homeostasis and health, antiseptics with bactericidal or bacteriostatic properties with very low potential for resistance development would be superior to broad spectrum antiseptics. The antimicrobial peptides (CIDAMPs) of the present invention can be used as such antiseptics.

The term "preservative", as used herein, generally refers to a substance or a chemical that is added to products such as food, beverages, pharmaceutical drugs, paints, biological samples, cosmetics, wood, and many other products to prevent decomposition by microbial growth or by undesirable chemical changes. Preferably, the preservative is a preservative in food for human use or in feed for animal use.

Food preservation, quality maintenance, and safety are major growing concerns of the food industry. It is evident that over time consumers' demand for natural and safe food products with stringent regulations to prevent food-borne infectious diseases are increasing. Antimicrobial packaging which is thought to be a subset of active packaging and controlled release packaging is one such promising technology which effectively impregnates the antimicrobial into the food packaging film material and subsequently delivers it over the stipulated period of time to kill the pathogenic microorganisms affecting food products thereby significantly increasing their shelf life. Consumers dislike organic acids as preservatives and prefer natural products for food preservation, e.g. antimicrobial peptides like lysozyme, lactoferrin or the microcin nisin. All these antimicrobial peptide preservatives are narrow-spectrum antimicrobials, which have a limited antimicrobial action, have mainly bacteriostatic properties, are active against Gram-positive bacteria only, need micromolar concentrations for effective inhibition and have limited activity against fungi.

Therefore, there is a need for further food preserving agents, which are of proteinaceous structure, act at nanomolar concentrations, are stable, non-toxic and inexpensive in their production. The present invention also provides low molecular weight CIDAMPs that preferentially limit growth of Gram-negative bacteria (e.g. *Salmonella typhimurium*), Gram-positive bacteria (e.g. *Listeria monocytogenes, Clostridium perfringens*) or fungi (*Aspergillus* spp.). Such CIDAMPs could represent alternatives to the currently used antimicrobial peptides for food preservation, because they can have selective antimicrobial activity, are bactericidal at nanomolar concentration, are not or very moderately cytotoxic and can be produced inexpensively.

With respect to the use of the antimicrobial peptide of the present invention as agent of biocontrol in food and agriculture or additive in animal feed, it is pointed out that it has been common practice for decades in modern animal husbandry to use sub-therapeutic doses of antibiotics in food animal feeds to prevent diseases and to improve production and performance. In the meantime, concerns over the increasing emergence of antibiotic-resistant bacteria due to unreasonable use of antibiotics and the appearance of less new antibiotics have prompted efforts to develop alternatives to classical antibiotics.

The antimicrobial peptides of the present invention represent promising alternatives to the antibiotics currently used in animal husbandry, because they can have selective antimicrobial activity, are bactericidal at nanomolar concentration, are not or very moderately cytotoxic and can be produced inexpensively.

EXAMPLES

The present invention will now be further illustrated by the following, non-limiting examples.

Example 1: *P. aeruginosa*-Cidal Activity of CIDAMPs

Various peptides corresponding to repeat domains of hornerin (HR 1-11: HRNR 2606-2628; HR 1-17: HRNR 2656-2684 and HR 1-18: HRNR 2656-2677) were tested for *P. aeruginosa* ATCC 10145-cidal activity in 10 mM Na-phosphate buffer pH 5.5, containing 0.25% glucose by counting the numbers of colonies of surviving bacteria at serial, twofold dilutions from 300 µg/ml down to 19 ng/ml of each peptide (CFU-assay; Steinberg and Lehrer, 1997, *Methods Mol. Biol.* 78, 169-186). HR 1-11, HR 1-17 and HR 1-18 display the most potent antimicrobial activity, killing 90% of the inoculum (MBC90) at 9-32 nM (see Table 1 and FIG. 1).

TABLE 1

P. aeruginosa ATCC 10145-cidal Hornerin peptides at pH 5.0, 0.25% glucose

| Sequence | SEQ ID NO: | Name | MBC90 (µg/ml) | MBC100 (µg/ml) |
|---|---|---|---|---|
| HGSRSGQSSRGERHGSSSGSSSH | 53 | HR 1-11 | 0.075 | 2.35 |
| GRHGSGLGHSSSHGQHGSGS-GRSSSRGPY | 64 | HR 1-17 | 0.038 | 0.15 |
| GRHGSGLGHSSSHGQHGSGSGR | 2 | HR 1-18 | 0.038 | 0.15 |

HR 1-18 was tested in the presence of trypticase soybean broth (TSB), a commonly used component for testing antibiotic sensitivity, to assess the influence of a nutrient-containing medium. A dose-dependent inhibition of its antimicrobial activity was observed (see Table 2).

TABLE 2

Inhibition of P. aeruginosa ATCC 10145-cidal activity of HR 1-18 by TS

| Sequence | SEQ ID NO: | Name | MBC90 (µg/ml) | MBC100 (µg/ml) | Condition |
|---|---|---|---|---|---|
| GRHGSGLGHSSSHGQHGSGSGR | 2 | HR 1-18 | 0.038 | 0.15 | pH 5.5, 0.25% glucose |
| GRHGSGLGHSSSHGQHGSGSGR | 2 | HR 1-18 | 9.38 | 1.18 | pH 5.5, 0.25% glucose, 1% TSB |
| GRHGSGLGHSSSHGQHGSGSGR | 2 | HR 1-18 | 300 | 37.5 | pH 5.5, 0.25% glucose, 3% TSB |
| GRHGSGLGHSSSHGQHGSGSGR | 2 | HR 1-18 | >300 | >300 | pH 5.5, 0.25% glucose, 10% TSB |

Figure 3:
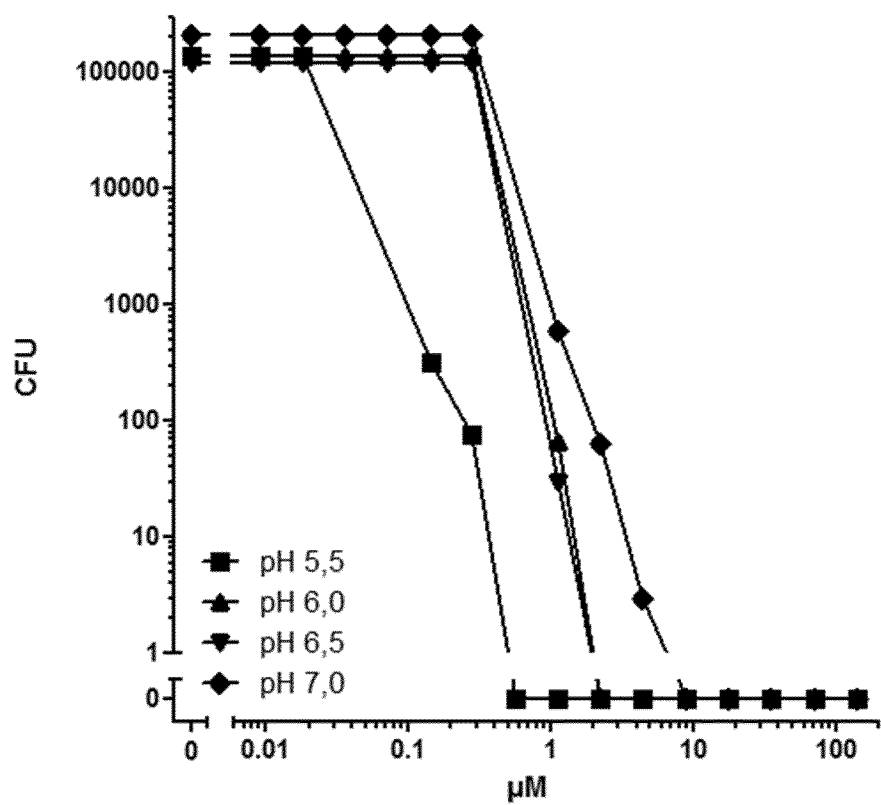
FIG. 3 shows the dependence of *P. aeruginosa* ATCC 10145-cidal activity of HR 1-18 4H-4R on pH.

*P. aeruginosa*-cidal activity of HR 1-18 is pH-dependent: compared to an incubation at pH 5.5, a two orders of magnitude drop in potency and efficacy was observed at pH 6.5 and antimicrobial activity was absent at pH 7.0 and 7.5. A HR 1-18 variant where all His have been replaced by Arg (HR 1-18 4H-4R) did not show a similar pH-dependency of *P. aeruginosa* ATCC 10145-cidal activity (see Table 3 and FIG. 3), which suggests that in this case the presence of His residues determines the pH-dependency. In HR 1-18, the loss of antimicrobial activity at pH 7.0 (at which His is not protonated, leading to the loss of positive charges of the peptide) arises from the high His content.

TABLE 3

Influence of pH on P. aeruginosa ATCC 10145 bactericidal activity of HR 1-18 and HR 1-18 4H-4R

| Sequence | SEQ ID NO: | Name | MBC90 (µg/ml) | MBC100 (µg/ml) | Condition |
|---|---|---|---|---|---|
| GRHGSGLGHSSSHGQHGSGSGR | 2 | HR 1-18 | 0.038 | 0.15 | pH 5.5, 0.25% glucose |
| GRHGSGLGHSSSHGQHGSGSGR | 2 | HR 1-18 | 2.35 | 18.75 | pH 6.0, 0.25% glucose |
| GRHGSGLGHSSSHGQHGSGSGR | 2 | HR 1-18 | 18.75 | >300 | pH 6.5, 0.25% glucose |
| GRHGSGLGHSSSHGQHGSGSGR | 2 | HR 1-18 | >300 | >300 | pH 7.0, 0.25% glucose |
| GRHGSGLGHSSSHGQHGSGSGR | 2 | HR 1-18 | >300 | >300 | pH 7.5, 0.25% glucose |
| GRRGSGLGRSSSRGGRGSGSGR | 4 | HR 1-18 4H-4R | 0.3 | 1.18 | pH 5.5, 0.25% glucose |
| GRRGSGLGRSSSRGGRGSGSGR | 4 | HR 1-18 4H-4R | 2.35 | 4.7 | pH 6.0, 0.25% glucose |
| GRRGSGLGRSSSRGGRGSGSGR | 4 | HR 1-18 4H-4R | 2.35 | 4.7 | pH 6.5, 0.25% glucose |
| GRRGSGLGRSSSRGGRGSGSGR | 4 | HR 1-18 4H-4R | 2.35 | 9.38 | pH 7.0, 0.25% glucose |

4H-4R: H replaced by R in HR 1-18

To investigate the structural requirements for bactericidal activity against *P. aeruginosa* ATCC 10145, mutants of HR 1-11, HR 1-17 and HR 1-18 were studied. Replacement of the N-terminal His or Arg in HR 1-11 by Gly has the strongest effects on both potency and efficacy of the peptide's *P. aeruginosa*-cidal activity (see Table 4). Less reduction of the potency was seen when the various central or C-terminal His or Arg were exchanged against Gly. Here a reduction of the potency of the peptide's bactericidal activity at pH 5.5 was approx. 10 to 30-fold, depending on the position of the exchange. Substitution of the single acidic amino acid Glu by Gly improved the potency nearly fourfold (see Table 4), showing that the net charge is important for antimicrobial activity.

TABLE 4

*P. aeruginosa* ATCC 10145-cidal activity of HR 1-11 peptides

| Sequence | SEQ ID NO: | Name | MBC90 (µg/ml) | MBC100 (µg/ml) | Condition |
|---|---|---|---|---|---|
| HGSRSGQSSRGERHGSSSGSSSH | 53 | HR 1-11 | 0.075 | 2.35 | pH 5.5, 0.25% glucose |
| HGSRSGQSSRGERHGSSSGSSSH | 53 | HR 1-11 | 2.35 | >300 | pH 5.5, 1% TSB |
| HGSGSGQSSRGERHGSSSGSSSH | 59 | HR 1-11 R1-G R2609G | >300* | >300* | pH 5.5, 1% TSB |
| HGSRSGQSSGGERHGSSSGSSSH | 60 | HR 1-11 R2-G R2615G | 75 | >300 | pH 5.5, 1% TSB |
| HGSRSGQSSGGGRHGSSSGSSSH | 55 | HR 1-11 E-G E2617G | 0.59 | >300 | pH 5.5, 1% TSB |
| HGSRSGQSSRGEGHGSSSGSSSH | 61 | HR 1-11 R3-G R2618G | 75 | >300 | pH 5.5, 1% TSB |
| GGSRSGQSSRGERHGSSSGSSSH | 56 | HR 1-11 H1-G H2606G | >300* | >300* | pH 5.5, 1% TSB |
| HGSRSGQSSRGERGGSSSGSSSH | 57 | HR 1-11 H2-G H2619G | 75 | >300 | pH 5.5, 1% TSB |
| HGSRSGQSSRGERHGSSSGSSSG | 58 | HR 1-11 H3-G H2628G | 18.75 | >300 | pH 5.5, 1% TSB |
| RGSRSGQSSRGERRGSSSGSSSR | 54 | HR 1-11 3H3R | 0.3 | 9.375* | pH 5.5, 0.25% glucose |
| RGSRSGQSSRGERR | 62 | HR 1-11s 2H2R-14 | 0.15 | 4.7 | pH 5.5, 0.25% glucose |

*antimicrobial paradox (increased bacteria growth with increasing CIDAMP-concentrations)

The importance of positive charges was further shown in mutants of HR 1-17 and HR 1-18. Substitution of a single Arg against Gly in HR 1-17, which contains three Arg and four His residues, did not change the microbicidal concentration killing 100% of the bacteria (MBC100) and the MBC90, in 10 mM Na-phosphate pH 5.5 with 0.25% glucose (see Table 5). In contrast, substitution of all four His residues against Gly led to a reduced bactericidal activity with a nearly 2,000-fold increase of the MBC90 (see Table 5 and FIG. 1).

TABLE 5

*P. aeruginosa* ATCC 10145-cidal activity of HR 1-17 peptides at pH 5.0, 0.25% glucose

| Sequence | SEQ ID NO: | Name | MBC90 (µg/ml) | MBC100 (µg/ml) |
|---|---|---|---|---|
| GRHGSGLGHSSSHGQHGSGSGRSSSRGPY | 64 | HR 1-17 | 0.0375 | 0.15 |
| GGHGSGLGHSSSHGQHGSGSGRSSSRGPY | 65 | HR 1-17 R2657G | 0.0375 | 0.3 |
| GRHGSGLGHSSSHGQHGSGSGGSSSRGPY | 66 | HR 1-17 R2677G | 0.0375 | 0.15 |
| GRHGSGLGHSSSHGQHGSGSGRSSSGGPY | 67 | HR 1-17 R2681G | 0.0375 | 0.15-0.3 |
| GRGGSGLGGSSSGGQGGSGSGRSSSRGPY | 68 | HR 1-17 4H-4G all H vs G | 75 | >300 |

Figure 8:
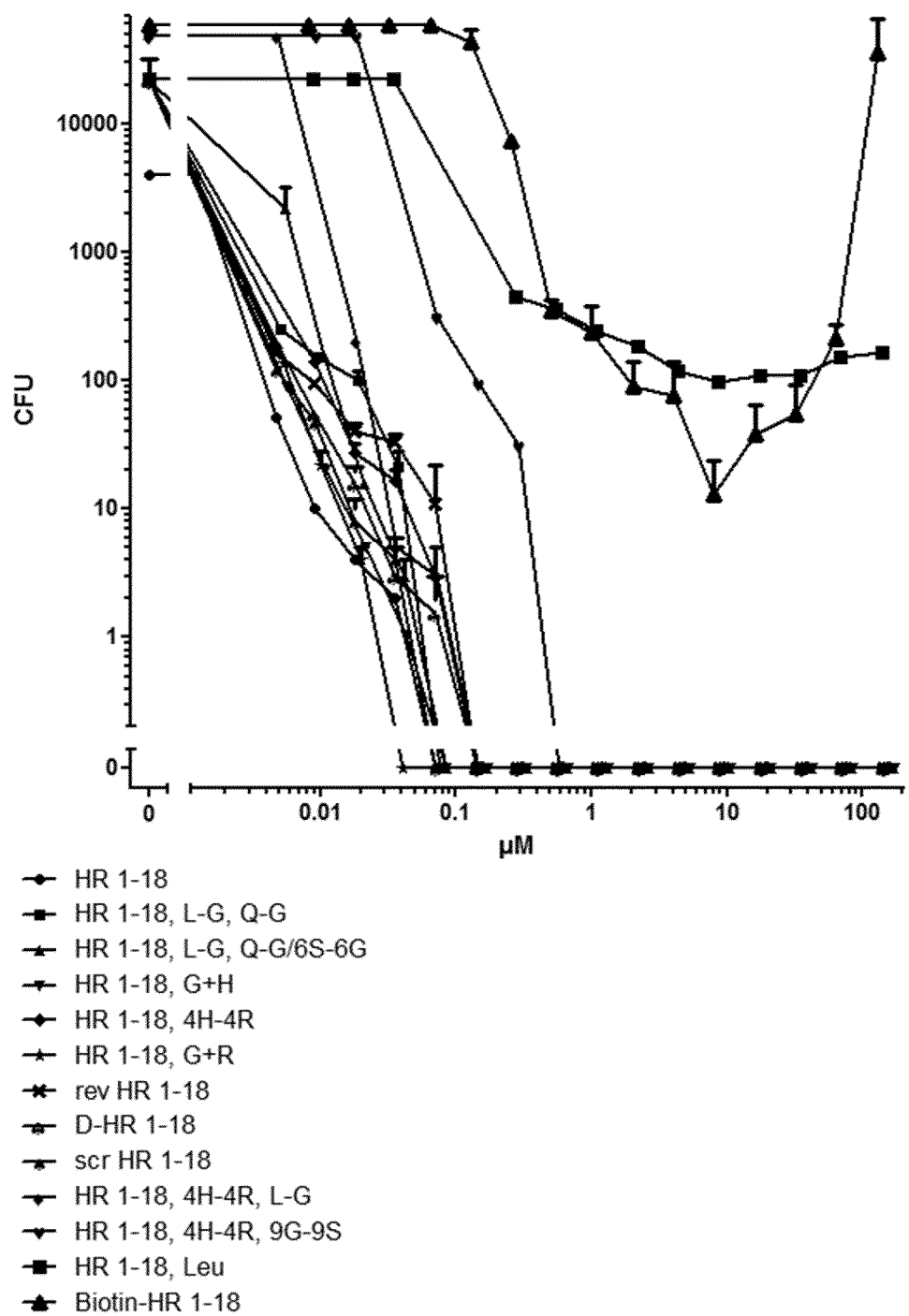
FIG. 8 shows the *P. aeruginosa* ATCC 10145-cidal activity of HR 1-18 peptides.

HR 1-18 mutants, where the single Leu and Gln residues had been replaced by Gly displayed similar MB91 and MBC100 as wild-type (WT) HR 1-18. In addition, the substitution of all six Ser against Gly also did not affect MBC90 and MBC100 (see Table 6 and FIG. 8). A further HR 1-18 variant, where the Arg residues had been replaced by His, and all other amino acids by Gly, generating the 22-mer peptide HR 1-18 G+H, showed a MBC90<0.019 µg/ml and a MBC100 of 0.075 µg/ml when tested in 10 mM Na-phosphate, pH 5.5 and 0.25% glucose (see Table 6 and FIG. 8).

TABLE 6

*P. aeruginosa* ATCC 10145-cidal activity of HR 1-18 peptides at pH 5.0, 0.25% glucose

| Sequence | SEQ ID NO: | Name | MBC90 (µg/ml) | MBC100 (µg/ml) |
|---|---|---|---|---|
| GRHGSGLGHSSSHGQHGSGSGR | 2 | HR 1-18 | 0.038 | 0.15 |
| GRHGSGGGHSSSHGGHGSGSGR | 71 | HR 1-18 L-G/Q-G | 0.038 | 0.15 |
| GRHGGGGHGGGHGGHGGGGGR | 72 | HR 1-18 L-G/Q-G/6S-6G | 0.038 | 0.15 |
| GHHGGGGHGGGHGGHGGGGH | 73 | HR 1-18 G + H | <0.006 | 0.09 |
| GRRGSGLGRSSSRGGRGSGSGR | 4 | HR 1-18 4H-4R | 0.038 | 0.15 |
| GRRGGGGRGGGRGGRGGGGGR | 74 | HR 1-18 GR | <0.019 | 0.075 |
| RGSGSGHQGHSSSHGLGSGHRG | 122 | revHR 1-18 | <0.019 | 0.075 |
| SLSSGHGSGHGHQRGGHRSGSG | 124 | scrHR 1-18 | <0.019 | 0.075 |
| GRRGSGGGRSSSRGGRGSGSGR | 70 | HR 1-18 4H-4R/L-G | 0.038 | 0.15 |
| SRRSSSLSRSSSRSSRSSSSSR | 69 | HR 1-18 4H-4R/9G-9S | 0.15 | 1.18 |
| LRHGSGLGHSSSHGQHGSGSGR | 76 | HR 1-18 G2656L | 4.7 | >300 |
| Biotin-GRHGSGLGHSSSHGQHGSGSGR | 24 | Biotin-HR 1-18 | >300/1.18* | >300 |
| FITC-GRHGSGLGHSSSHGQHGSGSGR | 30 | FITC-HR 1-18 | 0.15 | 1.18 |

Figure 2:
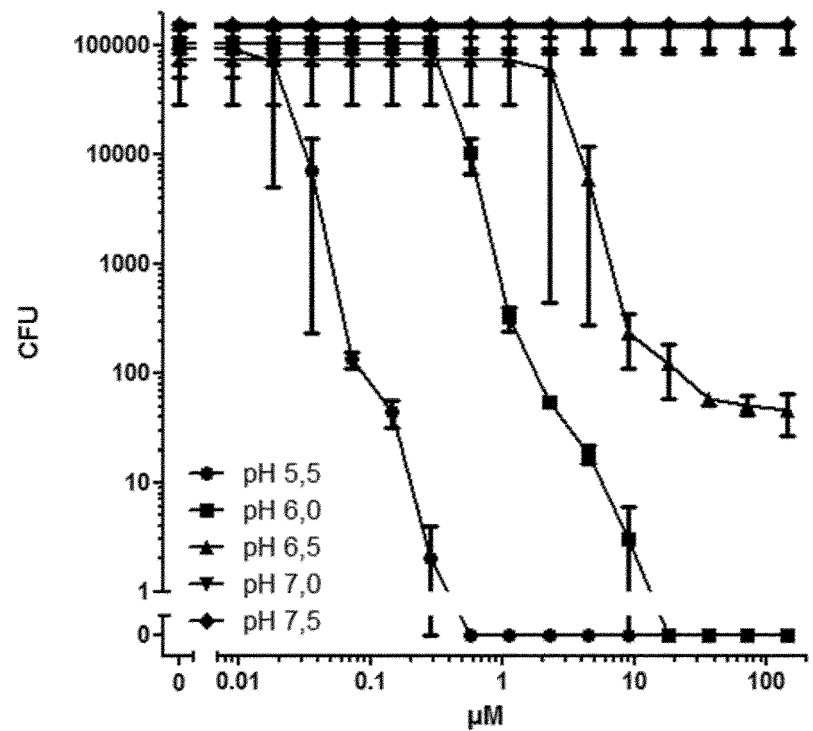
FIG. 2 shows the dependence of *P. aeruginosa* ATCC 10145-cidal activity of HR 1-18 on pH.

*antimicrobial paradox (increased bacterial growth with increasing CIDAMP-concentrations)
FITC = fluorescein isothiocyanate As expected from Table 3 and FIG. 2, HR 1-18 G+H and other His-rich HR 1-18-variants did not show *P. aeruginosa*-cidal activity at pH 7.0 (see Table 7).

To test the hypothesis that not the amino acid sequence but the composition is important for bactericidal activity, two HR 1-18 variants with identical composition were tested: a mutant with the reversed amino acid sequence (revHR 1-18) and another mutant with a scrambled amino acid sequence (scrHR 1-18). In addition, the effect of D-amino acids on the activity of HR 1-18 was investigated (data not shown). All these HR 1-18 variants display MBC90 and MBC100 values for *P. aeruginosa* ATCC 10145 similar to the original HR 1-18 (see Table 6 and FIG. 8), supporting the notion that the amino acid composition, but not the amino acid sequence is important for *P. aeruginosa* ATCC 10145-cidal activity.

Many of the investigated peptides are rich in His and are active at pH 5.5, but not at pH 7.0. To test, whether replacing His by Arg reconstitutes *P. aeruginosa*-cidal activity at pH 7.0, a variant of HR 1-18 where all four His were substituted by Arg was used. In 10 mM Na-phosphate and 0.25% glucose this HR 1-18 4H-4R-peptide had a MBC90 of 0.038 µg/ml and a MBC100 of 0.15 µg/ml at pH 5.5, and a MBC90 of 2.38 µg/ml and a MBC100 at 9.38 µg/ml at pH 7.0. A further HR 1-18 variant, where all His were substituted by Arg, and all other amino acids were substituted by Gly, generating the 22-mer peptide HR 1-18 GR, had a MBC90<0.019 µg/ml and a MBC100 at 0.075 µg/ml at pH 5.5 (see Table 6 and FIG. 8). In contrast to HR 1-18 G+H, HR 1-18 GR is bactericidal at pH 7.0 with a MBC90 at 0.59 µg/ml and a MBC100 at 4.8 µg/ml (see Table 7).

TABLE 7

*P. aeruginosa* ATCC 10145-cidal activity of HR 1-18 peptides at pH 7.0, 0.25% glucose

| Sequence | SEQ ID NO: | Name | MBC90 (µg/ml) | MBC100 (µg/ml) |
|---|---|---|---|---|
| GRHGSGLGHSSSHGQHGSGSGR | 2 | HR 1-18 | >300 | >300 |
| GRHGSGGGHSSSHGGHGSGSGR | 71 | HR 1-18 L-G/Q-G | >300 | >300 |

TABLE 7-continued

*P. aeruginosa* ATCC 10145-cidal activity of HR 1-18 peptides at pH 7.0, 0.25% glucose

| Sequence | SEQ ID NO: | Name | MBC90 (µg/ml) | MBC100 (µg/ml) |
|---|---|---|---|---|
| GRHGGGGHGGGHGGHGGGGGR | 72 | HR 1-18 L-G/Q-G/6S-6G | >300 | >300 |
| GHHGGGGHGGGHGGHGGGGGH | 73 | HR 1-18 G + H | >300 | >300 |
| GRRGSGLGRSSSRGGRGSGSGR | 4 | HR 1-18 4H-4R | 2.35 | 9.38 |
| GRRGGGGGRGGGRGGRGGGGGR | 74 | HR 1-18 GR | 0.59/150* | 4.7-75, >300* |

*antimicrobial paradox (increased bacterial growth with increasing CIDAMP-concentrations).

All these observations indicate that the composition, but not the sequence determines the antimicrobial activity of CIDAMPs. To further support this hypothesis, CIDAMPs of various origins and different amino acid composition were studied in terms of pH-dependent antimicrobial properties.

Several proteins expressed in the cornified envelope of human epidermis are intrinsically disordered proteins or rich in "Intrinsically Disordered Protein Regions" (IDPRs). Hornerin (HRNR), filaggrin-2 (FLG-2), repetin (RPT), filaggrin (FLG) and "late cornified envelope proteins" (LCEs) represent, among others, characteristic cationic IDPs within the epidermal differentiation complex. The data shown in Tables 1-7 suggest that cationic amino acids are important for bactericidal activity.

To test the hypothesis that intrinsically disordered peptides (IDPs) with a net positive charge are *P. aeruginosa* ATCC 10145-cidal, a number of selected IDPR were selected, corresponding to defined, cationic amino acid-containing parts of different repeat domains in these proteins. These peptides are rich in Gly, Ser, Thr and/or Gln, and have low contents of hydrophobic amino acids like Val, Leu, Phe, Tyr, Trp, Cys and a low content of acidic amino acids like Glu or Asp. All contain His and/or Arg and/or Lys.

Figure 4:
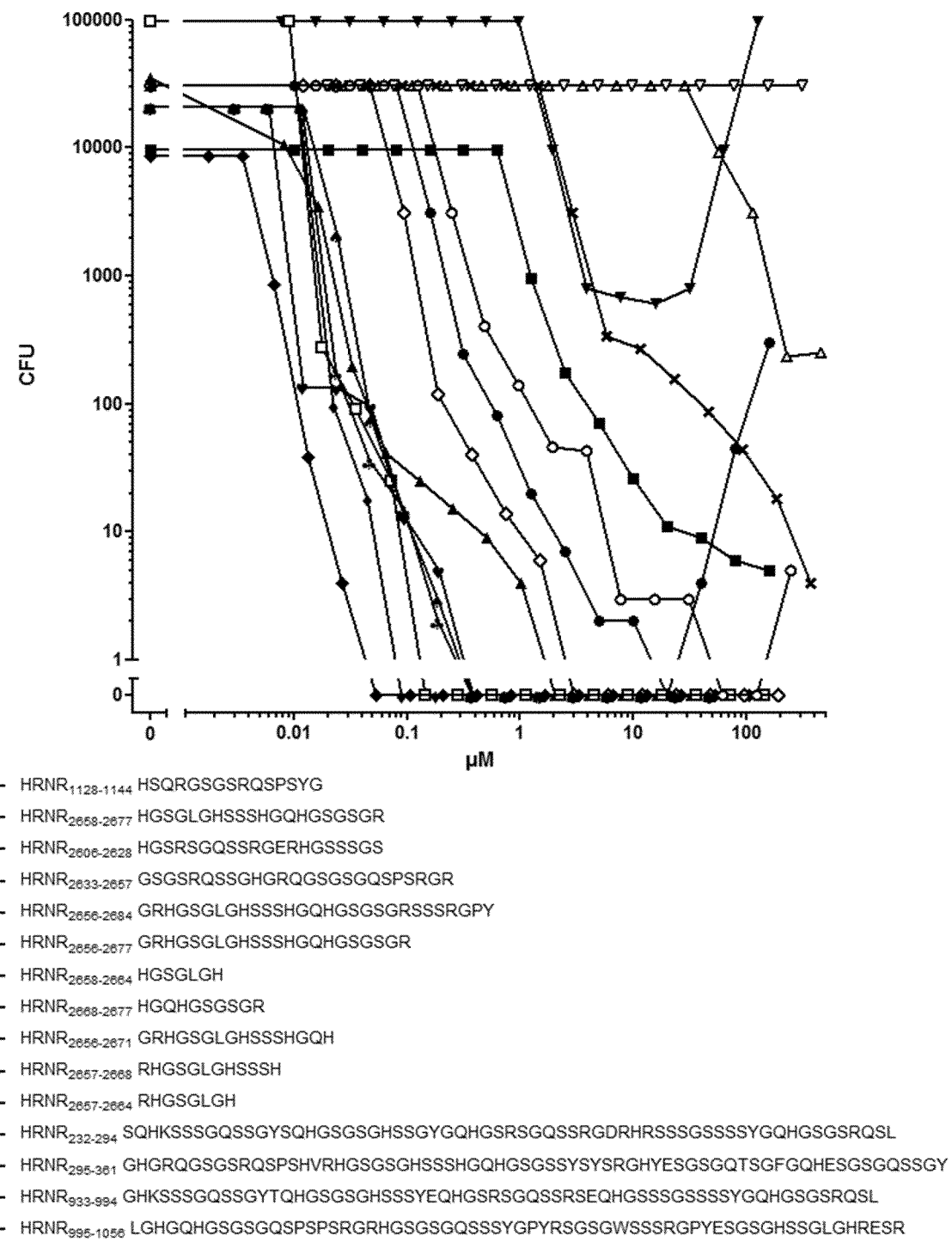
FIG. 4 shows the *P. aeruginosa* ATCC 10145-cidal activity of hornerin peptides (from top to bottom, the listing of sequences have SEQ ID NOS: 88, 84, 131, 132, 64, 2, 133, 134, 77, 79, 135, 98, 101, 102 and 103, respectively)
Figure 5:
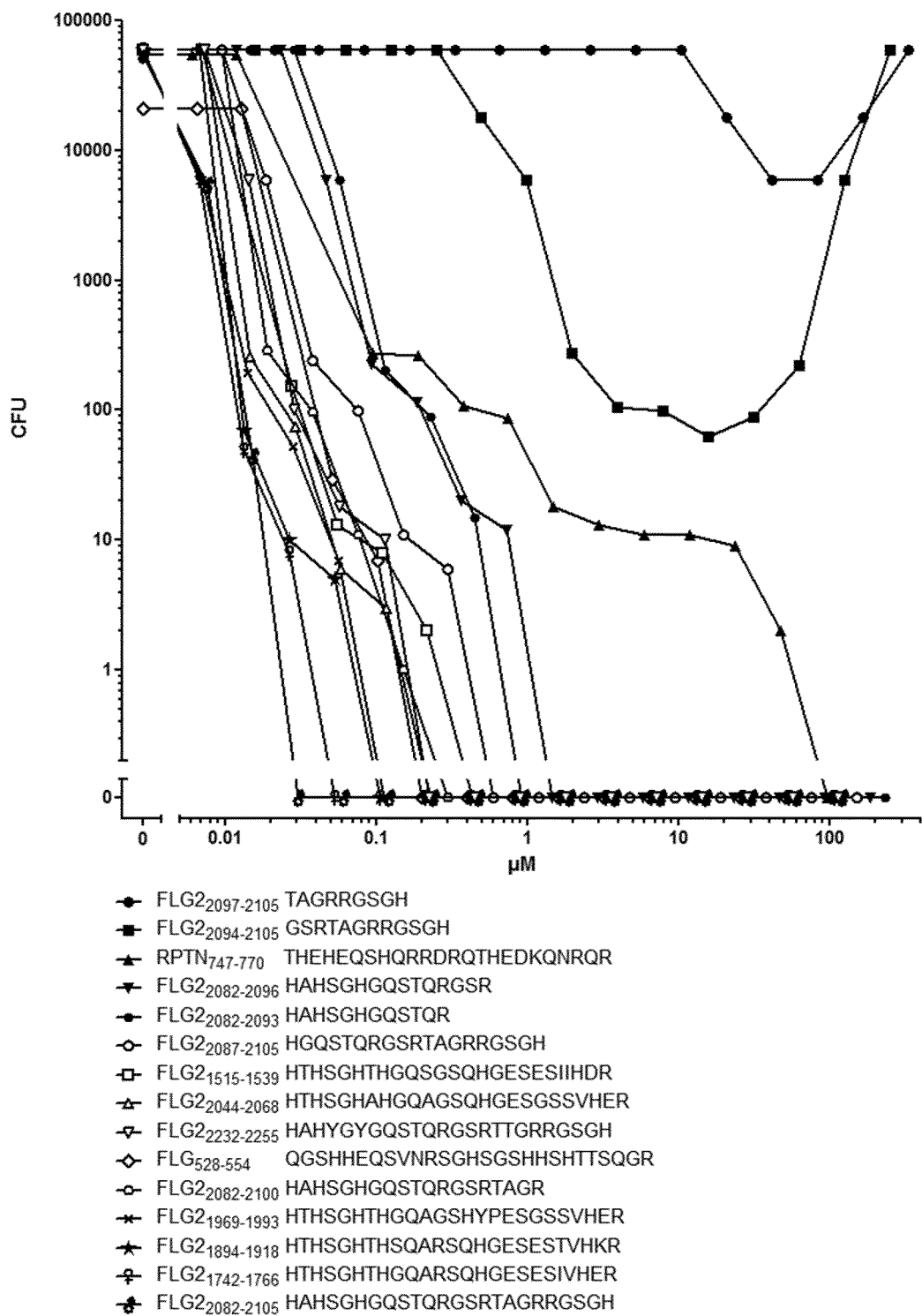
FIG. 5 shows the *P. aeruginosa* ATCC 10145-cidal activity of filaggrin-2- and repetin-CIDAMPs (from top to bottom, the listing of sequences have SEQ ID NOS: 47, 40, 123, 37, 36, 39, 31, 35, 42, 43, 1, 34, 33, 32 and 38, respectively)

As above, the selected IDPRs were tested in 10 mM Na-phosphate buffer pH 5.5, containing 0.25% glucose. The results on peptides of HRNR, FLG-2, RPTN and FLG show that at pH 5.5, *P. aeruginosa* ATCC 101 45-cidal activity is present when the net positive charge of the IDPs is >+3. In peptides with a net positive charge of +4, the MBC90 values were depending on composition and chain length—within a low nM range to a low µM range (see Table 8 and FIGS. 4-5). Whereas the tested peptides with a net positive charge ≥+5 and a peptide chain length of >19 amino acids show a MBC90 in the range of 10-100 nM, peptides with a net positive charge <+3 show very low bactericidal activity, if any (see FIG. 1 and FIGS. 4-5).

TABLE 8

*P. aeruginosa* ATCC 10145-cidal activity of various CIDAMPs

| Sequence | SEQ ID NO: | Name | MBC90 (µg/ml) | MBC100 (µg/ml) | Condition |
|---|---|---|---|---|---|
| GSGSRQSPSYGRHGSGSGRSSSSGQH | 85 | HR 2-11 HRNR$_{1132-1157}$ | 37.5 | >300 | pH 5.5, 1% TSB |
| RQSPSYGRHGSGSGR | 86 | HR 2-14 HRNR$_{1136-1150}$ | 300 | >300 | pH 5.5, 1% TSB |
| SRQSPSYGRHGSGR | 87 | HR 2-15 HRNR$_{1136-1150}$ S1148R | 75 | >300 | pH 5.5, 1% TSB |
| GSGSRQSSSYGRHGSGSGR | 93 | HR 2-4S HRNR$_{1132-1150}$ P1139S | 150 | >300 | pH 5.5, 1% TSB |
| GSGSRQSLSYGRHGSGSGR | 90 | HR 2-4L HRNR$_{1132-1150}$ P1139L | 75 | >300 | pH 5.5, 1% TSB |
| GSGSRQSPSRGRHGSGSGR | 92 | HR 2-4R HRNR$_{1132-1150}$ Y1141R | 37.5/300* | >300 | pH 5.5, 1% TSB |
| GSGSRQSPSHGRHGSGSGR | 89 | HR 2-4H HRNR$_{1132-1150}$ Y1141H | 75 | >300 | pH 5.5, 1% TSB |
| GSGSRQSPSYGRQGSGSGR | 91 | HR 2-4Q HRNR$_{1132-1150}$ H1144Q | >300 | >300 | pH 5.5, 1% TSB |
| HSQRGSGSRQSPSYGRH | 88 | HR 2-16 HRNR$_{1128-1144}$ | 0.59/300* | 37.5 (only at this conc.)* | pH 5.5, 0.25% glucose |
| HGSSSGSSSHYGQHGSGSR | 83 | HR 1-4 HRNR$_{2619-2637}$ | 150 | >300 | pH 5.5, 1% TSB |
| GSGSRQSSGHGRQGSGSGQ | 63 | HR 1-16 HRNR$_{2633-2651}$ | >300 | >300 | pH 5.5, 1% TSB |

TABLE 8-continued

*P. aeruginosa* ATCC 10145-cidal activity of various CIDAMPs

| Sequence | SEQ ID NO:Name | MBC90 (µg/ml) | MBC100 (µg/ml) | Condition |
|---|---|---|---|---|
| HGSGLGHSSSHGQHGSGSGR | 84  HR 1-8 HRNR$_{2658-2677}$ | 18.75 and >300* | >300 | pH 5.5, 1% TSB |
| HGSGLGHSSSHGQHGSGSGR | 84  HR 1-8 HRNR$_{2658-2677}$ | 4.7 | >300 | pH 5.5, 0.25% glucose |
| HGSRSGQSSRGERHGSSSGSSSH | 53  HR 1-11 | 0.075 | 2.35 | pH 5.5, 0.25% glucose |
| GRHGSGLGHSSSHGQHGSGSGRSSSRGPY | 64  HR 1-17 | 0.038 | 0.15 | pH 5.5, 0.25% glucose |
| GRHGSGLGHSSSHGQHGSGSGR | 2  HR 1-18 | 0.038 | 0.15 | pH 5.5, 0.25% glucose |
| GRHGSGLGHSSSHGQH | 77  HR 1-25 HRNR$_{2656-2671}$ | 0.3 | 4.7 | pH 5.5, 1% TSB |
| RHGSGLGHSSSHGQH | 78  HR 1-26 HRNR$_{2657-2671}$ | 0.3/150* | 4.7-75* | pH 5.5, 0.25% glucose |
| RHGSGLGHSSSH | 79  HR 1-27 HRNR$_{2657-2668}$ | 75-100* | 1.18/300* | pH 5.5, 0.25% glucose |
| LGHSSSHGQHGSGSGRSSSRGPYESRLGH | 80  HR 1-36 HRNR$_{2663-2690}$ | 0.15 | 2.35 | pH 5.5, 0.25% glucose |
| GRHGSGLGHSSSH | 81  HR 1-37 HRNR$_{2656-2668}$ | 9.38 | >300 | pH 5.5, 0.25% glucose |
| HSSSHGQHGSGSGR | 82  HR 1-38 HRNR$_{2664-2677}$ | >300/9.38* | >300 | pH 5.5, 0.25% glucose |
| GRHGSGSGQSSSYGPYRSGSGWSSSRGPY | 95  HRNR$_{1013-1041}$ | 1.18/75* | >300 | pH 5.5, 1% TSB |
| GRHGSGSGQSSSYGPYGSGSGWSSSRGPY | 96  HRNR$_{1952-1980}$ | 18.75/150* | >300 | pH 5.5, 1% TSB |
| GRHGSGSGQSSSYSPYGSGSGWSSSRGPY | 100  HRNR$_{2422-2450}$ | 2.35/>300* | >300 | pH 5.5, 1% TSB |
| GRHGSGSGHSSSHGQHGSGSGR | 97  HRNR$_{2186-2207}$ | 0.15/75* | 4.7-9.37* | pH 5.5, 0.25% glucose |
| GRHGSGSGQSSSYSPYGSGSGWSSSR | 99  HRNR$_{2422-2447}$ | 18.75/150* | >300 | pH 5.5, 0.25% glucose |
| SQHKSSSGQSSGYSQHGSGSGHSSGYGQHGSRSGQSSRGDRHRSSSGSSSSYGQHGSGSRQSL | 98  HRNR$_{232-294}$ | 0.30 | 2.35 | pH 5.5, 0.25% glucose |
| GHGRQGSGSRQSPSHVRHGSGSGHSSSHGQHGSGSSYSYSRGHYESGSGQTSGFGQHESGSGQSSGY | 101  HRNR$_{295-361}$ | 0.15 | 0.59 | pH 5.5, 0.25% glucose |
| GHKSSSGQSSGYTQHGSGSGHSSSYEQHGSRSGQSSRSEQHGSSSGSSSSYGQHGSGSRQSL | 102  HRNR$_{933-994}$ | 0.3 | 2.35 | pH 5.5, 0.25% glucose |
| LGHGQHGSGSGQSPSPSRGRHGSGSGQSSSYGPYRSGSGWSSSRGPYESGSGHSSGLGHRER | 103  HRNR$_{995-1056}$ | 0.3 | 2.35 | pH 5.5, 0.25% glucose |
| QGSHHEQSVNRSGHSGSHHSHTTSQGR | 43  FLG$_{528-554}$ | 0.15 | 0.59 | pH 5.5, 0.25% glucose |
| HAHSGHGQSTQRGSRTAGRRGSGH | 38  FLG-2$_{2082-2105}$ | <0.075 | 0.038 | pH 5.5, 0.25% glucose |
| HAHSGHGQSTQRGSRTAGR | 1  FLG-2$_{2082-2100}$ | 0.038 | 0.3 | pH 5.5, 0.25% glucose |
| HTHSGHTHGQSGSQHGESESIIHDR | 31  FLG-2$_{1515-1539}$ | 0.075 | 0.59 | pH 5.5, 0.25% glucose |

TABLE 8-continued

P. aeruginosa ATCC 10145-cidal activity of various CIDAMPs

| Sequence | SEQ ID NO:Name | | MBC90 (µg/ml) | MBC100 (µg/ml) | Condition |
|---|---|---|---|---|---|
| HTHSGHTHGQARSQHGESESIVHER | 32 | FLG-2$_{1742-1766}$ | 0.038 | 0.15 | pH 5.5, 0.25% glucose |
| HTHSGHTHSQARSQHGESESTVHKR | 33 | FLG-2$_{1894-1918}$ | 0.038 | 0.3 | pH 5.5, 0.25% glucose |
| HTHSGHTHGQAGSHYPESGSSVHER | 34 | FLG-2$_{1969-1993}$ | 0.038 | 0.3 | pH 5.5, 0.25% glucose |
| HTHSGHAHGQAGSQHGESGSSVHER | 35 | FLG-2$_{2044-2068}$ | 0.038 | 0.3 | pH 5.5, 0.25% glucose |
| HAHSGHGQSTQR | 36 | FLG-2$_{2082-2093}$ | 0.15 | 2.35 | pH 5.5, 0.25% glucose |
| HAHSGHGQSTQRGSR | 37 | FLG-2$_{2082-2096}$ | 0.15 | 1.18 | pH 5.5, 0.25% glucose |
| HGQSTQRGSRTAGRRGSGH | 39 | FLG-2$_{2087-2105}$ | 0.075 | 1.18 | pH 5.5, 0.25% glucose |
| GSRTAGRRGSGH | 40 | FLG-2$_{2094-2105}$ | >300/2.35* | >300 | pH 5.5, 0.25% glucose |
| TAGRRGSGH | 41 | FLG-2$_{2097-2105}$ | >300 | >300 | pH 5.5, 0.25% glucose |
| HAHYGYGQSTQRGSRTTGRRGSGH | 42 | FLG-2$_{2232-2255}$ | 0.075 | 0.59 | pH 5.5, 0.25% glucose |
| THEHEQSHQRRDRQTHEDKQNRQR | 123 | RPTN$_{747-770}$ | 0.3 | 150 | pH 5.5, 0.25% glucose |

*antimicrobial paradox (increased bacterial growth with increasing CIDAMP-concentrations)

In view of the above, it can be said that the bactericidal action on P. aeruginosa ATCC 10145 primarily depends on the number of positively charged amino acids, and also on the peptide chain length. It seems that a net positive charge of +3 or higher at the pH conditions of the microbial environment is necessary for P. aeruginosa ATCC 10145-killing activity of CIDAMPs.

Figure 6:
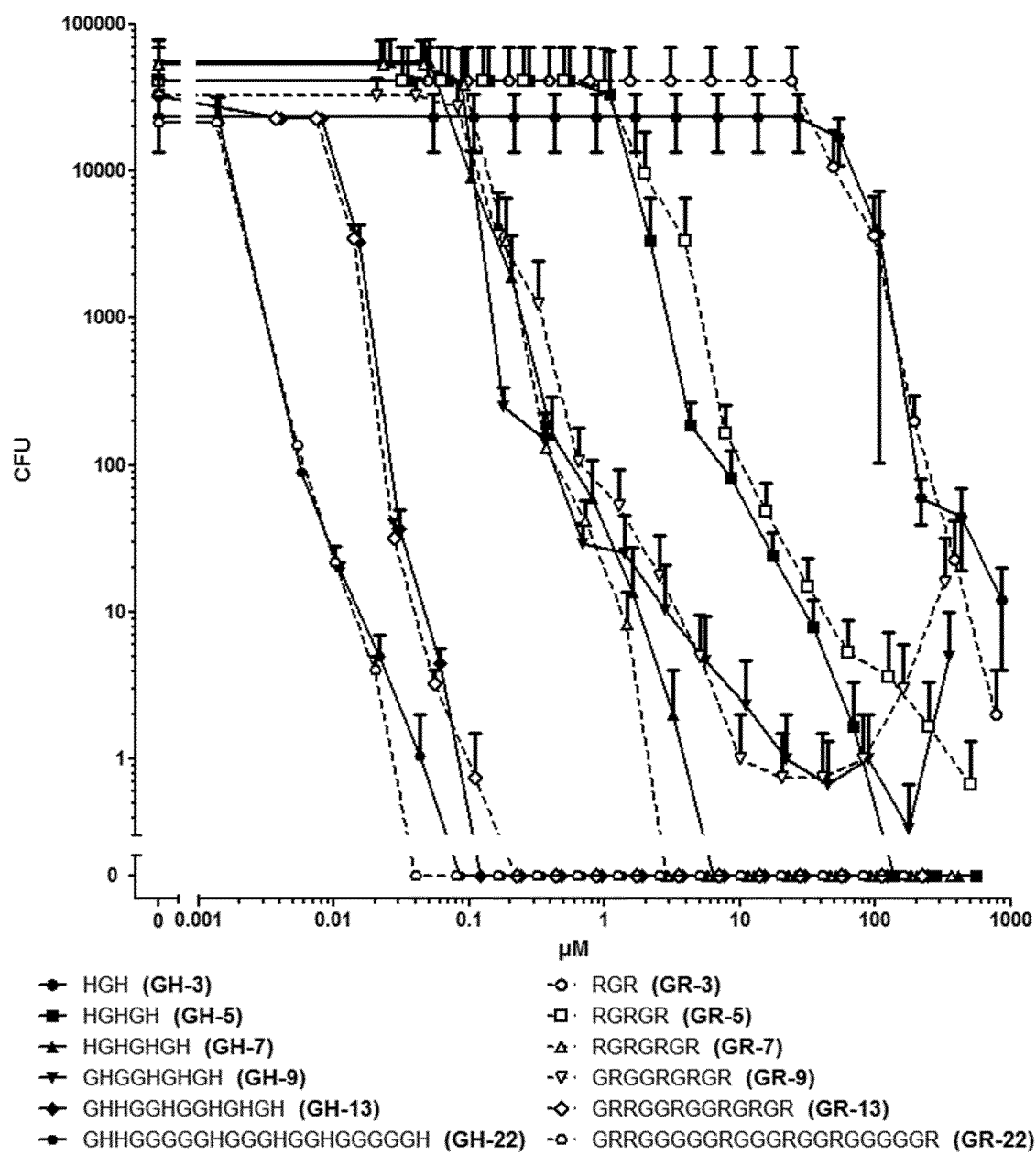
FIG. 6 shows the *P. aeruginosa* ATCC 10145-cidal activity of Gly-His- and Gly-Arg-peptides of increasing chain length (from left to right and top to bottom, the listing of sequences have SEQ ID NOS: 45, 46, 47, 48, 44, 73, 49, 50, 57, 52, 17 and 74, respectively)

To further study the influence of the peptide length, CIDAMPs of variable chain lengths consisting only of Gly and Arg, or Gly and His were tested for P. aeruginosa ATCC 10145-cidal activity at pH 5.5. Surprisingly, already tripeptides, consisting in two His and one Gly or two Arg and one Gly, were active with an MBC90 of 200 µM. An increase in chain length, continuously to 13 residues, was unexpectedly found to decrease the MBC90 from 6 µM for the penta-peptide, 250 nM for the hepta-peptide, 200 nM for the nona-peptide, to 30 nM for the trideca-peptide. A further increase of the peptide chain length decreased the MBC90 further, down to below 10 nM (see Table 9 and FIG. 6).

TABLE 9

P. aeruginosa-cidal activity of Gly/His- and Gly/Arg-peptides at pH 5.5, 0.25% glucose

| Sequence | SEQ ID NO: | Name | MBC90 (µM) | MBC100 (µM) |
|---|---|---|---|---|
| HGH | 45 | GH3 | 200 | >860 |
| RGR | 49 | GR3 | 150 | >930 |
| HGHGH | 46 | GH5 | 6.0 | 138 |
| RGRGR | 50 | GR5 | 6.1 | >500 |
| HGHGHGH | 47 | GH7 | 0.25 | 7.2 |
| RGRGRGR | 51 | GR7 | 0.31 | 2.8 |
| HGHGHGHGH | 48 | GH9 | 0.18 | >400, MBC99: 99 |
| RGRGRGRGR | 52 | GR9 | 0.22 | >400, MBC99: 10.2 |

TABLE 9-continued

P. aeruginosa-cidal activity of Gly/His- and Gly/Arg-peptides at pH 5.5, 0.25% glucose

| Sequence | SEQ ID NO: | Name | MBC90 (µM) | MBC100 (µM) |
|---|---|---|---|---|
| GHHGGHGGHGHGH | 44 | GH13 | 0.030 | 0.12 |
| GRRGGRGGRGRGR | 17 | GR13 | 0.028 | 0.055 |
| GHHGGGGHGGGHGGHGGGGGH | 73 | HR 1-18 G + H | <0.006 | 0.09 |
| GRRGGGGRGGGRGGRGGGGGR | 74 | HR 1-18 GR | <0.006 | 0.04 |

Figure 7:
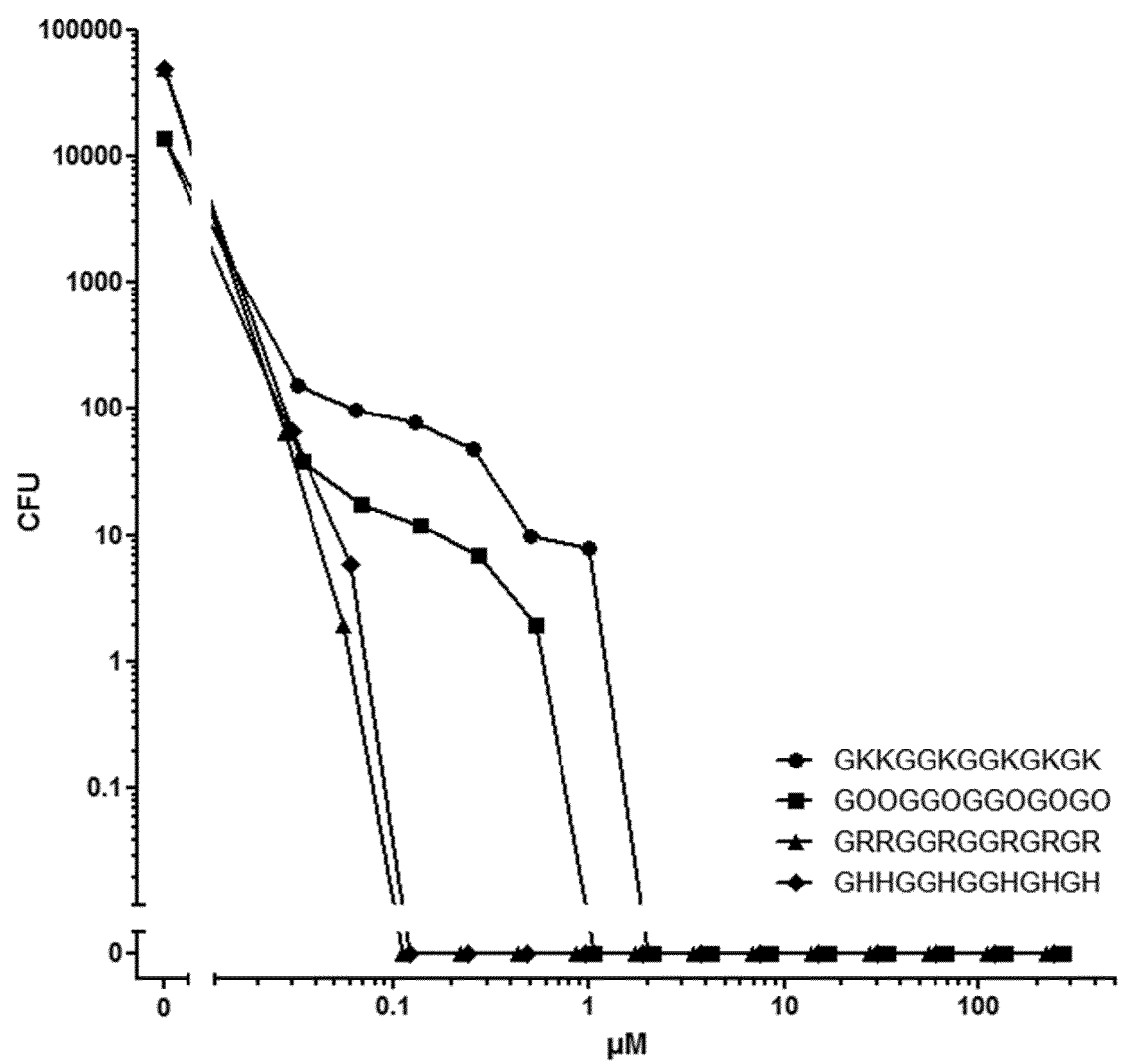
FIG. 7 shows the *P. aeruginosa* ATCC 10145-cidal activity of 13mer Gly-CIDAMPs with Lys, Orn, Arg or His as cationic amino acids (from top to bottom, the listing of sequences have SEQ ID NOS: 104, 114, 17 and 44, respectively)

All CIDAMPs mentioned thus far contain as basic amino acids only Arg and/or His. Tests using 13-mer IDPs containing Gly and the basic amino acids His, Arg, Lys or ornithine (Orn) showed that all peptides were bactericidal for *P. aeruginosa* ATCC 10145 with an MBC90 in the range of 28-63 nM (see Table 10 and FIG. 7), suggesting that the presence of positively charged residues—independent from their molecular structure—is important for *P. aeruginosa*-cidal activity.

TABLE 10

P. aeruginosa-cidal activity of Gly-rich 13-mer peptides containing Lys, Orn, Arg and His at pH 5.5, 0.25% glucose

| Sequence | Name | SEQ ID NO: | MBC90 (µM) | MBC100 (µM) |
|---|---|---|---|---|
| GKKGGKGGKGKGKK | GR13 | 104 | 0.063 | 2.0 |
| GOOGGOGGOGOGOGO Orn | GR13 | 114 | 0.034 | 1.1 |
| GRRGGRGGRGRGR | GR13 | 17 | 0.028 | 0.055 |
| GHHGGHGGHGHGH | GH13 | 44 | 0.030 | 0.12 |

It should be noted that some CIDAMPs showed an abnormal dose-response curve with an unusual increase of bacterial survival at increasing concentrations (see, e.g., Table 4 and Tables 6-8). This phenomenon, termed "paradoxical effect" (Taylor et al., 1983, *Antimicrob. Agents. Chemother.* 23, 142-50), seems to be more likely CIDAMP-specific (see FIGS. 4-5) than microbe-specific, suggesting that unique physicochemical parameters such as formation of supramolecular complexes forming precipitates (which may lead to too low concentrations of monomeric CIDAMPs) determine this property.

In summary, the results show that a potent and efficient *P. aeruginosa*-cidal CIDAMP consists, for example, of about 13 or more IDP-characteristic residues, such as Gly, together with about 4 or more basic amino acids, such as Arg or any other positively charged amino acid. A high content of Arg or of other amino acids cationic at pH 7.0 and a high percentage of His will make such CIDAMPs more active at acidic pH conditions than at pH 7.0.

Example 2: Antimicrobial Activity Spectrum of HR 1-17 and HR 1-18

HR 1-17 and HR 1-18 activity against a number of microorganisms is shown in Tables 11-12. These peptides do not show any antimicrobial activity for all strains of tested Gram-positive bacteria (*Staphylococcus aureus, Streptococcus pneumonia, Streptococcus pyogenes*), except *Enterococcus faecium* DSM 2146. In addition, some strains of Gram-negative bacteria (*Escherichia coli, Proteus mirabilis, Burkholderia cepacia*) were also not killed at concentrations <300 µg/ml (in 10 mM Na-phosphate buffer pH 5.5, containing 0.25% glucose). *Acinetobacter baumannii* ATCC 19606 was killed by HR 1-18 (MBC90: 0.56 µM).

TABLE 11

Antimicrobial activity spectrum of HR 1-18

| Microbe | MBC90 (µg/ml) | MBC100 (µg/ml) | Conditions |
|---|---|---|---|
| *Staphylococcus aureus* ATCC 6538 | >300 | >300 | pH 5.5, 1% TSB |
| *Streptococcus pneumoniae* ATCC 33400 | >300 | >300 | pH 6.5, 0.25% glucose |
| *Enterococcus. faecium* DSM 2146 | 150 | >300 | pH 5.5, 0.25% glucose |
| *Streptococcus pyogenes* ATCC 12344 | >300 | >300 | pH 6.0, 0.25% glucose |
| *Pseudomonas aeruginosa* ATCC10145 | 0.038 | 0.15 | pH 5.5, 0.25% glucose |
| *Pseudomonas aeruginosa* ATCC10145 | 0.15 | 2.35 | pH 5.5, 1% TSB |
| *Acinetobacter baumannii* ATCC 19606 | 1.18 | 37.5 | pH 6.0, 0.25% glucose |

TABLE 11-continued

Antimicrobial activity spectrum of HR 1-18

| Microbe | MBC90 (µg/ml) | MBC100 (µg/ml) | Conditions |
|---|---|---|---|
| Escherichia coli ATCC11775 | >300 | >300 | pH 5.5, 1% TSB |
| Proteus mirabilis ATCC 21100 | >300 | >300 | pH 6.0, 0.25% glucose |
| Candida albicans ATCC 24433 | 18.8 | 150 | pH 5.5, 0.25% glucose |
| Candida albicans ATCC 24433 | 150 | >300 | pH 5.5, 1% TSB |
| Burkholderia cepacia ATCC 25416 | >300 | >300 | pH 5.5, 0.25% glucose |

TABLE 12

Antimicrobial activity spectrum of HR 1-17

| Microbe | MBC90 (µg/ml) | MBC100 (µg/ml) | Conditions |
|---|---|---|---|
| Staphylococcus aureus ATCC 6538 | >300 | >300 | pH 5.5, 1% TSB |
| Pseudomonas aeruginosa ATCC10145 | 0.075 | 0.3 | pH 5.5, 0.25% glucose |
| Pseudomonas aeruginosa ATCC10145 | 0.59 | 18.75 | pH 5.5, 1% TSB |
| Escherichia coli ATCC11775 | >300 | >300 | pH 5.5, 1% TSB |
| Candida albicans ATCC 24433 | 1.18 | 9.38 | pH 5.5, 0.25% glucose |
| Candida albicans ATCC 24433 | 18.8 | 150 | pH 5.5, 1% TSB |
| Burkholderia cepacia ATCC 25416 | >300 | >300 | pH 5.5, 0.25% glucose |

Example 3: *Staphylococcus aureus*-Cidal Activity of CIDAMPs

*Staphylococcus aureus* is a major skin pathogen, which causes skin infections, in particular in atopic dermatitis. The sensitivity of *S. aureus* ATCC 6538 towards several CIDAMPs was assessed using the CFU-assay as above (see Example 1). HR 1-18, which lacks *S. aureus*.-bactericidal activity, is converted in a *S. aureus*-cidal peptide, when all His are replaced by Arg (HR 1-18 4H-4R; see Table 13 and FIG. 9). Interestingly, at pH 7.0 this peptide was more potent (MBC90: 9.35 ug/ml) than at pH 5.5 (MBC90: 150 µg/ml). Substitution of the nine Gly by Ser made this peptide less potent at pH 7.0, but it retained *S. aureus*-cidal activity at pH 5.5. HR 1-18 4H-4R is rich in Ser and Arg and contains a single Leu residue. When this single Leu was replaced by Gly in *S. aureus*-cidal HR 1-18 4H-4R (forming HR 1-18 4H-4R/L-G), *S. aureus*-cidal activity was abolished at both pH 7.0 and pH 5.5 (see Table 13 and FIG. 9). This suggests an important role of hydrophobic amino acids in *S. aureus*-bactericidal CIDAMPs.

TABLE 13

*S. aureus* ATCC 6538-cidal activity of various CIDAMPs

| Sequence | SEQ ID NO: | Name | MBC90 (µg/ml) | MBC100 (µg/ml) | Condition |
|---|---|---|---|---|---|
| GRHGSGLGHSSSHGQHGSGSGR | 2 | HR 1-18 | >300 | >300 | pH 5.5, 0.25% glucose |
| LRHGSGLGHSSSHGQHGSGSGR | 76 | HR 1-18 G2656L | 300 | >300 | pH 5.5, 0.25% glucose |
| GRRGSGLGRSSSRGGRGSGSGR | 4 | HR 1-18 4H-4R | 150 | >300 | pH 5.5, 0.25% glucose |
| GRRGSGLGRSSSRGGRGSGSGR | 4 | HR 1-18 4H-4R | 9.375 | >300 max.killing: 98.8% | pH 7.0, 0.25% glucose |
| GRRGSGGGRSSSRGGRGSGSGR | 70 | HR 1-18 4H-4R/L-G | >300 | >300 | pH 5.5, 0.25% glucose |
| GRRGGGGGRGGGRGGRGGGGR | 74 | HR 1-18 GR | >300 | >300 | pH 5.5, 0.25% glucose |
| SRRSSSLSRSSSRSSRSSSSSR | 69 | HR 1-18 4H-4R/9G-9S | 150 | >300 | pH 5.5, 0.25% glucose |
| SRRSSSLSRSSSRSSRSSSSSR | 69 | HR 1-18 4H-4R/9G-9S | 75 | >300 | pH 7.2, 0.25% glucose |
| GRRGGRGGRGRGR | 17 | GR13 | 75 | >300 | pH 5.5, 0.25% glucose |
| GRRGGRGGRGRGR | 17 | GR13 | 75 | >300 | pH 7.0, 0.25% glucose |

TABLE 13-continued

S. aureus ATCC 6538-cidal activity of various CIDAMPs

| Sequence | SEQ ID NO: | Name | MBC90 (µg/ml) | MBC100 (µg/ml) | Condition |
|---|---|---|---|---|---|
| SHHRPRLFHRRRH | 107 | LCE2B$_{74-86}$ | 1.18 | >150 max.killing: 97.4% | pH 5.5, 0.25% glucose |
| SHHRCCRSHRCRR | 20 | LCE3B$_{56-68}$ | 0.075 | >150 max.killing: 99.3% | pH 5.5, 0.25% glucose |
| SHHRHFRSHQCRR | 22 | LCE3C$_{55-67}$ | 2.35 | >150 max.killing: 97.7% | pH 5.5, 0.25% glucose |
| SHHRHFRSHQCRRQRSNSCDR | 110 | LCE3C$_{55-75}$ | 0.59 | >150 max.killing: 99.4% | pH 5.5, 0.25% glucose |
| FITC-GRHGSGLGHSSSHGQHGSGSGR | 30 | FITC-HR 1-18 | 300 | >300 | pH 5.5, 0.25% glucose |

FITC = fluorescein isothiocyanate

In order to verify the hypothesis that adding a long chain fatty acid acyl residue at the N-terminus of IDAMPs increases their antimicrobial activity, N-acylated CIDAMPs were investigated for S. aureus-cidal activity. All tested N-acylated CIDAMPs were active against S. aureus. Pal-GR13 was found to be the most potent and efficient (MB390: 50 nM) palmitoylated I-DAMP, killing 100% of the inoculum at 200 nM. N-terminally myristoylated CIDAMPs were also S. aureus-cidal, however less potent and efficient than the respective N-terminally palmitoylated CIDAMP (see Table 14 and FIG. 10).

TABLE 14

Effect of palmitoylation and myristoylation on S. aureus ATCC 6538-cidal activity

| Sequence | SEQ ID NO: | Name | MBC90) (µg/ml) | MBC100 (µg/ml) | Condition |
|---|---|---|---|---|---|
| Pal-GRHGSGLGHSSSHGQHGSGSGR | 3 | Pal-HR 1-18 | >300 | >300 | pH 7.3, 0.25% glucose |
| Pal-GRHGSGLGHSSSHGQHGSGSGR | 3 | Pal-HR 1-18 | 1.18 | 37.5 | pH 5.5, 0.25% glucose |
| Myr-GRHGSGLGHSSSHGQHGSGSGR | 112 | Myr-HR 1-18 | 9.38 | 75 | pH 5.5, 0.25% glucose |
| Myr-GRHGSGLGHSSSHGQHGSGSGR | 112 | Myr-HR 1-18 | 18.75 | 75 | pH 7.0, 0.25% glucose |
| Myr-GRRGSGLGRSSSRGQRGSGSGR | 113 | Myr-HR 1-18 HR | 18.75 | 75 | pH 7.3, 1% TSB |
| Pal-GRRGSGLGRSSSRGQRGSGSGR | 5 | Pal-HR 1-18 HR | 0.3 | 4.7 | pH 5.5, 0.25% glucose |
| Pal-GRRGSGLGRSSSRGQRGSGSGR | 5 | Pal-HR 1-18 HR | 1.18 | 9.38 | pH 7.3, 1% TSB |
| Pal-HGSRSGQSSRGERHGSSSGSSSH | 8 | Pal-HR 1-11 | 2.35 | >300 | pH 5.5, 0.25% glucose |
| Pal-RGSRSGQSSRGERRGSSSGSSSR | 10 | Pal-HR 1-11 3H3R | 0.59 | 300 | pH 5.5, 0.25% glucose |
| Pal-RGSRSGQSSRGERR | 9 | Pal-HR 1-11 2H2R-14 | 0.59/>300* | 18.75-75/>300* | pH 5.5, 0.25% glucose |
| Pal-GRRGGRGGRGRGR | 18 | Pal-GR13 | 0.3 | 4.7 | pH 5.5, 1% TSB |
| Pal-GRRGGRGGRGRGR | 18 | Pal-GR13 | 0.075 | 0.3 | pH 5.5, 0.25% glucose |
| Pal-GR$_D$R$_D$GGR$_D$GGR$_D$GR$_D$ | 19 | D-Pal-GR13 | 0.075 | 75, MBC99: 0.59 | pH 5.5, 0.25% glucose |
| Pal-GRRGGRGGRGR | 16 | Pal-GR11 | 0.3 | 75, MBC99: 1.18 | pH 5.5, 0.25% glucose |

TABLE 14-continued

Effect of palmitoylation and myristoylation on *S. aureus* ATCC 6538-cidal activity

| Sequence | SEQ ID NO: | Name | MBC90) (µg/ml) | MBC100 (µg/ml) | Condition |
|---|---|---|---|---|---|
| Pal-GRRGGRGGR | 15 | Pal-GR9 | 1.18 | 300, MBC99: 4.7 | pH 5.5, 0.25% glucose |
| Pal-GR$_D$R$_D$GGR$_D$GGR$_D$ | 29 | D-Pal-GR9 | 0.15 | 2.35 | pH 5.5, 0.25% glucose |
| Pal-GRRGGR | 14 | Pal-GR6 | 2.35 | 37.5, MBC99: 4.7 | pH 5.5, 0.25% glucose |
| Pal-GRGR | 13 | Pal-GR4 | 2.35 | 9.375, MBC99: 4.7 | pH 5.5, 0.25% glucose |
| Pal-GR$_D$GR$_D$ | 28 | D-Pal-GR4 | 18.75 | 37.5 | pH 5.5, 0.25% glucose |
| Pal-GKKGGKGGKGKGK | 118 | Pal-K-GR13 | 0.59 | >300 | pH 5.5, 0.25% glucose |
| Pal-GOOGGOGGOGOGO | 121 | Pal-Orn-GR13 | 0.15 | 18.75 | pH 5.5, 0.25% glucose |
| Pal-GKGK | 115 | Pal-GK4 | 4.7 | 9.375 | pH 5.5, 0.25% glucose |
| D-Pal-GK$_D$GK$_D$ | 26 | D-Pal-GK4 | 4.7 | 9.375 | pH 5.5, 0.25% glucose |
| Pal-GOGO | 116 | Pal-GOrn4 | 9.38 | 37.5 | pH 5.5, 0.25% glucose |
| D-Pal-GO$_D$GO$_D$ | 27 | D-Pal-GOrn4 | 9.38 | 18.75 | pH 5.5, 0.25% glucose |
| Pal-GDabGDab | 11 | Pal-GDab4 | 4.7 | 18.75 | pH 5.5, 0.25% glucose |
| Pal-GDapGDap | 12 | Pal-GDap4 | 2.35 | 4.7 | pH 5.5, 0.25% glucose |
| Pal-GRRGSGLGRSSSR | 6 | Pal-HR 1-18 3H3R-GR13 | 2.35 | 37.5 | pH 5.5, 0.25% glucose |
| Pal-SHHRCCRSHRCRR | 21 | Pal-LCE3B$_{56-68}$ | <0.019 | 0.15 | pH 5.5, 0.25% glucose |
| Pal-SHHRHFRSHQCRR | 23 | Pal-LCE3C$_{55-67}$ | 0.038 | 0.3 | pH 5.5, 0.25% glucose |
| Pal-SHHRHFRSHQCRRQRSN-SCDR | 120 | Pal-LCE3C$_{55-75}$ | 0.15 | 0.59 | pH 5.5, 0.25% glucose |

*antimicrobial paradox (increased bacterial growth with increasing CIDAMP-concentrations) MBC99: Concentration of peptide, which kills 99.0% of inoculum, determined in the CFU-assay O = Orn; Dab = (L)1,3-diaminobutyric acid; Dap = (L)1,3-diaminopropionic acid It was further found that synthetic, defined S-palmitoylated hornerin peptides are *S. aureus*-cidal (see Table 15). Since they show no cytotoxic activity (see FIG. 18), S-palmitoylated CIDAMPs could be useful in special situations, for example—due to the fact that S-palmitoylation is under enzymatic control (Hornemann, 2015, Inherit. Metab. Dis., 38, 179-86)—in a situation where action is only desired for a short-time period, which makes S-palmitoylated CIDAMPs also good candidates for use in situations where cell toxicity is a problem.

TABLE 15

S. aureus ATCC 6538-cidal activity of S-palmitoylated hornerin peptides at pH 5.5, 0.25% glucose

| Sequence | SEQ ID NO: | Name | MBC90 (µg/ml) | MBC100 (µg/ml) |
|---|---|---|---|---|
| GQHGSSSGHSSTHGQHGSTSGQSSSC-Pal* | 128 | S-Pal-HRNR$_{598-623}$ | 2.35 | >150 |
| Pal-CGQHGATSGQSSSHGQHGSGSSQSSR | 129 | S-Pal-HRNR$_{623-648}$ | 2.35 | >150 |
| Pal-CGQHGATSSGQSSSHGQHGSGSSQSSGYGR | 125 | S-Pal-HRNR$_{1089-1117}$ | >150 | >150 |
| GRHGSGSGQSSGFGHHESSSWQSSGC-Pal* | 126 | S-Pal-HRNR$_{1389-1414}$ | 1.18 | 18.8 |
| SGHSSVFGQHESGSGHSSAYSQHGSGSGHFC-Pal* | 127 | S-Pal-HRNR$_{1748-1778}$ | 0.3 | 9.38 |
| GQHGSSSGHSSTHGQHGSASGQSSSC-Pal* | 130 | S-Pal-HRNR$_{2004-2029}$ | 0.59 | >150/75** |

*amide
**antimicrobial paradox (increased bacterial growth with increasing CIDAMP-concentrations)

Overall, the above shows that palmitoylated Gly/Ser-rich positively charged CIDAMPs have the potential to be potent S. aureus-cidal peptides, additionally sparing the "good" commensal microflora. In addition, palmitoylated CIDAMPs may be designed to kill MRSA, also being active at pH 7.4 and in the presence of Mueller-Hinton medium, which is the commonly used standard medium for antibiotic sensitivity testing, outlined by the Clinical and Laboratory Standards Institute, and known to inhibit the activity of various antimicrobial peptides (Steinberg and Lehrer, 1997, *Methods Mol. Biol.*, 78, 169-86).

Furthermore, sensitivity of a methicillin-resistant *S. aureus* strain (ATCC 43300) was investigated for palmitoylated CIDAMPs in a microtiter plate screening model, with incubation in Mueller-Hinton medium at 37° C. for 18 h using resazurin as a marker for cell viability. Among those, three CIDAMPs (the 13-mer Pal-GR13, the 22-mer Pal-HR 1-18 HR and the 14-mer Pal-HR 1-11 2H2R-14) were identified to be able to kill this MRSA-strain at low µg/ml or high ng/ml concentration (see Table 29). Thus, these results show that palmitoylated CIDAMPs can be designed and optimized to have highest efficacy and potency against various MRSA strains.

Moreover, His- and Cys-rich peptides derived from the intrinsically disordered "Late Cornified Envelope *Proteins*" (LCEs), LCE2B$_{74-86}$, LCE3B$_{56-68}$, LCE3C$_{55-67}$ and LCE3C$_{55-75}$ were also studied in terms of *S. aureus*-cidal activity. The N-terminus of these peptides is a potential cleavage site of profilaggrin endoproteinase 1 (PEP1), a profilaggrin processing enzyme that cleaves peptides derived from insoluble profilaggrin (P1) at residues adjacent to a tyrosine sequence resulting in partial solubilization (Resing et al., 1995, *J. Biol. Chem.*, 270, 28193-8).

The C-terminus of these designed peptides is a potential tryptic cleavage site which might be used by several skin-derived tryptic enzymes such as KLK5 and KLK14. These CIDAMPs are unique in their composition due to the presence of one to three Cys and/or one Phe together with paired His-residues (see Table 13). Antimicrobial CFU-assay analyses revealed these peptides as being highly potent and efficient against *S. aureus* ATCC 6538 (see Table 13 and FIG. 9). Among all peptides tested, LCE3B$_{56-68}$, which contains three Cys residues, was identified as the most potent *S. aureus*-killing CIDAMP with an MBC90 of 44 nM (see Table 13 and FIG. 9). *S. aureus* killing efficacy of LCE3B$_{56-68}$ was in the range of 98.0-99.3% at concentrations higher than 88 nM.

Figure 11:
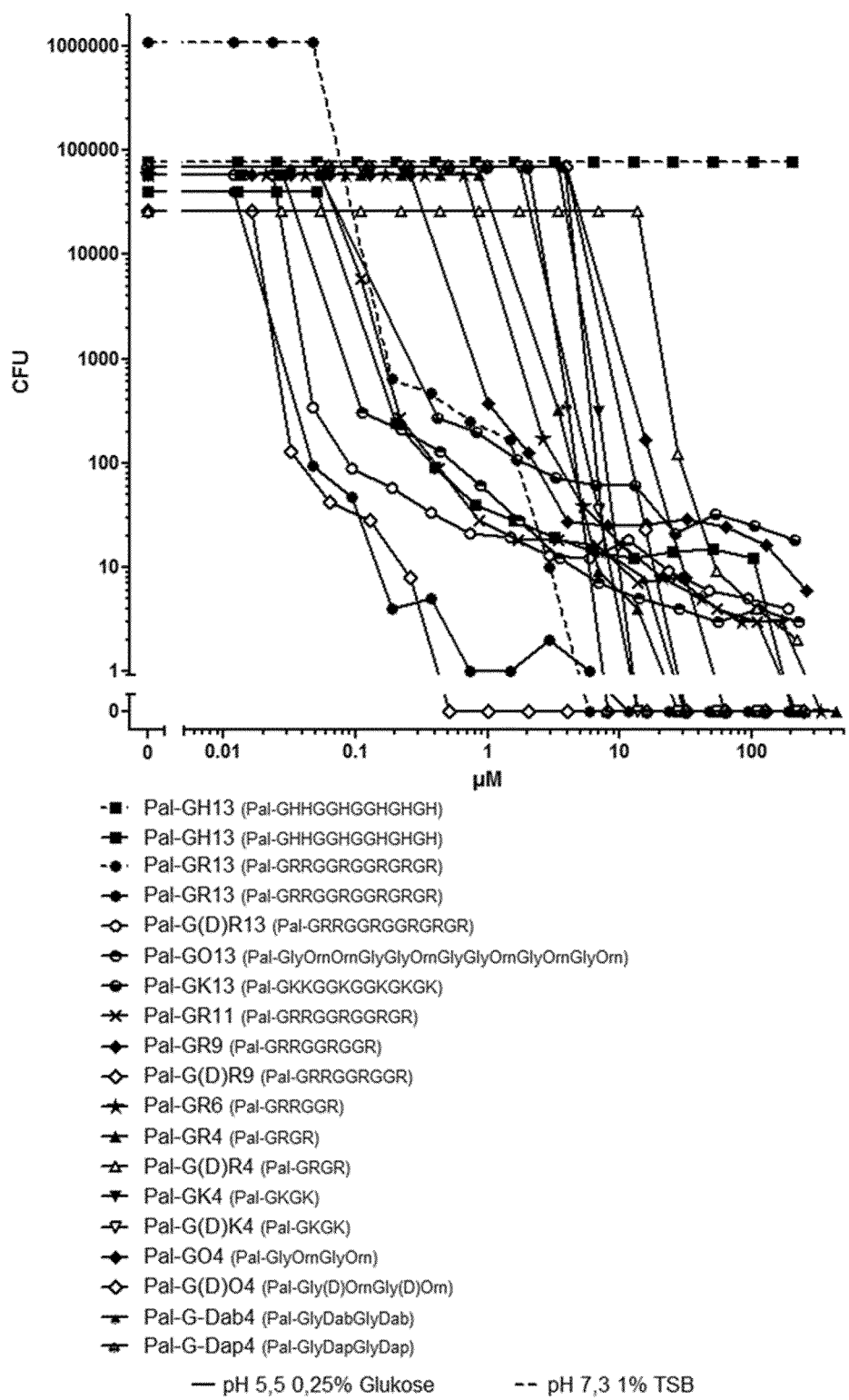
FIG. 11 shows the *S. aureus* ATCC 6538-cidal activity of various palmitoylated Gly-peptides containing the basic amino acids His, Arg, Lys, Orn, Dab or Dap (from top to bottom, the listing of sequences have SEQ ID NOS: 44, 44, 78, 78, 79, 121, 118, 16, 15, 29, 14, 13, 28, 115, 26, 116, 27, 11 and 12, respectively)

Example 4: Impact of D-Amino Acids Instead of L-Amino Acids on the Bactericidal Activity of CIDAMPs To investigate the effect of an exchange of L-amino acids against its D-forms on *S. aureus*-cidal activity, Pal-GR13 and Pal-GR9 in which all L-Arg were replaced by D-Arg were tested as above with regard to *S. aureus* (ATCC 6538)-cidal activity. For D-Pal-GR13 identical MBC90 values (0.075 µg/ml) were found as for Pal-GR13. For D-Pal-GR9, significantly lower MBC90 values (0.15 µg/ml vs. 1.18 µg/ml) and MBC100 values (2.35 µg/ml vs. 300 µg/ml) were observed (see Table 14, and FIG. 11).

Example 5: Effect of Lipidation on the Bactericidal Activity of CIDAMPs

Figure 12:
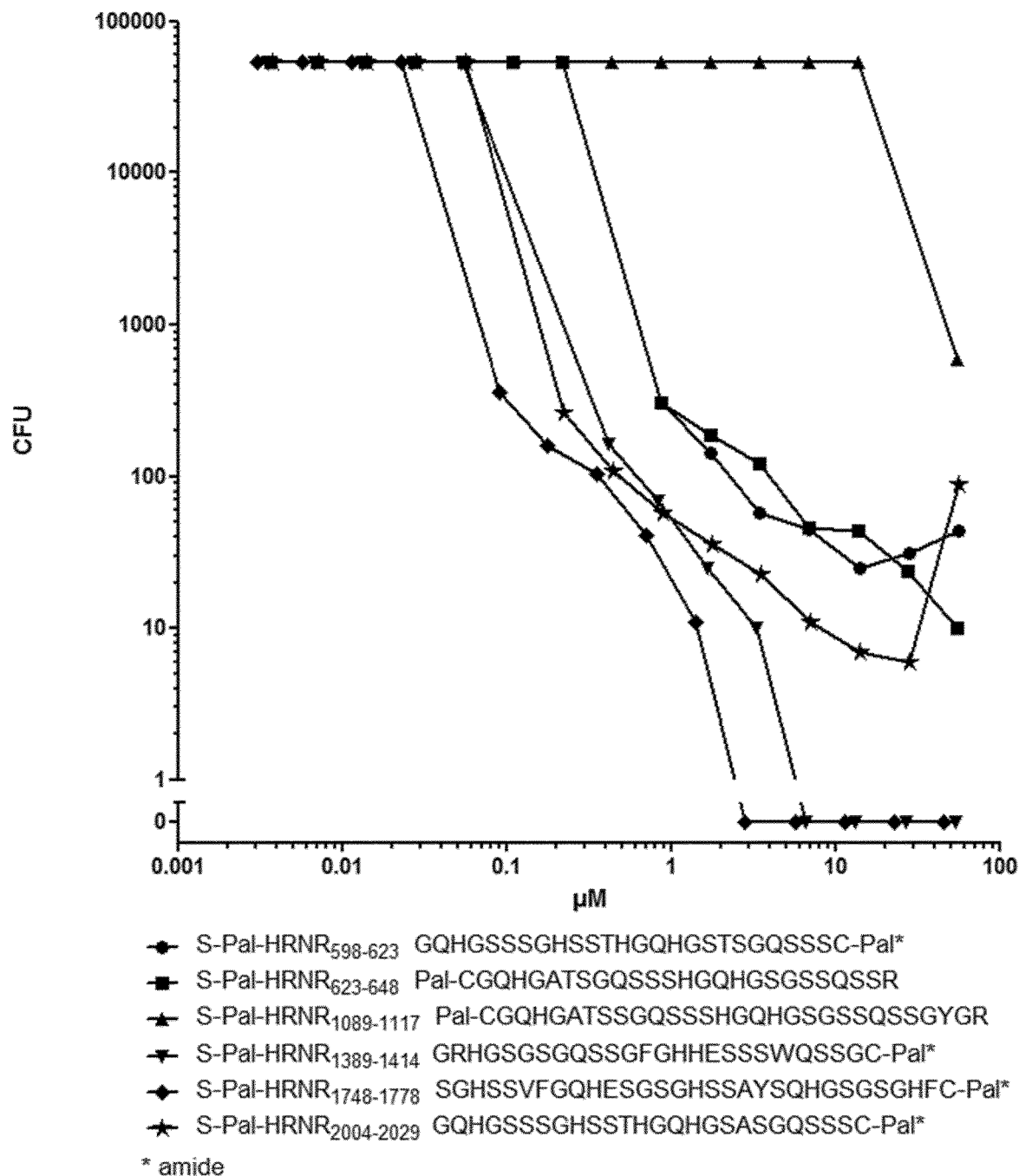
FIG. 12 shows the *S. aureus* ATCC 6538-cidal activity of various S-palmitoylated hornerin-CIDAMPs (from top to bottom, the listing of sequences have SEQ ID NOS: 128, 129, 125, 126, 127 and 130, respectively)

The effect of CIDAMP lipidation on *S. aureus*-cidal activity, was tested with various N-palmitoylated and N-myristoylated peptides. N-palmitoyl Pal-HR 1-18, which retained its *P. aeruginosa* ATCC 10145-cidal activity at pH 5.5 (see Table 16), now additionally acquired *S. aureus*-cidal activity (see Table 14 and FIG. 10). At pH 7.0, no antimicrobial activity was observed (see Table 14). Substitution of all His by Arg in HR 1-18 improved *S. aureus* ATCC 6538-cidal activity both in terms of efficacy and of potency, resulting in a CIDAMP with activity at pH 7.0 (see Table 13). Myristoylated peptides displayed nearly 6- to 9-fold less potency than palmitoylated peptides (see Table 14). Tests with palmitoylated HR 1-11- and HR 1-18-variants, in which two, three or four His were replaced by Arg showed *S. aureus*-cidal activity at pH 5.5 with a MBC90 in the range of 0.25-1 µM and a MBC100 in the range of 2 to >128 µM (see Table 14 and FIG. 12).

Further studies revealed that also small (4-13 amino acids) N-terminally palmitoylated CIDAMPs have *S. aureus*-cidal activity. In general, the MBC90 of *S. aureus*-cidal activity increased with decreasing peptide chain length for Gly- and Arg-containing palmitoylated CIDAMPs with a chain length of 4, 6, 9, 11 and 13 amino acids (see Table 16 and FIG. 11).

TABLE 16

*P. aeruginosa* ATCC 10145-cidal activity of palmitoylated and myristoylated CIDAMPs containing different basic amino acids at pH 5.5, 0.25% glucose

| Sequence | SEQ ID NO: | Name | MBC90 (μg/ml) | MBC100 (μg/ml) |
|---|---|---|---|---|
| Pal-GRHGSGLGHSSSHGQHGSGSGR | 3 | Pal-HR 1-18 | 0.075 | 0.59 |
| Myr-GRHGSGLGHSSSHGQHGSGSGR | 112 | Myr-HR 1-18 | 0.075 | 0.3 |
| Pal-GRRGSGLGRSSSRGQRGSGSGR | 5 | Pal-HR 1-18 HR | 0.038 | 0.59 |
| Pal-GRRGSGLGRSSSRGQRGSGSGR | 5 | Pal-HR 1-18 HR | 1.18 | 4.7 |
| Pal-HGSRSGQSSRGERHGSSSGSSSH | 8 | Pal-HR 1-11 | 0.075 | 0.3 |
| Pal-RGSRSGQSSRGERRGSSSGSSSR | 10 | Pal-HR 1-11 3H3R | 0.038 | 0.15 |
| Pal-RGSRSGQSSRGERR | 9 | Pal-HR 1-11 2H2R-14 | 0.038 | 0.15 |
| Pal-GRRGGRGGRGRGR | 18 | Pal-GR13 | 0.038 | 0.3 |
| Pal-GR$_D$R$_D$GGR$_D$GGR$_D$GR$_D$GR$_D$ | 19 | D-Pal-GR13 | 0.075 | 0.3 |
| Pal-GRRGGRGGRGR | 16 | Pal-GR11 | 0.075 | 0.3 |
| Pal-GRRGGRGGR | 15 | Pal-GR9 | 0.038 | 0.59 |
| Pal-GR$_D$R$_D$GGR$_D$GGR$_D$ | 29 | D-Pal-GR9 | 0.038 | 0.59 |
| Pal-GRRGGR | 14 | Pal-GR6 | 1.18 | 4.7 |
| Pal-GRGR | 13 | Pal-GR4 | 2.35 | 9.375 |
| Pal-GR$_D$GR$_D$ | 28 | D-Pal-GR4 | 18.75 | 150 |
| Pal-GKKGGKGGKGKGK | 118 | Pal-K-GR13 | <0.019 | 0.15 |
| Pal-GOOGGOGGOGOGO | 121 | Pal-Orn-GR13 | 0.075 | 0.3 |
| Pal-GKGK | 115 | Pal-GK4 | 2.38 | 9.375 |
| D-Pal-GK$_D$GK$_D$ | 26 | D-Pal-GK4 | 1.18 | 4.7 |
| Pal-GOGO | 116 | Pal-GOrn4 | 2.35 | 18.75 |
| Pal-GO$_D$GO$_D$ | 27 | D-Pal-GOrn4 | 1.18 | 9.38 |
| Pal-GDabGDab | 11 | Pal-GDab4 | 2.35 | 9.38 |
| Pal-GDapGDap | 12 | Pal-GDap4 | 2.35 | 9.38 |
| Pal-GRRGSGLGRSSSR | 6 | Pal-HR 1-18 3H3R-GR13 | 0.59 | 4.7 |

The effect of S-palmitoylation on the *S. aureus*-cidal activity of small intrinsically disordered HRNR-peptides, which contain at least three basic amino acids, was studied with six HRNR-peptides with N-terminal or C-terminal palmitoylated cysteines (S-Pal-HRNR$_{598-623}$, S-Pal-HRNR$_{623-648}$, S-Pal-HRNR$_{1089-1117}$, S-Pal-HRNR$_{1389-1414}$, S-Pal-HRNR$_{1748-1778}$ and S-Pal-HRNR$_{2004-2029}$). Except for S-Pal-HRNR$_{1089-1117}$, all showed *S. aureus*-cidal activity (see Table 15 and FIG. 12). Whereas S-Pal-HRNR$_{598-623}$ and S-Pal-HRNR$_{623-648}$ showed a similar MBC90, these lipopeptides were only able to eliminate a maximum of 99.7-99.9% of the inoculum.

In contrast, the three other amidated lipopeptides tested, S-Pal-HRNR$_{1389-1414}$, S-Pal-HRNR$_{1748-1778}$ and S-Pal-HRNR$_{2004-2029}$, were bactericidal with a MBC90 in the range of 90-420 nM. These peptides were *S. aureus*-cidal with a MBC100 in the range of 2.8-28 μM, with S-Pal-HRNR$_{1748-1778}$ being the most potent and efficient (MBC100: 2.8 μM; MBC90: 90 nM) amidated and S-palmitoylated HRNR-peptide (see Table 15 and FIG. 12). All these S-palmitoylated CIDAMPs were found to be also bactericidal for *P. aeruginosa* ATCC 10145 (data not shown).

Basic amino acids in the palmitoylated CIDAMPs are important for *S. aureus*-cidal activity. Several palmitoylated CIDAMPs containing the amino acids Lys, Orn, Dab or Dap instead of Arg, were tested. Whereas the non-palmitoylated peptides lacked *S. aureus*-cidal activity at pH 5.5, the palmitoylated CIDAMPs showed activity, with Pal-Orn-GR13 being the most potent (MBC90: 112 nM) and Pal-GDap4 being the most efficient (MBC100: 4.4 μM) CIDAMP (see Table 14 and FIG. 11).

Peptides from LCEs, LCE2B$_{74-86}$, LCE3B$_{56-68}$, LCE3C$_{55-67}$ and LCE3C$_{55-75}$ also displayed *S. aureus*-cidal activity (see Table 13). Palmitoylation further improves their staphylocidal activity. All three palmitoylated LCEs, i.e. Pal-LCE3B$_{56-68}$, Pal-LCE3C$_{55-67}$ and Pal-LCE3C$_{55-75}$ showed an increase of the potency (decrease of the MBC90)

and a MBC100 of 78-307 nM, with Pal-LCE3B$_{56-68}$ being the most potent and efficient CIDAMP against *S. aureus* ATCC 6538 (see Table 14).

Example 6: Effect of Net Positive Charge on CIDAMP Antimicrobial Activity

His-rich CIDAMPs are usually antimicrobially active under pH conditions near or below the pKs of His (pKs=6.0) (see Tables 3, 7 and FIG. 2). However, CIDAMPs that are positively charged at neutral pH also display antibacterial activity at pH 7.0 (see Table 3, 7, and FIG. 3). Both are bactericidal for the Gram-negative *P. aeruginosa*, but not for the Gram-positive *S. aureus* (see Table 13 and FIG. 9). Additionally, palmitoylated CIDAMPs or CIDAMPs containing a low percentage of hydrophobic amino acids and being rich in Ser exhibit not only *P. aeruginosa*-cidal activity, but are also active against *S. aureus* (see Tables 13-15, and FIGS. 9, 11).

Thus, the results show that a change of the CIDAMP composition towards a higher percentage of Ser together with a modest increase of the percentage of hydrophobic amino acids allows increasing the antimicrobial activity against Gram-positive bacteria.

Example 7: Antimicrobial Spectrum of Lipidated CIDAMPs

The palmitoylated peptid Pal-HR 1-18 was found to be active against *S. aureus* ATCC 6538 only at pH 5.5, whereas it was bactericidal for strains of both *S. pneumoniae* and *S. pyogenes* at neutral pH (see Table 17). Again, here the use of TSB in the medium increases both the MBC90 and MBC100 values. Pal-HR 1-18 was only very weakly bactericidal for *B. cepacia*. It was, however, bactericidal for *K. pneumoniae* ATCC 13883 at pH 5.5. It was also bactericidal for the anaerobic bacteria *P. acnes* ATCC 6919, *P. oralis* ATCC 33321 and *C. perfringens* ATCC 13124. Highest activity against *P. acnes* ATCC 6919 was observed at pH 5.5, but at neutral pH the activity was only slightly decreased (see Table 17). At pH 7.3, Pal-HR 1-18 was bactericidal for *P. oralis* ATCC 33321 with a MDC90 at 8 M. It was also bactericidal for *C. perfringens* ATCC 13124 at pH 7.3 with a MDC90 of 4.6 µM.

TABLE 17

Antimicrobial activity spectrum of palmitoyl-HR 1-18

| Microbe | MBC90 (µg/ml) | MBC100 (µg/ml) | Conditions |
|---|---|---|---|
| *Staphylococcus epidermidis* ATCC 14990 | >300 | >300 | pH 7.3, 1% TSB |
| *Staphylococcus aureus* ATCC 6538 | 1.18 | 37.5 | pH 5.5, 0.25% glucose |
| *Staphylococcus aureus* ATCC 6538 | >300 | >300 | pH 7.3, 1% TSB |
| *Streptococcus pneumoniae* ATCC 33400 | 2.35 | 9.37 | pH 6.5, 0.25% glucose |
| *Streptococcus pneumoniae* ATCC 33400 | 9.38 | 37.5 | pH 7.3, 1% TSB |
| *Streptococcus pneumoniae* ATCC 33400 | 2.35 | 4.7 | pH 7.3, 0.25% glucose |
| *Burkholderia cepacia* ATCC 25416 | 75 | >300 | pH 7.3, 0.25% glucose |
| *Burkholderia cepacia* ATCC 25416 | >300 | >300 | pH 5.5, 0.25% glucose |
| *Pseudomonas aeruginosa* ATCC10145 | 0.075 | 0.59 | pH 5.5, 0.25% glucose |
| *Streptococcus pyogenes* ATCC 12344 | 0.15 | 0.59 | pH 6.0, 0.25% glucose |
| *Streptococcus pyogenes* ATCC 12344 | 9.38 | 9.375 | pH 7.3, 1% TSB |
| *Streptococcus pyogenes* ATCC 12344 | 0.15 | 0.3 | pH 7.3, 0.25% glucose |
| *Klebsiella pneumoniae* ATCC 13883 | 0.3 | 1.18 | pH 5.5, 0.25% glucose |
| *Propionibacterium acnes* ATCC 6919 | 0.3 | 0.59 | pH 5.5, 0.25% glucose |
| *Propionibacterium acnes* ATCC 6919 | 1.18 | 4.7 | pH 7.3, 1% TSB |
| *Propionibacterium acnes* ATCC 6919 | 0.59 | 2.35 | pH 7.3, 0.25% glucose |
| *Prevotella oralis* ATCC 33321 | 37.5 | >300 | pH 6.5, 0.25% glucose |
| *Prevotella oralis* ATCC 33321 | 18.75 | 150 | pH 7.3, 1% TSB |
| *Clostridium perfringens* ATCC 13124 | 18.75 | 37.5 | pH 7.3, 1% TSB |
| *Clostridium perfringens* ATCC 13124 | 37.5 | 75 | pH 5.5, 0.25% glucose |
| *Clostridium perfringens* ATCC 13124 | 4.7 | 18.75 | pH 7.3, 0.25% glucose |

Pal-HR 1-18 HR differs from Pal-HR 1-18 by replacement of all His by Arg. When comparing its antimicrobial activity spectrum with that of Pal-HR 1-18, the most striking difference lies in *S. aureus*-cidal activity. Pal-HR 1-18 HR is also active at pH 7.3 (see Table 18). For the other bacterial strains tested, bactericidal activity mostly increased, as seen by a slightly lower MBC100 and MBC90 (see Table 18).

TABLE 18

Antimicrobial activity spectrum of palmitoyl-HR 1-18 HR

| Microbe | MBC90 (µg/ml) | MBC100 (µg/ml) | Conditions |
|---|---|---|---|
| *Staphylococcus aureus* ATCC 6538 | 0.3 | 4.7 | pH 5.5, 0.25% glucose |
| *Staphylococcus aureus* ATCC 6538 | 1.18 | 9.375 | pH 7.3, 1% TSB |
| *Streptococcus pneumoniae* ATCC 33400 | 9.375 | 9.375 | pH 7.3, 0.25% glucose |
| *Burkholderia cepacia* ATCC 25416 | 75 | 150 | pH 7.3, 1% TSB |
| *Burkholderia cepacia* ATCC 25416 | 75 | 300 | pH 7.3, 0.25% glucose |
| *Pseudomonas aeruginosa* ATCC10145 | 1.18 | 4.7 | pH 7.3, 1% TSB |
| *Pseudomonas aeruginosa* ATCC10145 | 0.038 | 0.59 | pH 5.5, 0.25% glucose |
| *Streptococcus pyogenes* ATCC 12344 | 0.15 | 0.3 | pH 7.3, 0.25% glucose |

TABLE 18-continued

Antimicrobial activity spectrum of palmitoyl-HR 1-18 HR

| Microbe | MBC90 (µg/ml) | MBC100 (µg/ml) | Conditions |
|---|---|---|---|
| *Propionibacterium acnes* ATCC 6919 | 1.18 | 4.7 | pH 7.3, 1% TSB |
| *Prevotella oralis* ATCC 33321 | 37.5 | 75 | pH 7.3, 1% TSB |
| *Clostridium perfringens* ATCC 13124 | 4.7 | 9.375 | pH 7.3, 0.25% glucose |

The effect of N-terminal myristoylation instead of palmitoylation on the antimicrobial spectrum of Pal-HR 1-18 may be summarized as follows: all tested bacterial strains revealed sensitivity towards Myr-HR 1-18 (see Table 19). In terms of activity against *S. aureus* ATCC 6538 at pH 7.3, while Pal-HR 1-18 is inactive (see Table 18), Myr-HR 1-18 is active (see Table 19). For the tested strains of *S. pneumonia, S. pyogenes, P. aeruginosa* and *B. cepacia*, bactericidal activity is mostly similar between myristoylated and palmitoylated peptides (see Table 18). Striking differences were observed for the anaerobic bacteria *P. acnes* ATCC 6919, *P. oralis* ATCC 33321 and *C. perfringens* ATCC 13124. These strains showed a marked decrease of sensitivity towards Myr-HR 1-18 when compared with Pal-HR 1-18 (see Tables 18-19).

TABLE 19

Antimicrobial activity spectrum of myristoyl-HR 1-18

| Microbe | MBC90 (µg/ml) | MBC100 (µg/ml) | Conditions |
|---|---|---|---|
| *Staphylococcus aureus* ATCC 6538 | 18.75 | 75 | pH 7.3, 1% TSB |
| *Streptococcus pneumoniae* ATCC 33400 | 18.75 | 37.5 | pH 7.3, 1% TSB |
| *Burkholderia cepacia* ATCC 25416 | >300 | >300 | pH 5.5, 0.25% glucose |
| *Streptococcus pyogenes* ATCC 12344 | 18.75 | 18.75 | pH 7.3, 1% TSB |
| *Propionibacterium acnes* ATCC 6919 | 9.38 | 18.75 | pH 7.3, 1% TSB |
| *Prevotella oralis* ATCC 33321 | 300 | >300 | pH 7.3, 1% TSB |
| *Clostridium perfringens* ATCC 13124 | 75 | 150 | pH 7.3, 1% TSB |
| *Pseudomonas aeruginosa* ATCC10145 | 9.38 | 18.75 | pH 7.3, 1% TSB |

Figure 9:
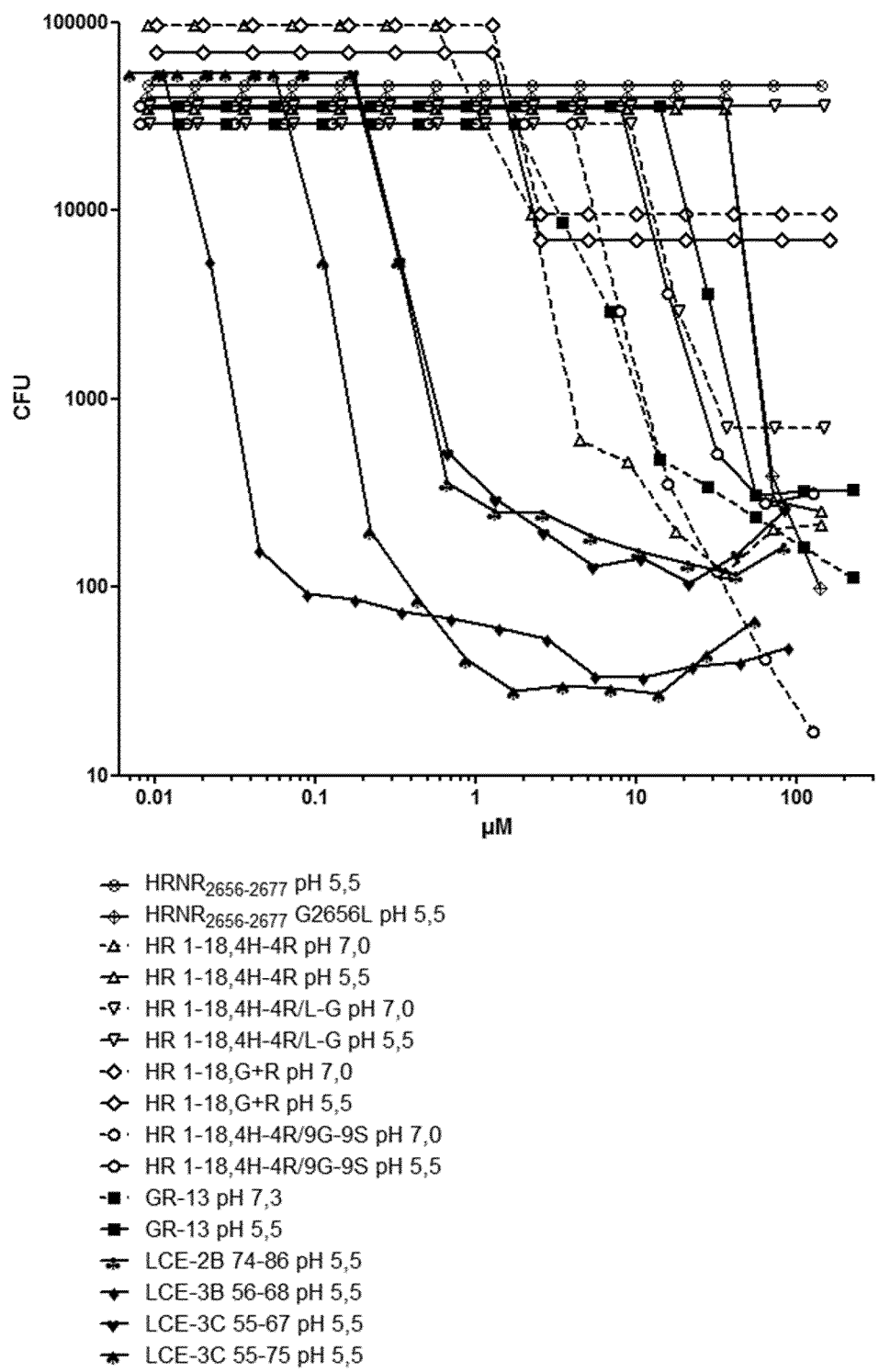
FIG. 9 shows the *S. aureus* ATCC 6538-cidal activity of various CIDAMPs.
Figure 13:
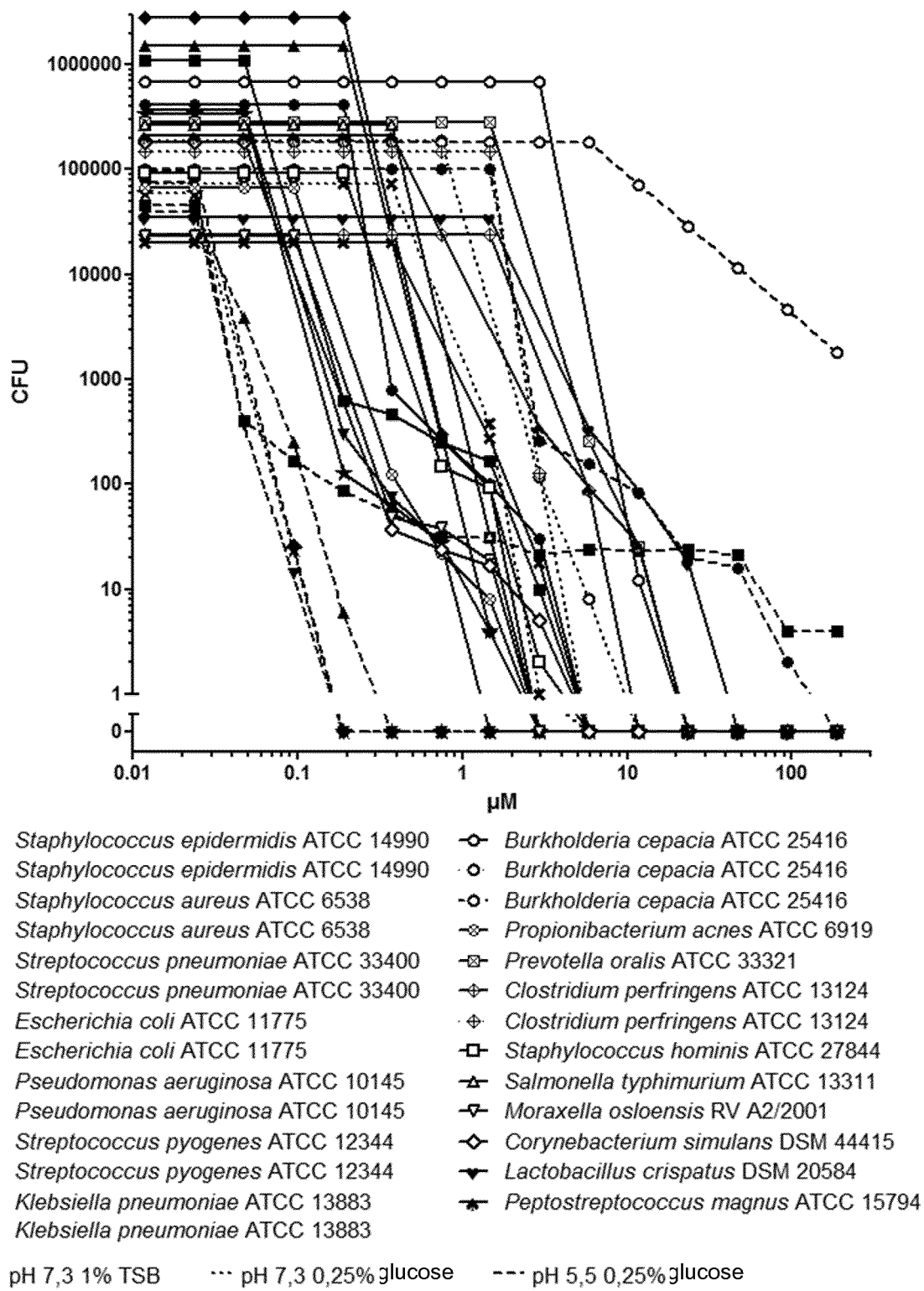
FIG. 13 shows the antimicrobial activity spectrum of Pal-GR13 against several bacterial strains.

With respect to palmitoylated Gly-Arg-rich peptides, the results show that these peptides are very potent and efficient staphylocidal CIDAMPs (see Tables 13-14 and FIG. 9). Therefore the antimicrobial spectrum of the lipopeptide Pal-GR13 was investigated with several bacterial strains (see Table 20 and FIG. 13). Sensitivity towards this lipopeptide was observed for all tested bacterial strains, albeit often with marked differences in the MBC100 and MBC90. For example, Pal-GR13 kills several bacterial species including *S. aureus* ATCC 6538, *S. pneumoniae, S. pyogenes* and *P. aeruginosa* at similar or slightly lower concentrations than Pal-HR 1-18 HR at pH 7.3 (see Table 20). The most striking observation was the identification of conditions, which—unlike HR 1-18 HR (see Table 18)—enable Pal-GR13 to kill *B. cepacia*, a bacterial species known for its notorious resistance to cationic antimicrobial peptides (Sahly et al., 2003, *Antimicrob. Agents Chemother.*, 47, 1739-41).

TABLE 20

Antimicrobial activity spectrum of palmitoyl-GR13

| Microbe | MBC90 (µg/ml) | MBC100 (µg/ml) | Conditions |
|---|---|---|---|
| *Staphylococcus epidermidis* ATCC 14990 | 9.38 | 150 | pH 5.5, 0.25% glucose |
| *Staphylococcus epidermidis* ATCC 14990 | 0.59 | 4.7 | pH 7.3, 1% TSB |
| *Staphylococcus aureus* ATCC 6538 | 0.075 | 0.3 | pH 5.5, 0.25% glucose |
| *Staphylococcus aureus* ATCC 6538 | 0.3 | 4.7 | pH 7.3, 1% TSB |
| *Streptococcus pneumoniae* ATCC 33400 | 2.35 | 4.7 | pH 7.3, 1% TSB |
| *Escherichia coli* ATCC 11775 | 1.18 | 2.35 | pH 7.3, 1% TSB |
| *Escherichia coli* ATCC 11775 | 0.15 | 0.59 | pH 5.5, 0.25% glucose |
| *Pseudomonas aeruginosa* ATCC 10145 | 0.3 | 1.18 | pH 7.3, 1% TSB |
| *Pseudomonas aeruginosa* ATCC10145 | 0.075 | 0.3 | pH 5.5, 0.25% glucose |
| *Streptococcus pyogenes* ATCC 12344 | 0.15 | 0.3 | pH 7.3, 1% TSB |
| *Klebsiella pneumoniae* ATCC 13883 | 1.18 | 1.18 | pH 7.3, 1% TSB |
| *Klebsiella pneumoniae* ATCC 13883 | 0.15 | 0.3 | pH 5.5, 0.25% glucose |
| *Burkholderia cepacia* ATCC 25416 | 18.75 | 18.75 | pH 7.3, 1% TSB |
| *Burkholderia cepacia* ATCC 25416 | 4.7 | 9.375 | pH 7.3, 0.25% glucose |
| *Burkholderia cepacia* ATCC 25416 | >300 | >300 | pH 5.5, 0.25% glucose |
| *Propionibacterium acnes* ATCC 6919 | 1.18 | 4.7 | pH 7.3, 1% TSB |

TABLE 20-continued

Antimicrobial activity spectrum of palmitoyl-GR13

| Microbe | MBC90 (µg/ml) | MBC100 (µg/ml) | Conditions |
|---|---|---|---|
| Propionibacterium acnes ATCC 6919 | 0.59 | 2.35 | pH 7.3, 0.25% glucose |
| Propionibacterium acnes ATCC 6919 | 0.3 | 0.59 | pH 5.5, 0.25% glucose |
| Prevotella oralis ATCC 33321 | 9.38 | 18.75 | pH 7.3, 1% TSB |
| Clostridium perfringens ATCC 13124 | 18.75 | 37.5 | pH 7.3, 1% TSB |
| Clostridium perfringens ATCC 13124 | 4.7 | 18.75 | pH 7.3, 0.25% glucose |
| Clostridium perfringens ATCC 13124 | 37.5 | 75 | pH 5.5, 0.25% glucose |
| Staphylococcus hominis ATCC 27844 | 1.18 | 4.7 | pH 7.3, 1% TSB |
| Salmonella typhimurium ATCC 13311 | 2.35 | 2.35 | pH 7.3, 1% TSB |
| Moraxella osloensis RV A2/2001 | 0.59 | 4.7 | pH 7.3, 1% TSB |
| Corynebacterium simulans DSM 44415 | 0.59 | 2.35 | pH 7.3, 1% TSB |
| Lactobacillus crispatus DSM 20584 | 9.38 | 75 | pH 7.3, 1% TSB |
| Peptostreptococcus magnus ATCC 15794* | 4.7 | 37.5 | pH 7.3, 1% TSB |

*now Finegoldia magna

Figure 10:
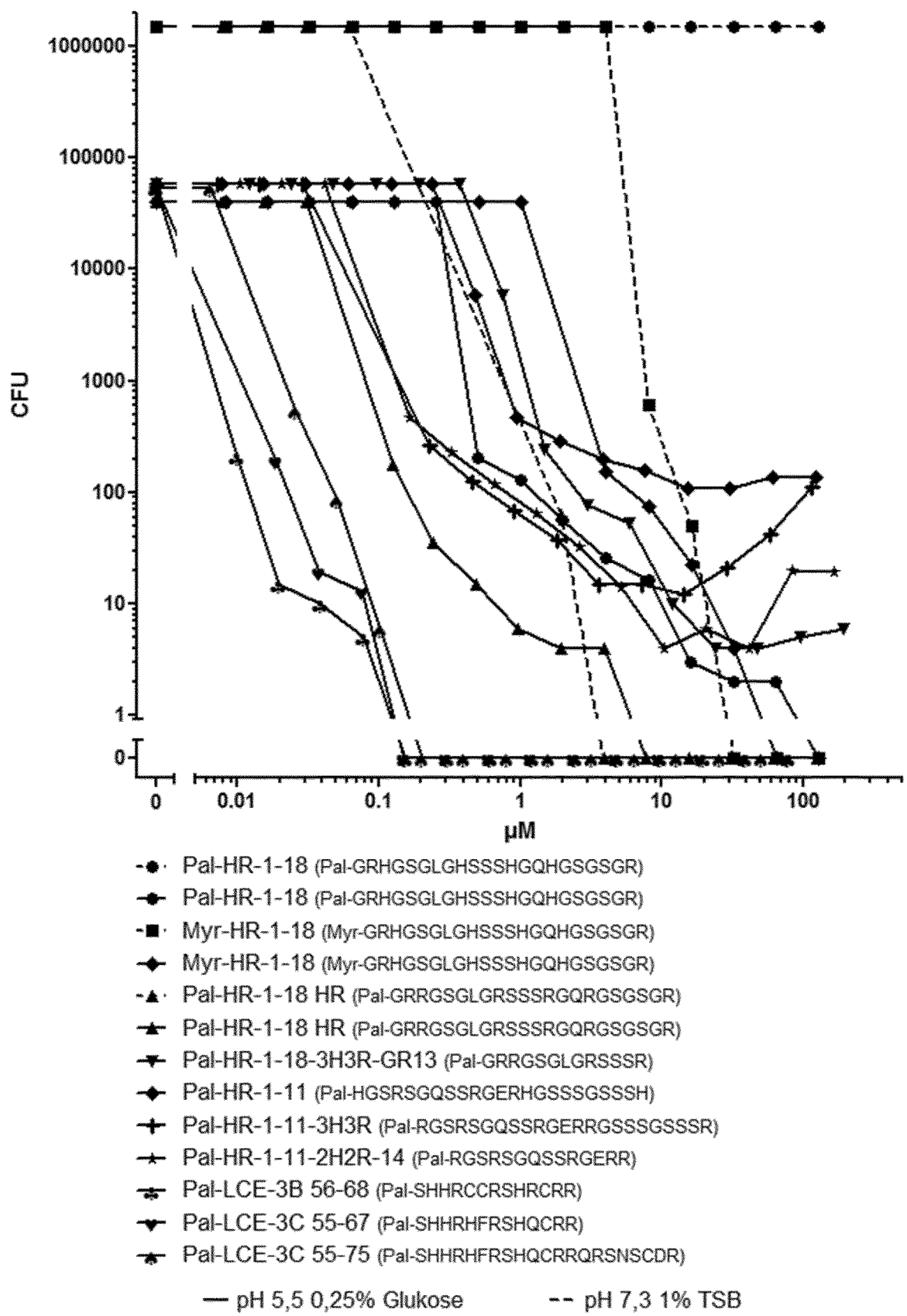
FIG. 10 shows the *S. aureus* ATCC 6538-cidal activity of various palmitoylated and myristoylated HR 1-18, HR 1-11, LCE3B and LCE3C peptides (from top to bottom, the listing of sequences have SEQ ID NOS: 3, 3, 112, 112, 5, 5, 6, 8, 10, 9, 27, 23 and 120, respectively)

With respect to the studied palmitoylated LCE-proteins, the three Gys-residues-containing Pal-LCE3B$_{56-68}$ was the most potent and efficient *S. aureus*-killing lipopeptide (see FIG. 10). This peptide has a similar activity to Pal-GR13 against *B. cepacia, E. coli, S. pyogenes*, and *S. typhimurium* at pH 7.3 (see Table 21 and FIG. 14). At pH 5.5, however, *S. typhimurium* is extremely sensitive to Pal-LCE3B$_{56-68}$ with a MBC100 at 155 nM and a MBC90 at 20 nM (see Table 21). In addition, sensitivity of *S. pneumoniae* towards this lipopeptide was 2- to 3-fold higher than towards Pal-GR13. On the other hand, *K. pneumoniae* ATCC 13883 sensitivity towards Pal-LCE3B$_{56-68}$ was lower than towards Pal-GR13 (see Tables 20-21 and FIGS. 11, 14).

TABLE 21

Antimicrobial activity spectrum of palmitoyl-LCE3B$_{56-68}$

| Microbe | MBC90 (µg/ml) | MBC100 (µg/ml) | Conditions |
|---|---|---|---|
| Staphylococcus aureus ATCC 6538 | <0.019 | 0.15 | pH 5.5, 0.25% glucose |
| Staphylococcus epidermidis ATCC 14990 | 0.3 | 0.3 | pH 5.5, 0.25% glucose |
| Streptococcus pneumoniae ATCC 33400 | 0.59 | 2.35 | pH 7.3, 0.25% glucose |
| Burkholderia cepacia ATCC 25416 | 4.7 | 9.375 | pH 7.3, 0.25% glucose |
| Burkholderia cepacia ATCC 25416 | >300 | >300 | pH 5.5, 0.25% glucose |
| Streptococcus pyogenes ATCC 12344 | 0.15 | 0.59 | pH 6.0, 0.25% glucose |
| Streptococcus pyogenes ATCC 12344 | 0.15 | 0.3 | pH 7.3, 0.25% glucose |
| Klebsiella pneumoniae ATCC 13883 | 2.35 | 4.7 | pH 7.3, 0.25% glucose |
| Klebsiella pneumoniae ATCC 13883 | 0.15 | 9.375 | pH 5.5, 0.25% glucose |
| Salmonella typhimurium ATCC 13311 | 1.18 | 2.35 | pH 7.3, 0.25% glucose |
| Salmonella typhimurium ATCC 13311 | 0.038 | 0.3 | pH 5.5, 0.25% glucose |
| Escherichia coli ATCC11775 | 0.59 | 1.18 | pH 7.3, 0.25% glucose |
| Escherichia coli ATCC11775 | 0.3 | >300/37.5* | pH 5.5, 0.25% glucose |
| Pseudomonas aeruginosa ATCC10145 | 0.075 | 0.3 | pH 5.5, 0.25% glucose |

*antimicrobial paradox (increased bacterial growth with increasing CIDAMP-concentrations).

Example 8: CIDAMPs with *Burkholderia cepacia*-Cidal Activity

*B. cepacia* is associated with nosocomial infections, especially among cystic fibrosis patients or chronic granulomatous disease which can lead to a rapid decline of lung function. *B. cepacia* infections are difficult to treat because they are highly antibiotic resistant, making alternative treatments attractive. Although antimicrobial peptides seem to represent such alternative therapy option, it suggests that *B. cepacia* is naturally resistant towards cationic amphipatic peptides such as human β-defensin 3 (Sahly et al., 2003, *Antimicrob. Agents Chemother.,* 47, 1739-41). Surprisingly, Pal-HR 1-18 and Pal-LCE3B$_{56-68}$ were identified as *B. cepacia*-cidal >IDAMPs (MB100: 4.9 µM; MBC90: 2.4 µM) with activity at pH 7.3 (see Table 22), suggesting that modified CIDAMPs are promising candidates for novel *B. cepacia*-cidal antimicrobials.

TABLE 22

Burkholderia cepacia ATCC 25416-cidal activity of various CIDAMPs

| Sequence | SEQ ID NO: | Name | MBC90 (µg/ml) | MBC100 (µg/ml) | Condition |
|---|---|---|---|---|---|
| Pal-GRRGGRGGRGRGR | 18 | Pal-GR13 | 18.75 | 18.75 | pH 7.3, 1% TSB |
| Pal-GRRGGRGGRGRGR | 18 | Pal-GR13 | >300 | >300 | pH 5.5, 0.25% glucose |
| Pal-GRRGSGLGRSSSR | 6 | Pal-HR 1-18 3H3R-GR13 | 4.7 | 9.38 | pH 7.3, 0.25% glucose |
| Pal-GRRGSGLGRSSSR | 6 | Pal-HR 1-18 3H3R-GR13 | >300 | >300 | pH 5.5, 0.25% glucose |
| Pal-GRHGSGLGHSSSHGQHGSGSGR | 3 | Pal-HR 1-18 | 75 | >300 | pH 7.3, 0.25% glucose |
| Pal-GRHGSGLGHSSSHGQHGSGSGR | 3 | Pal-HR 1-18 | >300 | >300 | pH 5.5, 0.25% glucose |
| Pal-GRRGSGLGRSSSRGGRGSGSGR | 117 | Pal-HR 1-18 4H-4R | 75 | 150 | pH 7.3, 1% TSB |
| Pal-GRRGSGLGRSSSRGGRGSGSGR | 117 | Pal-HR 1-18 4H-4R | 75 | 300 | pH 7.3, 0.25% glucose |
| Pal-SHHRCCRSHRCRR | 21 | Pal-LCE3B$_{56-68}$ | 4.7 | 9.38 | pH 7.3, 0.25% glucose |
| Pal-SHHRCCRSHRCRR | 21 | Pal-LCE3B$_{56-68}$ | >300 | >300 | pH 5.5, 0.25% glucose |

Example 9: CIDAMPs with *Klebsiella pneumoniae*-Cidal Activity

The Gram-negative opportunistic pathogen *K. pneumoniae* is responsible for a spectrum of community-acquired and nosocomial infections and typically infects patients with indwelling medical devices, on which this microorganism is able to grow as a biofilm. Pal-GR13 was identified as the most potent (MBC90: 63 nM) and most efficient (MBC100: 189 µM) *K. pneumoniae* ATCC 13883-cidal CIDAMP at pH 5.5. Pal-LCE3B$_{56-68}$ showed a similar potency (MBC90: 52 nM), but was far less efficient (MBC100: 4.9 µM) under the same conditions (see Table 23). Testing a multidrug-resistant *K. pneumoniae* ATCC 700603 in Mueller-Hinton medium at pH 7.4 identified Pal-HR 1-18 HR, Pal-GR13 and Pal-GR9 as able to eradicate this strain at 32 µg/ml and 18 h incubation time.

TABLE 23

Klebsiella pneumoniae ATCC 13883-cidal activity of various CIDAMPs

| Sequence | SEQ ID NO: | Name | MBC90 (µg/ml) | MBC100 (µg/ml) | Condition |
|---|---|---|---|---|---|
| Pal-GRHGSGLGHSSSHGQHGSGSGR | 3 | Pal-HR 1-18 | 0.3 | 1.18 | pH 5.5, 0.25% glucose |
| Pal-SHHRPRLFHRRRH | 119 | Pal-LCE-3B | 2.35 | 4.7 | pH 7.3, 0.25% glucose |
| Pal-SHHRPRLFHRRRH | 119 | Pal-LCE-3B | 0.15 | 9.38 | pH 5.5, 0.25% glucose |
| Pal-GRRGGRGGRGRGR | 18 | Pal-GR13 | 1.18 | 1.18 | pH 7.3, 1% TSB |
| Pal-GRRGGRGGRGRGR | 18 | Pal-GR13 | 0.15 | 0.3 | pH 5.5, 0.25% glucose |

Example 10: CIDAMPs with *Candida albicans*-Cidal Activity

*C. albicans* ATCC 24433 was killed by HR 1-17 and HR 1-18 (MBC90 at 0.56 µM and 6.6 µM, respectively). HR 1-17 affects *C. albicans* ATCC 24433 with highest activity at pH 5.5 in the absence of TSB in the medium (see Tables 12, 24). As seen with *P. aeruginosa*-cidal activity, an increase of pH to 7.2 abolishes the fungicidal activity. Furthermore, the substitution of any of the Arg residues by Gly leads to a dramatic reduction or loss of candidacidal activity (see Table 24). Another CIDAMP, FLG-2$_{2082-2105}$, also showed candidacidal activity at pH 5.5, which is nearly 50-fold reduced at pH 7.2 (see Table 24).

TABLE 24

*Candida albicans* ATCC 24433-cidal activity of various CIDAMPs

| Sequence | SEQ ID NO: | Name | MBC90 (µg/ml) | MBC100 (µg/ml) | Condition |
|---|---|---|---|---|---|
| HGSRSGQSSRGERHGSSSGSSSH | 53 | HR 1-11 | 9.38 | 150 | pH 5.5, 0.25% glucose |
| GRHGSGLGHSSSHGQHGSGSGRSSSRGPY | 64 | HR 1-17 | >300 | >300 | pH 7.2, 1.% TSB |
| GRHGSGLGHSSSHGQHGSGSGRSSSRGPY | 64 | HR 1-17 | 9.38 | >300 | pH 5.5, 1% TSB |
| GGHGSGLGHSSSHGQHGSGSGRSSSRGPY | 65 | HR 1-17 R2657G | >300 | >300 | pH 5.5, 1% TSB |
| GRHGSGLGHSSSHGQHGSGSGGSSSRGPY | 66 | HR 1-17 R2677G | 300 | >300 | pH 5.5, 1% TSB |
| GRHGSGLGHSSSHGQHGSGSGRSSSGGPY | 67 | HR 1-17 R2681G | 300 | >300 | pH 5.5, 1% TSB |
| GRHGSGLGHSSSHGQHGSGSGRSSSRGPY | 64 | HR 1-17 | 1.18 | 9.38 | pH 5.5, 0.25% glucose |
| GRHGSGLGHSSSHGQHGSGSGR | 2 | HR 1-18 | 150 | >300 | pH 5.5, 1% TSB |
| FITC-GRHGSGLGHSSSHGQHGSGSGR | 30 | FITC-HR 1-18 | 2.35 | 75 | pH 5.5, 0.25% glucose |
| Pal-GRRGGRGGRGRGR | 18 | Pal-GR13 | 4.7 | 18.75 | pH 7.3, 1.% TSB |
| Pal-GRRGGRGGRGRGR | 18 | Pal-GR13 | 0.59 | 2.35 | pH 5.5, 0.25% glucose |
| Pal-GRRGSGLGRSSSR | 6 | Pal-HR 1-18 3H3R-GR13 | 4.7 | 18.75 | pH 7.3, 1% TSB |
| Pal-GRRGSGLGRSSSR | 6 | Pal-HR 1-18 3H3R-GR13 | 0.59 | 1.18 | pH 5.5, 0.25% glucose |
| HAHSGHGQSTQRGSRTAGRRGSGH | 38 | FLG-22082 2105 | 150 | >300 | pH 7.2, 0.25% glucose |
| HAHSGHGQSTQRGSRTAGRRGSGH | 38 | FLG-22082 2105 | 2.35 | 18.75 | pH 5.5, 0.25% glucose |

FITC = fluorescein isothiocyanate

Furthermore, similarly to the observations regarding antibacterial activity, palmitoylation of the CIDAMPs leads to a dramatic increase in the fungicidal effect on *C. albicans* ATCC 24433—as seen with Pal-HR 1-18 HR and Pal-GR13 (see Table 24). Testing the FDA control strain *C. albicans* ATCC 928 in Mueller-Hinton medium at pH 7.4 identified Pal-HR 1-18 HR, Pal-GR13, Pal-GR9, Pal-GR4, Pal-GDap4, Pal-LE3C$_{55-67}$ and Pal-LCE3C$_{56-68}$ as CIDAMPs able to inhibit this yeast strain at a MIC of 1-32 µg/ml and 18 h incubation time (see Table 25).

TABLE 25

Antifungal activity of several CIDAMPs*: A-active; I-inactive under standard conditions at pH 7.4

| Name | Sequence | SEQ ID NO: | C. albcans ATCC90028 | C. neoformans ATCC 208821 |
|---|---|---|---|---|
| Pal-GR4 | Pal-GRGR | 13 | A | A |
| Pal-GR9 | Pal-GRRGGRGGR | 15 | A | A |
| Pal-K-GR13 | Pal-GKKGGKGGKGKGK | 118 | I | I |
| Pal-GDap4 | Pal-GDapGDap | 12 | A | A |

TABLE 25-continued

Antifungal activity of several CIDAMPs*: A-active; I-inactive under standard conditions at pH 7.4

| Name | Sequence | SEQ ID NO: | C. albcans ATCC90028 | C. neoformans ATCC 208821 |
|---|---|---|---|---|
| Pal-LCE3B$_{56-68}$ | Pal-SHHRCCRSHRCRR | 21 | A | A |
| Pal-LCE3C$_{55-67}$ | Pal-SHHRHFRSHQCRR | 23 | A | A |
| Pal-HR 1-18 HR | Pal-GRRGSGLGRSSSRGQRGSGSGR | 5 | A | A |
| Pal-HR 1-11 2H2R-14 | Pal-RGSRSGQSSRGERR | 9 | I | A |
| Pal-GR13 | Pal-GRRGGRGGRGRGR | 18 | A | A |
| HR 1-18 GR | GRRGGGGRGGGRGGRGGGGR | 74 | I | I |
| GR13 | GRRGGRGGRGRGR | 17 | I | I |
| LCE2B$_{74-86}$ | SHHRPRLFHRRRH | 107 | I | A |
| LCE3B$_{56-68}$ | SHHRCCRSHRCRR | 20 | I | A |
| LCE3C$_{55-67}$ | SHHRHFRSHQCRR | 22 | I | A |
| LCE3C$_{55-75}$ | SHHRHFRSHQCRRQRSNSCDR | 110 | I | A |

Dap = (L)1,3-diaminopropionic acid
*: activity at concentration <32 pg/ml

Example 11: CIDAMPs with *Cryptococcus neoformans*-Cidal Activity

Cryptococcosis, caused by the ubiquitous soil fungus *C. neoformans*, is one of the most important, life-threatening fungal infections of humans and a leading mycological cause of morbidity and mortality among AIDS patients as well as severely immunocompromised patients without AIDS. CIDAMPs could be ideal therapeutics fulfilling many of the criteria for an ideal cryptococcal therapeutic: LCEs 2B,-3B, -3C and its palmitoylated variants show target-specificity of microbicidal activity (see Table 25), not killing other microbes when tested in Mueller-Hinton medium at pH 7.4.

Thus, LCEs are likely not to damage the commensal microflora under such conditions. The high potency and absent toxicity of these LCEs against the human HEK293 cell line (see Table 27) make them extremely promising cryptococcal therapeutics.

Example 12: CIDAMP Activity Against Commensal Strains

Most of the antibiotics currently used also kill members of the local microflora due to their broad-spectrum activity. To avoid this, antimicrobials are needed which optimally kill pathogens but spare commensals. A selection of commensal strains, namely *S. epidermidis* ATCC 14990, *Staphylococcus hominis* ATCC 27844, *M. osloensis* RV A2/2001, *C. simulans* DSM 44415, *L. crispatus* DSM 20584 and *P. magnus* ATCC 15794 was tested (see Table 20) and found to be also sensitive to Pal-GR13 at pH 7.3. The skin commensal *S. epidermidis* shows a low sensitivity towards Pal-GR13 at pH 5.5 (MBC100=150 μg/ml), the relevant pH value for the skin environment. Pal-GR13 therefore is a promising CIDAMP, for example against *S. aureus* (MBC100=0.3 μg/ml), *P. aeruginosa* (MBC100=0.3 μg/ml), *E. coli* (MBC100=0.59 μg/ml), *K. pneumoniae* (MBC100=0.3 μg/ml) and *P. acnes* (MBC100=0.59 μg/ml), concomitantly sparing *S. epidermidis* in acidic environments of about pH 5.5 (see Table 20).

Example 13: Synergistic Effects of HR 1-8 and HR 2-8 on *P. aeruginosa* ATCC 10145-cidal activity A mixture of different CIDAMPs can increase potency and efficacy of antimicrobial activity in a synergistic manner. For example, a 1:1 mixture of HR 1-8 HRNR$_{2658-2677}$ and HR 2-8 is both more potent and more efficient against *P. aeruginosa* ATCC 10145 than HR 1-8 HRNR$_{2658-2677}$ or HR 2-8 alone (see Table 26).

TABLE 26

Synergistic effects of HR 1-8- and HR 2-8- *P. aeruginosa* ATCC 10145-cidal activity at pH 5.5, 1% TSB

| Sequence | SEQ ID NO: | Name | MBC90 (μg/ml) | MBC100 (μg/ml) |
|---|---|---|---|---|
| HGSGLGHSSSHGQHGSGSGR | 84 | HR 1-8 HRNR$_{2658-2677}$ | 37.5 | >300 |
| GSGSRQSPSYGR | 94 | HR 2-8 | 18.75 | >300 |
| HGSGLGHSSSHGQHGSGSGR + GSGSRQSPSYGR | 94 + 94 | HR 1-8 HRNR$_{2658-2677}$ + HR 2-8 | 2.35 | 150 |

Example 14: Improvement of S. aureus-Killing Activity of Palmitoylated CIDAMPs Palmitoylated CIDAMPs (e.g. Pal-GR13) are less potent against *S. aureus* than against *P. aeruginosa* and are also less efficient, killing less than 100% of the inoculum. To solve this problem, *S. aureus* was treated with CIDAMPs in 10 mM phosphate buffer, pH 5.5, plus 0.25% glucose, containing the biosurfactant rhamnolipid at its critical micell concentration (CMC), 40 µg/ml, and changes of the $OD_{620}$ were determined using a conventional plate antimicrobial assay, where bacteria were pretreated for 2 h with the CIDAMP which had been dissolved in 20 µl of the respective test medium. Thereafter, 80 µl of growth medium (TSB) was added and the $OD_{620}$ determined after additional 6 hrs. The results are shown in FIG. 15.

As can be seen from FIG. 15, the addition of rhamnolipid at its CMC increases the potency of Pal-GR13 as well as of Pal-HR 1-11 2H2R-14 by more than factor 10. Furthermore, both CIDAMPs now were able to eradicate *S. aureus*. In contrast, when testing Pal-GR13 and Pal-HR 1-11 2H2R-14 in 10 mM phosphate buffer, pH 5.5, plus 0.25% glucose, containing rhamnolipid below its CMC (6 µg/ml), such an improvement was not seen (data not shown). Moreover, the addition of the biosurfactant rhamnolipid at 40 µg/ml to GR13 also did not lead to such an improvement (see FIG. 15).

Thus, the results show that adding an anionic detergent such as rhamnolipid, at its CMC to a palmitoylated CIDAMP is a strategy to improve the potency and efficacy of its antimicrobial activity.

Example 15: Description of Antimicrobial Assay Used for MIC-Determination

For MIC determination, bacteria were cultured in cation-adjusted Mueller Hinton broth (CAMHB) at 37° C. overnight. A sample of each culture was then diluted 40-fold in fresh broth and incubated at 37° C. for 1.5-3 h. The resultant mid-log phase cultures were diluted, then 45 µl was added to each well of the compound containing plates, giving a cell density of $5 \times 10^5$ CFU/ml and a final compound concentration of 32 µg/ml for the tested samples. All the plates were covered and incubated at 37° C. for 18 h.

Inhibition of bacterial growth was determined using resazurin as a marker for cell viability. Resazurin was added to each well, at 0.001% final concentration, and plates incubated at 37° C. for 2 h. Fluorescence intensity was measured, using F (top read), ex 560/10 nm, em 590/10 nm, using a Tecan M1000 Pro monochromator plate reader. The percentage of growth inhibition was calculated for each well, using the negative control (media only) and positive control (bacteria without inhibitors) on the same plate as references. The significance of the inhibition values was determined by Z-scores, calculated using the average and standard deviation of the sample wells (no controls) on the same plate. Samples were classed as actives with, inhibition value above 80% and Z-Score above 2.5, for either replicate (n=2 on different plates).

Example 16: Description of Antifungal Assay Used for MIC-Determination

For MIC determination, fungal strains were cultured for 3 days on Yeast Extract-Peptone Dextrose (YPD) agar at 30° C. A yeast suspension of $1 \times 10^6$ to $5 \times 10^6$ cells/ml was prepared from five colonies. These stock suspensions were diluted with Yeast Nitrogen Base (YNB) broth to a final concentration of $2.5 \times 10^3$ CFU/ml. Then, 45 µl of the fungi suspension was added to each well of the compound-containing plates, giving a final concentration of 32 µg/ml for the tested samples and a concentration range of 0.01 to 32 µg/ml for the antifungal control, fluconazole. Plates were covered and incubated at 35° C. for 24 h.

Growth inhibition of *C. albicans* was determined measuring absorbance at 530 nm (OD530), while the growth inhibition of *C. neoformans* was determined measuring the difference in absorbance between 600 and 570 nm (OD600-570), after the addition of resazurin (0.001% final concentration) and incubation at 35° C. for 2 h. The absorbance was measured using a Biotek Multiflo Synergy HTX plate reader. The percentage of growth inhibition was calculated for each well, using the negative control (media only) and positive control (bacteria without inhibitors) on the same plate. The significance of the inhibition values was determined by Z-scores, calculated using the average and standard deviation of the sample wells (no controls) on the same plate. Samples were classed as actives with, inhibition value above 80% and Z-Score above 2.5, for either replicate (n=2 on different plates).

Example 17: Cytotoxicity of Selected CIDAMPs

For the cytotoxicity (resazurin) assay, HEK293 cells were counted manually in a Neubauer haemocytometer and plated at a density of 4000 cells/well into each well of the 384-well plates containing the 25×(2 µl) concentrated compounds. The medium used was Dulbecco's modified eagle medium (DMEM) supplemented with 10% foetal bovine serum (FBS). Cells were incubated together with the compounds for 20 h at 37° C., 5% $CO_2$. To measure cytotoxicity, 5 µl (equals 100 µM final) resazurin was added to each well after incubation, and incubated for further 3 h at 37° C. with 5% $CO_2$.

After final incubation fluorescence intensity was measured as F ex 560/10 nm, em 590/10 nm (F560/590) using a Tecan M1000 Pro monochromator plate reader. CC50 values (concentration at 50% cytotoxicity) were calculated by normalizing the fluorescence readout, with 74 µg/ml tamoxifen as negative control (0%) and normal cell growth as positive control (100%). The concentration dependent percentage cytotoxicity was fitted to a dose response function (using Pipeline Pilot) and $CC_{50}$ values determined. Hits were classified as cytotoxic by CC50≤32 µg/ml in either replicate (n=2 on different plates).

Cytotoxicity values of selected CIDAMPs are presented in Table 27 and reveal no cytotoxicity at concentrations <32 µg/ml.

TABLE 27

Cytotoxicity and hemolytic activity of selected CIDAMPs

| Name | Sequence | SEQ ID NO: | Cytotoxicity (CC50, µg/ml) | Hemolysis (CC50, µg/ml) |
| --- | --- | --- | --- | --- |
| LCE2B$_{74-86}$ | SHHRPRLFHRRRH | 107 | >32 | >300 |
| LCE3B$_{56-68}$ | SHHRCCRSHRCRR | 20 | >32 | >300 |
| LCE3C$_{55-67}$ | SHHRHFRSHQCRR | 22 | >32 | >300 |
| LCE3C$_{55-75}$ | SHHRHFRSHQCRRQRSNSCDR | 110 | >32 | >300 |
| HR 1-18 HR | GRRGSGLGRSSSRGQRGSGSGR | 75 | >32 | >300 |
| Pal-HR 1-18 HR | Pal-GRRGSGLGRSSSRGQRGSGSGR | 5 | >32 | >300 |
| Pal-HR 1-11 2H2R-14 | Pal-RGSRSGQSSRGERR | 9 | >32 | >300 |
| Pal-GR13 | Pal-GRRGGRGGRGRGR | 18 | >32 | 100 |
| Pal-GR9 | Pal-GRRGGRGGR | 15 | >32 | >300 |
| Pal-GR4 | Pal-GRGR | 13 | >32 | 100 |
| Pal-GDap4 | Pal-GDapGDap | 12 | >32 | >300 |
| Pal-LCE3C$_{55-67}$ | Pal-SHHRHFRSHQCRR | 23 | >32 | >100 |
| Pal-LCE3B$_{56-68}$ | Pal-SHHRCCRSHRCRR | 21 | >32 | >100 |
| HR 1-18 | GRHGSGLGHSSSHGQHGSGSGR | 2 | >32 | >300 |
| Pal-HR 1-18 | Pal-GRHGSGLGHSSSHGQHGSGSGR | 3 | >32 | >300 |
| Myr-HR 1-18 | Myr-GRHGSGLGHSSSHGQHGSGSGR | 112 | 32 | >300 |
| Pal-HR 1-11 | Pal-HGSRSGQSSRGERHGSSSGSSSH | 8 | >32 | n.d. |
| Pal-HR 1-11 3H3R | Pal-RGSRSGQSSRGERRGSSSGSSSR | 10 | >32 | >300 |
| D-Pal-GR13 | Pal-GR$_D$R$_D$GGR$_D$GGR$_D$GR$_D$ | 19 | >32 | 65 |
| D-Pal-GR9 | Pal-GR$_D$R$_D$GGR$_D$GGR$_D$ | 29 | >32 | >100 |
| D-Pal-GR4 | Pal-GR$_D$GR$_D$ | 28 | >32 | 300 |
| D-Pal-GK4 | Pal-GK$_D$GK$_D$ | 26 | >32 | 40 |
| D-Pal-GOrn4 | Pal-GO$_D$GO$_D$ | 27 | >32 | 55 |
| Pal-HR 1-18 3H3R-GR13 | Pal-GRRGSGLGRSSSR | 6 | >32 | >300 |
| Pal-GOrn4 | Pal-GOGO | 116 | >32 | 80 |
| Pal-GDab4 | Pal-GDabGDab | 11 | 32 | >100 |
| Pal-GR6 | Pal-GRRGGR | 14 | >32 | >300 |
| Pal-Orn-GR13 | Pal-GOOGGOGGOGOGO | 121 | >32 | >300 |
| Pal-GK4 | Pal-GKGK | 115 | >32 | 50 |
| Pal-K-GR13 | Pal-GKKGGKGGKGKGK | 118 | >32 | >300 |
| Pal-GR11 | Pal-GRRGGRGGRGR | 16 | >32 | 90 |
| C-Pal-GR13 | GRRGGRGGRGRGR-C-Pal-NH2 | 25 | >32 | n.d. |
| LCE1B$_{78-88}$ | SHHRRRSHCH | 105 | >32 | n.d. |
| LCE2A$_{70-82}$ | SHHRPRLFHRHRH | 106 | >32 | n.d. |
| LCE3A$_{50-60}$ | SHHRCRRSHRC | 108 | >32 | n.d. |

TABLE 27-continued

Cytotoxicity and hemolytic activity of selected CIDAMPs

| Name | Sequence | SEQ ID NO: | Cytotoxicity (CC50, µg/ml) | Hemolysis (CC50, µg/ml) |
|---|---|---|---|---|
| LCE3C$_{55-66}$ | SHHRHFRSHQCR | 109 | >32 | n.d. |
| LCE3D$_{55-64}$ | NHHRRHHRCR | 111 | >32 | n.d. |

R$_D$, K$_D$, O$_D$-amino acids in D-form; O = Orn; Dab = (L)1,3-diaminobutyric acid; Dap = (L)1,3 diaminopropionic acid; n.d.: not determined

Example 18: Hemolytic Activity of Selected CIDAMPs

For the hemolysis assays EDTA-blood was centrifuged at 800×g for 10 min, and the plasma and buffy coat were removed. The erythrocytes were washed three times and resuspended in 5% PBS, pH 7.4. The cells were then incubated with end-over-end rotation for 1 h at 37° C. in the presence of different concentrations of peptides (0, 3, 10, 30, 60 µm). 0.1% Triton X-100 (Sigma-Aldrich) served as positive control. The samples were then centrifuged at 800×g for 10 min.

The absorbance of hemoglobin release was measured at 540 nm and is expressed as % of Triton X-100-induced hemolysis. These values of triplicates were plotted with Graph Pad Prism 4 as a dose response curve and the CC50 was determined.

No hemolytic activity was observed in any of the non-lipidated CIDAMPs (see Table 27). Interestingly, some highly antimicrobially active palmitoylated peptides like Pal-HR 1-18 and HR 1-18 3H3R GR13, Pal-Orn-GR13 and Pal-K-GR13, Pal-HR 1-18 HR, Pal-GDap4, nearly all S-Pal-HRNR-peptides and S-Pal-LCE3C$_{55-75}$ merely displayed low hemolytic activity, and only at high concentrations.

Example 19: Molecular Mechanism of CIDAMP Antimicrobial Activity

Figure 16:
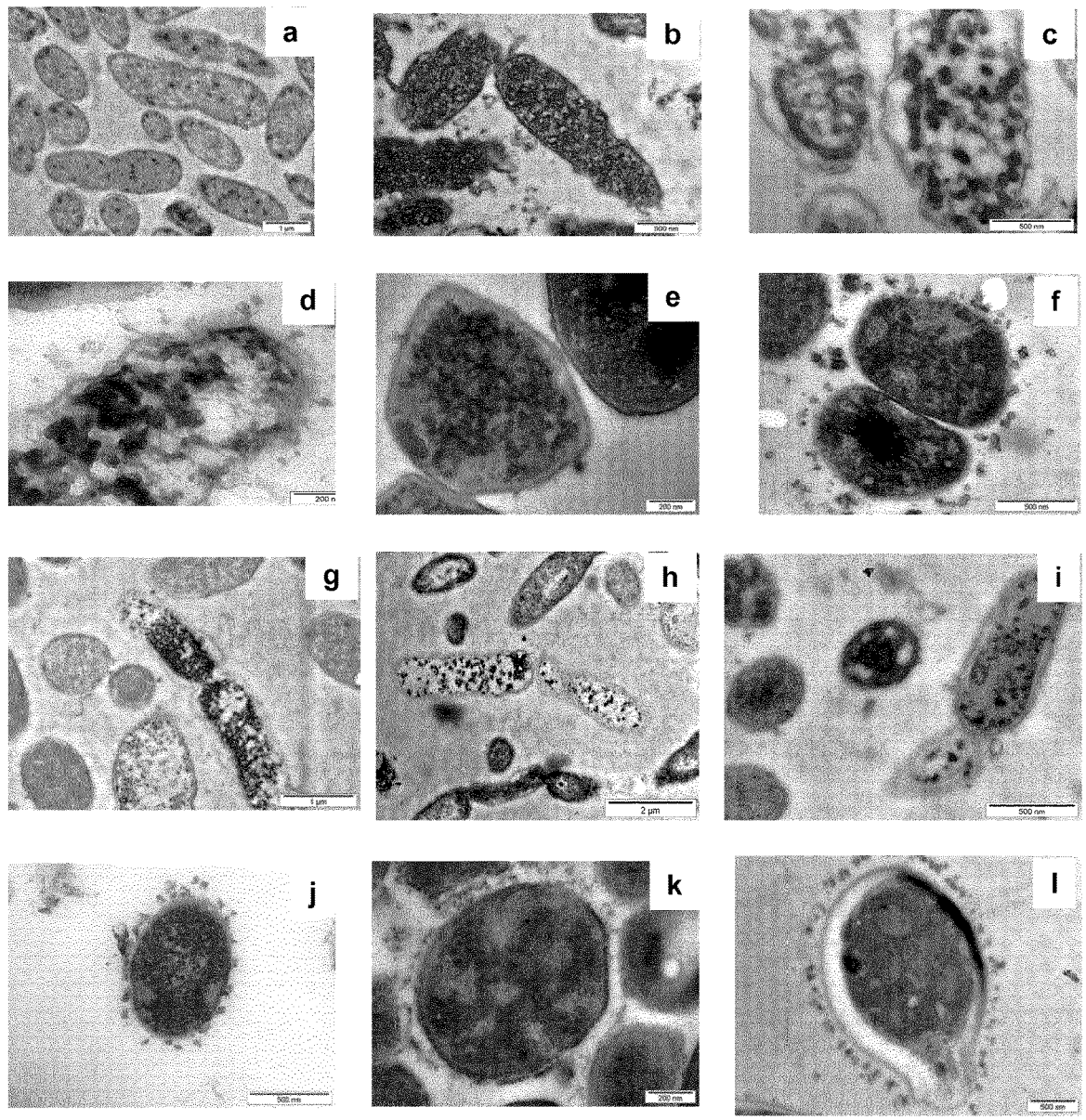
FIG. 16 shows transmission electron microscopy images of *P. aeruginosa* ATCC 10145 (a: control at pH 5.5; b: treated with gentamycin; c: treated with HR 1-18; d: treated with Pal-GR13), *S. aureus* ATCC 6538 (e: treated with Pal-LCE3B$_{56-68}$; f: treated with Pal-GR13), *E. coli* ATCC 11775 (g: treated with Pal-GR13); *B. cepacia* ATCC 25416 (h: treated with Pal-GR13); *P. oralis* ATCC 33321 (i: treated with Pal-GR13); *C. perfringens* ATCC 13124 (j: treated with Pal-GR13); *S. epidermidis* ATCC 14990 (k: treated with Pal-GR13); and *C. albicans* ATCC 24433 (I: treated with Pal-GR13)

To understand the mode of action of CIDAMP antimicrobial activity, ultrastructural changes were monitored in a number of bacterial species after treatment with various CIDAMPs and their N-palmitoyl-derivatives. Treatment of P. aeruginosa ATCC 10145 with HR 1-18 caused marked ultrastructural changes with electron-dense aggregates of ribosomes within the cells and, surprisingly, no signs of membrane alterations (see FIG. 16), which is one of the characteristics of amphipathic antimicrobial peptides like defensins.

Interestingly, when P. aeruginosa ATCC 10145 was treated with Pal-GR13, similar ribosome aggregates were observed. In addition, however, small membrane vesicles were visible (see FIG. 16). All bacterial species tested, which include, apart from P. aeruginosa, also E. coli, B. cepacia, P. oralis, C. perfringens, S. aureus and S. epidermidis, showed an aggregation of ribosomes after treatment with CIDAMPs (see FIG. 16) and when a palmitoylated CIDAMP was used, again the release of small membrane vesicles was observed (see FIG. 16). Likewise, Pal-GR13-treated C. albicans revealed these small vesicles (see FIG. 16).

In summary, morphological changes after treatment with CIDAMPs are unique and completely different from those known for amphipathic antimicrobial peptides, which are targeting the bacterial membrane. Ultrastructural changes of CIDAMP-treated bacteria show to some extent similarities with those of bacteria that were treated with gentamycin (see FIG. 16), an aminoglycoside targeting the ribosome, but not the membrane.

Example 20: CIDAMPs Target Bacterial Ribosomal Proteins

The question whether CIDAMP-dependent morphological changes in bacteria are direct or indirect was addressed by testing the hypothesis that CIDAMPs directly bind to ribosomes and ribosomal proteins. For this purpose, ribosomes of E. coli were separated and partially purified by SulfoLink®-coupling resin-chromatography (Maguire et al., 2008, RNA, 14, 188-195) followed by reversed phase high performance liquid chromatography (HPLC) using an Aeris 3.6 µm C18 widepore RP-HPLC column (Phenomenex) and an increasing gradient of acetonitrile (ACN, max.: 80% v/v) in aqueous 0.1% trifluoroacetic acid.

Aliquots of each HPLC fraction were lyophilized, the residues dissolved in 5 µl water each and then applied to a nitrocellulose membrane. After blocking with 5% bovine serum albumin in PBS and washing with PBS, biotinylated rhHRNR2591-2694, a 103 amino acid fragment of hornerin, (10 µg/ml) was added and incubated at 4° C. overnight. After 4-times washing, Strep-Tactin® (1:200; iba lifescience) in PBS was added, incubated for 1 h and then, after 6 times washing with PBS, substrate was added and the blots developed.

Figure 17:
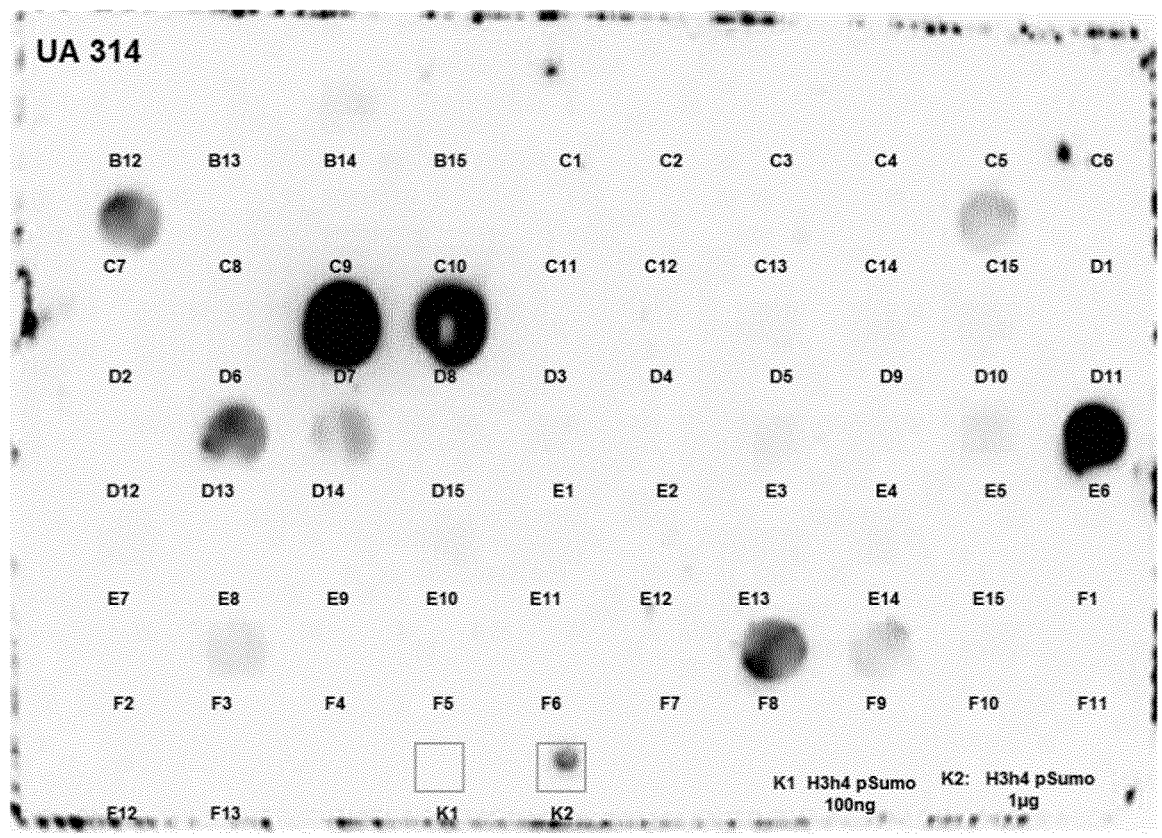
FIG. 17 shows an immunodotblot analysis of RP-18-HPLC-separated *E. coli*-ribosomal proteins with biotinylated recombinant HRNR$_{2591-2694}$.

The results indicate specific binding of biotinylated rhHRNR2591-2694 to certain ribosomal proteins (see FIG. 17). This was further confirmed by MS/MS-sequencing of biotinylated rhHRNR$_{2591-2694}$- and biotinylated HR1-bound ribosomal proteins: The E. coli 50S ribosomal proteins L2, L13, L18, L22, L28 as well as the E. coli 30S ribosomal proteins S3, S4, S11, S13, S16, S18, S19 and S20 were identified as targets of these biotinylated CIDAMPs. Using non-biotinylated CIDAMPs and anti-CIDAMP-antibodies for detection of CIDAMP-targeted ribosomal proteins revealed a very similar—if not identical—pattern of targeted ribosomal proteins.

Example 21: Selected CIDAMPs with Promising Potential

The most attractive CIDAMPs, with highest potential for further development, are listed in Tables 28-29. Some of them (HR 1-18, Pal-HR 1-18, Pal-HR 1-18 HR, HR 1-18 4H-4R, Pal-GR13, D-Pal-GR13, GR13, Pal-GR9 and FLG-2$_{2082-2100}$) are very potent P. aeruginosa ATCC 10145-cidal agents, at the same time displaying low (if any) cell toxicity and low (if any) hemolytic activity. Others (Pal-GR13, LCE3B$_{56-68}$ and Pal-LCE3B$_{56-68}$) represent optimized CIDAMP-derivatives with high potency and efficacy to kill S. aureus ATCC 6538 and also having low cytotoxicity and low hemolytic activity.

The main applications for the selected CIDAMPs are summarized in Table 30, depicted as "x", namely systemic treatment of bacterial infections including multi-resistant strains, topical treatment of S. aureus skin infections, mucosal (e.g. of the aero-digestive tract, vaginal) disinfection, disinfection of artificial surfaces, as alternative for classical antibiotics in animal feeds, for food conservation and for topical and systemic treatment of fungal infections.

TABLE 28

Properties of selected potent CIDAMPs

| SEQ ID NO. | Name | Sequence | P. aeruginosa MBC90 (μM) | P. aeruginosa MBC100 (μM) | S. aureus MBC90 (μM) | S. aureus MBC100 (μM) | Cytotox. CC50 (μM) | Hemolytic activity HC50 (μM) | CC50/MBC90 (P. aeruginosa) | CC50/MBC90 (S. aureus) |
|---|---|---|---|---|---|---|---|---|---|---|
| 1 | FLG-2$_{2082-2100}$ | HAHSGHGQSTQRGSRTAGR (SEQ ID NO: 1) | 0.010 (pH 5.5) | 0.076 (pH 5.5) | n.d. | n.d. | >12.9 | >121 | >1290 | n.a. |
| 2 | HR 1-18 | GRHGSGLGHSSSHGQHGSGSGR (SEQ ID NO: 2) | 0.009 (pH 5.5) | 0.036 (pH 5.5) | >143 (pH 5.5) | >143 (pH 5.5) | >15.2 | >143 | >1690 | No activity |
| 3 | Pal-HR 1-18 | Pal-GRHGSGLGHSSSHGQHGSGSGR (SEQ ID NO: 3) | 0.032 (pH 5.5) | 0.256 (pH 5.5) | 0.51 (pH 5.5) | 32 (pH 5.5) | >13.7 | >130 | >428 | >26.9 |
| 4 | HR 1-18 4H-4R | GRRGSGLGRSSSRGQRGSGSGR (SEQ ID NO: 5) | 0.018 (pH 5.5) | 0.142 (pH 5.5) | 4.46 (pH 7.0) | >143 (pH 7.0) | >15.2 | >150 | >844 | >3.4 |
| 5 | Pal-HR 1-18 HR | Pal-GRRGSGLGRSSSRGQRGSGSGR (SEQ ID NO: ) | 0.016 (pH 5.5) | 0.252 (pH 5.5) | 0.12 (pH 5.5) | 1.94 (pH 5.5) | >13.3 | >119 | >831 | >111 |
| 15 | Pal-GR9 | Pal-GRRGGRGGR (SEQ ID NO: 6) | 0.064 (pH 5.5) | 1.01 (pH 5.5) | 1.00 (pH 5.5) | 2.35 (pH 5.5) | >27.4 | >257 | >428 | >27.4 |
| 17 | GR13 | GRRGGRGRGRGR (SEQ ID NO: 17) | 0.028 (pH 5.5) | 0.055 (pH 5.5) | 5.54 (pH 5.5) | >55 (pH 5.5) | >23.6 | >220 | >843 | >4.3 |
| 18 | Pal-GR13 | Pal-GRRGGRGRGRGR (SEQ ID NO: 18) | 0.024 (pH 5.5) 0.18 (pH 7.3) | 0.188 (pH 5.5) 0.740 (pH 7.3) | 0.047 (pH 5.5) 0.19 (pH 7.3) | 0.192 (pH 5.5) 2.95 (pH 7.3) | >20.1 | — | >1333 (pH 5.5) >170 (pH 7.3) | >428 (pH 5.5) >106 (pH 7.3) |
| 19 | D-Pal-GR13 | Pal-GR$_D$R$_D$GGR$_D$GGR$_D$GR$_D$GR$_D$ (SEQ ID NO: 19) | 0.047 (pH 5.5) | 0.19 (pH 5.5) | 0.19 (pH 5.5) | 47 (pH 5.5) | >20.1 | 24.5 | >681 | >106 |
| 22 | LCE3B$_{56-68}$ | SHHRCCRSHRCRR (SEQ ID NO: 20) | n.d. | n.d. | 0.044 (pH 5.5) | >88.7 (pH 5.5) | >18.9 | >113 | — | >430 |
| 23 | Pal-LCE3B$_{56-68}$ | Pal-SHHRCCRSHRCRR (SEQ ID NO: 21) | 0.088 (pH 5.5) | 0.176 (pH 5.5) | 0.011 (pH 5.5) | 0.078 (pH 5.5) | >16.6 | >78 | >364 | >1509 |

MBC90: Microbicidal concentration killing 90% in the CFU-assay; MBC100: 100% killing in the CFU-assay; CC50: 50% cytotoxic concentration; HC50: conc. leading to 50% hemolysis with human erythrocytes; R$_D$-amino acid in D-form; n.d.: not determined

TABLE 29

Minimal inhibitory concentration (MIC in µg/ml) of selected CIDAMPs

| SEQ ID NO | Name | Sequence | A. baumannii ATCC 19606 | C. albicans ATCC 90028 | C. neoformans ATCC 208821 | E. coli ATCC 25922 | K. pneumoniae ATCC 700603 | P. aeruginosa ATCC 27853 | S. aureus ATCC 43300 |
|---|---|---|---|---|---|---|---|---|---|
| 1 | FLG-2$_{2082-2100}$ | HAHSGHGQSTQRGSRTAGR (SEQ ID NO: 1) | n.d. | n.d. | n.d. | n.d. | n.d. | * | n.d. |
| 2 | HR 1-18 | GRHGSGLGHSSSHGQHGSGSGR (SEQ ID NO: 2) | n.d. | n.d. | n.d. | n.d. | n.d. | * | n.d. |
| 3 | Pal-HR 1-18 | Pal-GRHGSGLGHSSSHGQHGSGSGR (SEQ ID NO: 3) | ≥32 | n.d. | n.d. | n.d. | n.d. | n.d. | n.d. |
| 4 | HR 1-18 4H-4R | GRRGSGLGRSSSRGQRGSGSGR (SEQ ID NO: 5) | n.d. | n.d. | n.d. | n.d. | n.d. | * | n.d. |
| 5 | Pal-HR 1-18 HR | Pal-GRRGSGLGRSSSRGQRGSGSGR (SEQ ID NO: 75) | ≥1 | n.d. | ≥1 | ≥4 | n.d. | ≥16 | ≥8 |
| 6 | Pal-HR 1-18 3H3R-GR13 | Pal-GRRGSGLGRSSSR (SEQ ID NO: 6) | ≥16 | n.d. | ≥16 | n.d. | n.d. | n.d. | ≥16 |
| 7 | Pal-HR 1-18 GR | Pal-GRRGGGGGRGGGRGGRGGGGGR (SEQ ID NO: 7) | n.d. | n.d. | n.d. | n.d. | n.d. | n.d. | n.d. |
| 8 | Pal-HR 1-11 | Pal-HGSRSGQSSRGERHGSSSGSSSH (SEQ ID NO: 8) | n.d. | n.d. | ≥8 | ≥8 | n.d. | n.d. | >32 |
| 9 | Pal-HR 1-11 2H2R-14 | Pal-RGSRSGQSSRGERR (SEQ ID NO: 9) | ≥4 | n.d. | n.d. | n.d. | n.d. | n.d. | ≥8 |
| 10 | Pal-HR 1-11 3H3R | Pal-RGSRSGQSSRGERRGSSSGSSSR (SEQ ID NO: 10) | ≥8 | ≥32 | ≥32 | ≥32 | n.d. | n.d. | >32 |
| 11 | Pal-GDab4 | Pal-GDabGDab (SEQ ID NO: 11) | ≥32 | n.d. | ≥16 | n.d. | n.d. | n.d. | ≥32 |
| 12 | Pal-GDap4 | Pal-GDapGDap (SEQ ID NO: 12) | n.d. | ≥8 | ≥1 | ≥8 | n.d. | n.d. | ≥8 |

TABLE 29-continued

Minimal inhibitory concentration (MIC in µg/ml) of selected CIDAMPs

| SEQ ID NO | Name | Sequence | A. baumannii ATCC 19606 | C. albicans ATCC 90028 | C. neoformans ATCC 208821 | E. coli ATCC 25922 | K. pneumoniae ATCC 700603 | P. aeruginosa ATCC 27853 | S. aureus ATCC 43300 |
|---|---|---|---|---|---|---|---|---|---|
| 13 | Pal-GR4 | Pal-GRGR (SEQ ID NO: 13) | n.d. | ≥8 | ≥8 | n.d. | n.d. | n.d. | ≥8 |
| 14 | Pal-GR6 | Pal-GRRGGR (SEQ ID NO: 14) | n.d. | n.d. | ≥16 | n.d. | n.d. | n.d. | ≥16 |
| 15 | Pal-GR9 | Pal-GRRGGRGRGGR (SEQ ID NO: 15) | n.d. | n.d. | n.d. | n.d. | n.d. | n.d. | ≥8 |
| 16 | Pal-GR11 | Pal-GRRGGRGRGGRGR (SEQ ID NO: 16) | ≥8 | ≥4 | ≥4 | ≥8 | n.d. | ≥16 | ≥4 |
| 17 | GR13 | GRRGGRGRGRGRGR (SEQ ID NO: 17) | * | n.d. | n.d. | * | n.d. | * | n.d. |
| 18 | Pal-GR13 | Pal-GRRGGRGRGGRGRGRGR (SEQ ID NO: 18) | ≥2 | ≥4 | ≥0.25 | ≥4 | ≥16 | ≥8 | ≥0.25 |
| 19 | D-Pal-GR13 | Pal-GR$_D$R$_D$GGR$_D$GGR$_D$GR$_D$GR$_D$ (SEQ ID NO: 114) | ≥8 | ≥8 | ≥2 | ≥8 | ≥32 | ≥16 | ≥2 |
| 20 | LCE3B5668 | SHHRCCRSHRCRR (SEQ ID NO: 20) | n.d. | n.d. | ≥8 | n.d. | n.d. | n.d. | ≥32 |
| 21 | Pal-LCE3B$_{56-68}$ | SHHRCCRSHRCRR (SEQ ID NO: 21) | n.d. | ≥1 | ≥0.25 | n.d. | n.d. | n.d. | ≥16 |
| 22 | LCE3C55 67 | SHHRHFRSHQCRR (SEQ ID NO: 22) | n.d. | n.d. | ≥8 | n.d. | n.d. | n.d. | ≥32 |
| 23 | Pal-LCE3C$_{55-67}$ | Pal-SHHRHFRSHQCRR (SEQ ID NO: 23) | n.d. | ≥16 | ≥1 | n.d. | n.d. | n.d. | ≥32 |

R$_D$-amino acid in D-form; Dab = (L)1,3-diaminobutyric acid; Dap = (L)1,3-diaminopropionic acid
*: not active in Mueller-Hinton medium; n.d.: not determined

TABLE 30

Potential applications of selected potent CIDAMPs

| SEQ ID NO | Name | Sequence | Systemic MR | Topical Skin | Mucosa | Surface-Disinfection | Food Feed | Fungi |
|---|---|---|---|---|---|---|---|---|
| 1 | FLG-2$_{2082-2100}$ | HAHSGHGQSTQRGSRTAGR (SEQ ID NO: 1) | | | x | x | | |
| 2 | HR 1-18 | GRHGSGLGHSSSHGQHGSGSGR (SEQ ID NO: 2) | | | x | x | | |
| 3 | Pal-HR 1-18 | Pal-GRHGSGLGHSSSHGQHGSGSGR (SEQ ID NO: 3) | | | x | x | | |
| 4 | HR 1-18 4H-4R | GRRGSGLGRSSSRGQRGSGSGR (SEQ ID NO: 5) | | | x | x | | |
| 5 | Pal-HR 1-18 HR | Pal-GRRGSGLGRSSSRGQRGSGSGR (SEQ ID NO: 75) | x | x | x | x | | x |
| 6 | Pal-HR 1-18 3H3R-GR13 | Pal-GRRGSGLGRSSSR (SEQ ID NO: 6) | x | | | | x | |
| 7 | Pal-HR 1-18 GR | Pal-GRRGGGGRGGGRGGRGGGGR (SEQ ID NO: 7) | | x | | | | |
| 8 | Pal-HR 1-11 | Pal-HGSRSGQSSRGERHGSSSGSSSH (SEQ ID NO: 8) | | x | | | | |
| 9 | Pal-HR 1-11 2H2R-14 | Pal-RGSRSGQSSRGERR (SEQ ID NO: 9) | x | x | x | | | x |
| 10 | Pal-HR 1-11 3H3R | Pal-RGSRSGQSSRGERRGSSSGSSSR (SEQ ID NO: 10) | x | x | | | | |
| 11 | Pal-GDab4 | Pal-GDabGDab (SEQ ID NO: 11) | x | | | | x | |
| 12 | Pal-GDap4 | Pal-GDapGDap (SEQ ID NO: 12) | x | | | | x | x |
| 13 | Pal-GR4 | Pal-GRGR (SEQ ID NO: 13) | x | | | | x | x |
| 14 | Pal-GR6 | Pal-GRRGGR (SEQ ID NO: 14) | x | | | | x | |
| 15 | Pal-GR9 | Pal-GRRGGRGGR (SEQ ID NO: 15) | | | x | x | x | x |
| 16 | Pal-GR11 | Pal-GRRGGRGGRGR (SEQ ID NO: 16) | x | | | | x | |
| 17 | GR13 | GRRGGRGGRGRGR (SEQ ID NO: 17) | | | x | x | x | |
| 18 | Pal-GR13 | Pal-GRRGGRGGRGRGR (SEQ ID NO: 18) | x | x | x | x | x | x |
| 19 | D-Pal-GR13 | Pal-GR$_D$R$_D$GGR$_D$GGR$_D$GR$_D$GR$_D$ (SEQ ID NO: 114) | x | x | x | x | x | x |
| 20 | LCE3B$_{56-68}$ | SHHRCCRSHRCRR (SEQ ID NO: 20) | x | x | x | x | | x |
| 21 | Pal-LCE3B$_{56-68}$ | Pal-SHHRCCRSHRCRR (SEQ ID NO: 21) | x | x | x | x | x | x |
| 22 | LCE3C$_{55-67}$ | SHHRHFRSHQCRR (SEQ ID NO: 22) | x | | | | | x |
| 23 | Pal-LCE3C$_{55-67}$ | Pal-SHHRHFRSHQCRR (SEQ ID NO: 23) | x | x | | | | x |

R$_D$-amino acid in D-form; Dab = (L)1,3-diaminobutyric acid; Dap = (L)1,3-diaminopropionic acid

The invention claimed is:

1. A composition comprising at least one antimicrobial peptide consisting of an amino acid sequence selected from the group consisting of SEQ ID NOs: 1 to 12, 14 to 25, 29 to 44, 47 to 48, 51, 53 to 114, and 117 to 130, or a variant thereof having antimicrobial activity and having sequence identity of at least 80% to an amino acid sequence selected from the group consisting of SEQ ID NOs: 1 to 12, 14 to 25, 29 to 44, 47 to 48, 51, 53 to 114, and 117 to 130, and a carrier selected from an emulsion, a liposome, a gel, a foam, a mousse, an ointment, a cream, and combinations thereof.

2. The composition of claim 1, wherein the peptide is N-palmitoylated, S-palmitoylated, O-palmitoylated, N-myristoylated, or any combination thereof.

3. The composition of claim 2, wherein the peptide is N-, S-, or O-palmitoylated.

4. A method for prevention or treatment of a bacterial or fungal infection in a subject, comprising administering to the subject the composition of claim 1.

5. The method of claim 4, wherein the bacterial or fungal infection is by *Staphylococcus aureus, Pseudomonas aeruginosa, Propionibacterium acnes, Streptococcus species, Klebsiella pneumoniae, Escherichia coli, Salmonella typhimurium, Acinetobacter baumannii, Clostridium species, Corynebacterium species, Burkholderia species, Candida species, Aspergillus species, Cryptococcus species*, or *Malassezia* species.

6. The method of claim 4, wherein the bacterial or fungal infection is a skin infection in atopic dermatitis, an acne or burn wound, an ulcer in psoriasis, an aero-digestive-tract infection, cystic fibrosis, pneumonia, sinusitis, an oral *Candida* species infection, caries, a chronic obstructive pulmonary disease, an infection of the eye, *Pseudomonas* keratitis of the cornea, otitis, a vaginal infection, a genito-urinary tract infection, an inflammatory bowel disease, an infection by *Cryptococcus neoformans*, mastitis in cattle, or an infection by *Paenibacillus* larvae.

7. A method of cosmetic usage in a subject in need thereof, comprising administering the composition of claim 1 to the subject.

8. A method for sterilizing a surface, comprising applying the composition of claim 1 to the surface.

9. The method of claim 8, wherein the composition is formulated as a preservative, disinfectant, antiseptic, or an agent of biocontrol.

* * * * *

SEQUENCE LISTING

<160> NUMBER OF SEQ ID NOS: 135

<210> SEQ ID NO 1
<211> LENGTH: 19
<212> TYPE: PRT
<213> ORGANISM: Artificial Sequence

```
<220> FEATURE:
<223> OTHER INFORMATION: Peptide derived from human filaggrin-2 (FLG-2
      2082-2100)

<400> SEQUENCE: 1

His Ala His Ser Gly His Gly Gln Ser Thr Gln Arg Gly Ser Arg Thr
1               5                   10                  15

Ala Gly Arg

<210> SEQ ID NO 2
<211> LENGTH: 22
<212> TYPE: PRT
<213> ORGANISM: Artificial Sequence
<220> FEATURE:
<223> OTHER INFORMATION: Peptide derived from human hornerin (HR 1-18)

<400> SEQUENCE: 2

Gly Arg His Gly Ser Gly Leu Gly His Ser Ser Ser His Gly Gln His
1               5                   10                  15

Gly Ser Gly Ser Gly Arg
            20

<210> SEQ ID NO 3
<211> LENGTH: 22
<212> TYPE: PRT
<213> ORGANISM: Artificial Sequence
<220> FEATURE:
<223> OTHER INFORMATION: Palmitoylated peptide derived from human
      hornerin (Pal-HR 1-18)

<400> SEQUENCE: 3

Gly Arg His Gly Ser Gly Leu Gly His Ser Ser Ser His Gly Gln His
1               5                   10                  15

Gly Ser Gly Ser Gly Arg
            20

<210> SEQ ID NO 4
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 4H-4R)

<400> SEQUENCE: 4

Gly Arg Arg Gly Ser Gly Leu Gly Arg Ser Ser Ser Arg Gly Gly Arg
1               5                   10                  15

Gly Ser Gly Ser Gly Arg
            20

<210> SEQ ID NO 5
<211> LENGTH: 22
<212> TYPE: PRT
<213> ORGANISM: Artificial Sequence
<220> FEATURE:
<223> OTHER INFORMATION: Palmitoylated modified peptide derived from
      human hornerin (Pal-HR 1-18 HR)
<220> FEATURE:
<221> NAME/KEY: LIPID
<222> LOCATION: (1)..(1)
<223> OTHER INFORMATION: PALMITATE

<400> SEQUENCE: 5

Gly Arg Arg Gly Ser Gly Leu Gly Arg Ser Ser Ser Arg Gly Gln Arg
1               5                   10                  15
```

```
Gly Ser Gly Ser Gly Arg
            20

<210> SEQ ID NO 6
<211> LENGTH: 13
<212> TYPE: PRT
<213> ORGANISM: Artificial Sequence
<220> FEATURE:
<223> OTHER INFORMATION: Palmitoylated modified peptide derived from
      human hornerin (Pal-HR 1-18 3H3R-GR13)
<220> FEATURE:
<221> NAME/KEY: LIPID
<222> LOCATION: (1)..(1)
<223> OTHER INFORMATION: PALMITATE

<400> SEQUENCE: 6

Gly Arg Arg Gly Ser Gly Leu Gly Arg Ser Ser Ser Arg
1               5                   10

<210> SEQ ID NO 7
<211> LENGTH: 22
<212> TYPE: PRT
<213> ORGANISM: Artificial Sequence
<220> FEATURE:
<223> OTHER INFORMATION: Palmitoylated cationic intrinsically disordered
      antimicrobial peptide (Pal-HR 1-18 GR)
<220> FEATURE:
<221> NAME/KEY: LIPID
<222> LOCATION: (1)..(1)
<223> OTHER INFORMATION: PALMITATE

<400> SEQUENCE: 7

Gly Arg Arg Gly Gly Gly Gly Arg Gly Gly Gly Arg Gly Gly Arg
1               5                   10                  15

Gly Gly Gly Gly Gly Arg
            20

<210> SEQ ID NO 8
<211> LENGTH: 23
<212> TYPE: PRT
<213> ORGANISM: Artificial Sequence
<220> FEATURE:
<223> OTHER INFORMATION: Palmitoylated peptide derived from human
      hornerin (Pal-HR 1-11)
<220> FEATURE:
<221> NAME/KEY: LIPID
<222> LOCATION: (1)..(1)
<223> OTHER INFORMATION: PALMITATE

<400> SEQUENCE: 8

His Gly Ser Arg Ser Gly Gln Ser Ser Arg Gly Glu Arg His Gly Ser
1               5                   10                  15

Ser Ser Gly Ser Ser Ser His
            20

<210> SEQ ID NO 9
<211> LENGTH: 14
<212> TYPE: PRT
<213> ORGANISM: Artificial Sequence
<220> FEATURE:
<223> OTHER INFORMATION: Palmitoylated modified peptide derived from
      human hornerin (Pal-HR 1-11 2H2R-14)
<220> FEATURE:
<221> NAME/KEY: LIPID
<222> LOCATION: (1)..(1)
<223> OTHER INFORMATION: PALMITATE

<400> SEQUENCE: 9

Arg Gly Ser Arg Ser Gly Gln Ser Ser Arg Gly Glu Arg Arg
```

<210> SEQ ID NO 10
<211> LENGTH: 23
<212> TYPE: PRT
<213> ORGANISM: Artificial Sequence
<220> FEATURE:
<223> OTHER INFORMATION: Palmitoylated modified peptide derived from
      human hornerin (Pal-HR 1-11 3H3R)
<220> FEATURE:
<221> NAME/KEY: LIPID
<222> LOCATION: (1)..(1)
<223> OTHER INFORMATION: PALMITATE

<400> SEQUENCE: 10

Arg Gly Ser Arg Ser Gly Gln Ser Ser Arg Gly Glu Arg Arg Gly Ser
1               5                   10                  15

Ser Ser Gly Ser Ser Ser Arg
            20

<210> SEQ ID NO 11
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GDab4)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(2)
<223> OTHER INFORMATION: (L)1,3-diaminobutyric acid
<220> FEATURE:
<221> NAME/KEY: MISC_FEATURE
<222> LOCATION: (4)..(4)
<223> OTHER INFORMATION: (L)1,3-diaminobutyric acid

<400> SEQUENCE: 11

Gly Xaa Gly Xaa
1

<210> SEQ ID NO 12
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GDap4)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(2)
<223> OTHER INFORMATION: (L)1,3-diaminopropionic acid
<220> FEATURE:
<221> NAME/KEY: MISC_FEATURE
<222> LOCATION: (4)..(4)
<223> OTHER INFORMATION: (L)1,3-diaminopropionic acid

<400> SEQUENCE: 12

Gly Xaa Gly Xaa
1

<210> SEQ ID NO 13
<211> LENGTH: 4
<212> TYPE: PRT

<213> ORGANISM: Artificial Sequence
<220> FEATURE:
<223> OTHER INFORMATION: Palmitoylated synthetic cationic intrinsically
      disordered antimicrobial peptide (Pal-GR4)
<220> FEATURE:
<221> NAME/KEY: LIPID
<222> LOCATION: (1)..(1)
<223> OTHER INFORMATION: PALMITATE

<400> SEQUENCE: 13

Gly Arg Gly Arg
1

<210> SEQ ID NO 14
<211> LENGTH: 6
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GR6)
<220> FEATURE:
<221> NAME/KEY: LIPID
<222> LOCATION: (1)..(1)
<223> OTHER INFORMATION: PALMITATE

<400> SEQUENCE: 14

Gly Arg Arg Gly Gly Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GR9)
<220> FEATURE:
<221> NAME/KEY: LIPID
<222> LOCATION: (1)..(1)
<223> OTHER INFORMATION: PALMITATE

<400> SEQUENCE: 15

Gly Arg Arg Gly Gly Arg Gly Gly Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GR11)
<220> FEATURE:
<221> NAME/KEY: LIPID
<222> LOCATION: (1)..(1)
<223> OTHER INFORMATION: PALMITATE

<400> SEQUENCE: 16

Gly Arg Arg Gly Gly Arg Gly Gly Arg Gly Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic cationic intrinsically disordered
      antimicrobial peptide (GR13)
<220> FEATURE:
<221> NAME/KEY: LIPID
<222> LOCATION: (1)..(1)

<223> OTHER INFORMATION: PALMITATE

<400> SEQUENCE: 17

Gly Arg Arg Gly Gly Arg Gly Gly Arg Gly Arg Gly Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GR13)
<220> FEATURE:
<221> NAME/KEY: LIPID
<222> LOCATION: (1)..(1)
<223> OTHER INFORMATION: PALMITATE

<400> SEQUENCE: 18

Gly Arg Arg Gly Gly Arg Gly Gly Arg Gly Arg Gly Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic cationic intrinsically disordered
      antimicrobial peptide (D-Pal-GR13)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid
<220> FEATURE:
<221> NAME/KEY: MISC_FEATURE
<222> LOCATION: (11)..(11)
<223> OTHER INFORMATION: D-amino acid
<220> FEATURE:
<221> NAME/KEY: MISC_FEATURE
<222> LOCATION: (13)..(13)
<223> OTHER INFORMATION: D-amino acid

<400> SEQUENCE: 19

Gly Arg Arg Gly Gly Arg Gly Gly Arg Gly Arg Gly Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Peptide derived from human late cornified
      envelope protein 3B (LCE3B 56-68)

<400> SEQUENCE: 20

Ser His His Arg Cys Cys Arg Ser His Arg Cys Arg Arg
1               5                   10

<210> SEQ ID NO 21

```
<211> LENGTH: 13
<212> TYPE: PRT
<213> ORGANISM: Artificial Sequence
<220> FEATURE:
<223> OTHER INFORMATION: Palmitoylated peptide derived from late
      cornified envelope protein 3B (Pal-LCE3B 56-68)
<220> FEATURE:
<221> NAME/KEY: LIPID
<222> LOCATION: (1)..(1)
<223> OTHER INFORMATION: PALMITATE

<400> SEQUENCE: 21

Ser His His Arg Cys Cys Arg Ser His Arg Cys Arg Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Peptide derived from human late cornified
      envelope protein 3C (LCE3C 55-67)

<400> SEQUENCE: 22

Ser His His Arg His Phe Arg Ser His Gln Cys Arg Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Palmitoylated peptide derived from human late
      cornified envelope protein 3C (Pal-LCE3C 55-67)
<220> FEATURE:
<221> NAME/KEY: LIPID
<222> LOCATION: (1)..(1)
<223> OTHER INFORMATION: PALMITATE (AMIDE BOND)

<400> SEQUENCE: 23

Ser His His Arg His Phe Arg Ser His Gln Cys Arg Arg
1               5                   10

<210> SEQ ID NO 24
<211> LENGTH: 22
<212> TYPE: PRT
<213> ORGANISM: Artificial Sequence
<220> FEATURE:
<223> OTHER INFORMATION: Biotinylated peptide derived from human
      hornerin (Biotin-HR 1-18)
<220> FEATURE:
<221> NAME/KEY: MISC_FEATURE
<222> LOCATION: (1)..(1)
<223> OTHER INFORMATION: Biotin

<400> SEQUENCE: 24

Gly Arg His Gly Ser Gly Leu Gly His Ser Ser His Gly Gln His
1               5                   10                  15

Gly Ser Gly Ser Gly Arg
            20

<210> SEQ ID NO 25
<211> LENGTH: 14
<212> TYPE: PRT
<213> ORGANISM: Artificial Sequence
<220> FEATURE:
<223> OTHER INFORMATION: C-palmitoylated synthetic cationic
      intrinsically disordered antimicrobial peptide (C-Pal-GR13)
<220> FEATURE:
<221> NAME/KEY: LIPID
```

```
<222> LOCATION: (14)..(14)
<223> OTHER INFORMATION: PALMITATE
<220> FEATURE:
<221> NAME/KEY: MOD_RES
<222> LOCATION: (14)..(14)
<223> OTHER INFORMATION: AMIDATION

<400> SEQUENCE: 25

Gly Arg Arg Gly Gly Arg Gly Gly Arg Gly Arg Gly Arg Cys
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (D-Pal-GK4)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid

<400> SEQUENCE: 26

Gly Lys Gly Lys
1

<210> SEQ ID NO 27
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (D-Pal-GOrn4)
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (2)..(2)
<223> OTHER INFORMATION: Orn (D-amino acid)
<220> FEATURE:
<221> NAME/KEY: MOD_RES
<222> LOCATION: (4)..(4)
<223> OTHER INFORMATION: Orn (D-amino acid)

<400> SEQUENCE: 27

Gly Xaa Gly Xaa
1

<210> SEQ ID NO 28
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (D-Pal-GR4)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(2)
```

```
<223> OTHER INFORMATION: D-amino aicd
<220> FEATURE:
<221> NAME/KEY: MISC_FEATURE
<222> LOCATION: (4)..(4)
<223> OTHER INFORMATION: D-amino aicd

<400> SEQUENCE: 28

Gly Arg Gly Arg
1

<210> SEQ ID NO 29
<211> LENGTH: 9
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (D-Pal-GR9)
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid

<400> SEQUENCE: 29

Gly Arg Arg Gly Gly Arg Gly Gly Arg
1               5

<210> SEQ ID NO 30
<211> LENGTH: 22
<212> TYPE: PRT
<213> ORGANISM: Artificial Sequence
<220> FEATURE:
<223> OTHER INFORMATION: FITC-labeled peptide derived from human
      hornerin (FITC-HR 1-18)
<220> FEATURE:
<221> NAME/KEY: MISC_FEATURE
<222> LOCATION: (1)..(1)
<223> OTHER INFORMATION: FITC (fluorescein isothiocyanate)

<400> SEQUENCE: 30

Gly Arg His Gly Ser Gly Leu Gly His Ser Ser Ser His Gly Gln His
1               5                   10                  15

Gly Ser Gly Ser Gly Arg
            20

<210> SEQ ID NO 31
<211> LENGTH: 25
<212> TYPE: PRT
<213> ORGANISM: Artificial Sequence
<220> FEATURE:
<223> OTHER INFORMATION: Peptide derived from human filaggrin-2 (FLG-2
      1515-1539)

<400> SEQUENCE: 31

His Thr His Ser Gly His Thr His Gly Gln Ser Gly Ser Gln His Gly
1               5                   10                  15

Glu Ser Glu Ser Ile Ile His Asp Arg
            20                  25
```

<210> SEQ ID NO 32
<211> LENGTH: 25
<212> TYPE: PRT
<213> ORGANISM: Artificial Sequence
<220> FEATURE:
<223> OTHER INFORMATION: Peptide derived from human filaggrin-2 (FLG-2 1742-1766)

<400> SEQUENCE: 32

His Thr His Ser Gly His Thr His Gly Gln Ala Arg Ser Gln His Gly
1               5                   10                  15

Glu Ser Glu Ser Ile Val His Glu Arg
            20                  25

<210> SEQ ID NO 33
<211> LENGTH: 25
<212> TYPE: PRT
<213> ORGANISM: Artificial Sequence
<220> FEATURE:
<223> OTHER INFORMATION: Peptide derived from human filaggrin-2 (FLG-2 1894-1918)

<400> SEQUENCE: 33

His Thr His Ser Gly His Thr His Ser Gln Ala Arg Ser Gln His Gly
1               5                   10                  15

Glu Ser Glu Ser Thr Val His Lys Arg
            20                  25

<210> SEQ ID NO 34
<211> LENGTH: 25
<212> TYPE: PRT
<213> ORGANISM: Artificial Sequence
<220> FEATURE:
<223> OTHER INFORMATION: Peptide derived from human filaggrin-2 (FLG-2 1969-1993)

<400> SEQUENCE: 34

His Thr His Ser Gly His Thr His Gly Gln Ala Gly Ser His Tyr Pro
1               5                   10                  15

Glu Ser Gly Ser Ser Val His Glu Arg
            20                  25

<210> SEQ ID NO 35
<211> LENGTH: 25
<212> TYPE: PRT
<213> ORGANISM: Artificial Sequence
<220> FEATURE:
<223> OTHER INFORMATION: Peptide derived from human filaggrin-2 (FLG-2 2044-2068)

<400> SEQUENCE: 35

His Thr His Ser Gly His Ala His Gly Gln Ala Gly Ser Gln His Gly
1               5                   10                  15

Glu Ser Gly Ser Ser Val His Glu Arg
            20                  25

<210> SEQ ID NO 36
<211> LENGTH: 12
<212> TYPE: PRT
<213> ORGANISM: Artificial Sequence
<220> FEATURE:
<223> OTHER INFORMATION: Peptide derived from human filaggrin-2 (FLG-2 2082-2093)

<400> SEQUENCE: 36

His Ala His Ser Gly His Gly Gln Ser Thr Gln Arg
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Peptide derived from human filaggrin-2 (FLG-2
      2082-2096)

<400> SEQUENCE: 37

His Ala His Ser Gly His Gly Gln Ser Thr Gln Arg Gly Ser Arg
1               5                   10                  15

<210> SEQ ID NO 38
<211> LENGTH: 24
<212> TYPE: PRT
<213> ORGANISM: Artificial Sequence
<220> FEATURE:
<223> OTHER INFORMATION: Peptide derived from human filaggrin-2 (FLG-2
      2082-2105)

<400> SEQUENCE: 38

His Ala His Ser Gly His Gly Gln Ser Thr Gln Arg Gly Ser Arg Thr
1               5                   10                  15

Ala Gly Arg Arg Gly Ser Gly His
            20

<210> SEQ ID NO 39
<211> LENGTH: 19
<212> TYPE: PRT
<213> ORGANISM: Artificial Sequence
<220> FEATURE:
<223> OTHER INFORMATION: Peptide derived from human filaggrin-2 (FLG-2
      2087-2105)

<400> SEQUENCE: 39

His Gly Gln Ser Thr Gln Arg Gly Ser Arg Thr Ala Gly Arg Arg Gly
1               5                   10                  15

Ser Gly His

<210> SEQ ID NO 40
<211> LENGTH: 12
<212> TYPE: PRT
<213> ORGANISM: Artificial Sequence
<220> FEATURE:
<223> OTHER INFORMATION: Peptide derived from human filaggrin-2 (FLG-2
      2094-2105)

<400> SEQUENCE: 40

Gly Ser Arg Thr Ala Gly Arg Arg Gly Ser Gly His
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Peptide derived from human filaggrin-2 (FLG-2
      2097-2105)

<400> SEQUENCE: 41

Thr Ala Gly Arg Arg Gly Ser Gly His
1               5

```
<210> SEQ ID NO 42
<211> LENGTH: 24
<212> TYPE: PRT
<213> ORGANISM: Artificial Sequence
<220> FEATURE:
<223> OTHER INFORMATION: Peptide derived from human filaggrin-2 (FLG-2
      2232-2255)

<400> SEQUENCE: 42

His Ala His Tyr Gly Tyr Gly Gln Ser Thr Gln Arg Gly Ser Arg Thr
1               5                   10                  15

Thr Gly Arg Arg Gly Ser Gly His
            20

<210> SEQ ID NO 43
<211> LENGTH: 27
<212> TYPE: PRT
<213> ORGANISM: Artificial Sequence
<220> FEATURE:
<223> OTHER INFORMATION: Peptide derived from human filaggrin (FLG
      528-554)

<400> SEQUENCE: 43

Gln Gly Ser His His Glu Gln Ser Val Asn Arg Ser Gly His Ser Gly
1               5                   10                  15

Ser His His Ser His Thr Thr Ser Gln Gly Arg
            20                  25

<210> SEQ ID NO 44
<211> LENGTH: 13
<212> TYPE: PRT
<213> ORGANISM: Artificial Sequence
<220> FEATURE:
<223> OTHER INFORMATION: Synthetic cationic intrinsically disordered
      antimicrobial peptide (GH13)

<400> SEQUENCE: 44

Gly His His Gly Gly His Gly Gly His Gly His Gly His
1               5                   10

<210> SEQ ID NO 45
<211> LENGTH: 3
<212> TYPE: PRT
<213> ORGANISM: Artificial Sequence
<220> FEATURE:
<223> OTHER INFORMATION: Synthetic cationic intrinsically disordered
      antimicrobial peptide (GH3)

<400> SEQUENCE: 45

His Gly His
1

<210> SEQ ID NO 46
<211> LENGTH: 5
<212> TYPE: PRT
<213> ORGANISM: Artificial Sequence
<220> FEATURE:
<223> OTHER INFORMATION: Synthetic cationic intrinsically disordered
      antimicrobial peptide (GH5)

<400> SEQUENCE: 46

His Gly His Gly His
1               5

<210> SEQ ID NO 47
<211> LENGTH: 7
<212> TYPE: PRT
```

```
<213> ORGANISM: Artificial Sequence
<220> FEATURE:
<223> OTHER INFORMATION: Synthetic cationic intrinsically disordered
      antimicrobial peptide (GH7)

<400> SEQUENCE: 47

His Gly His Gly His Gly His
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic cationic intrinsically disordered
      antimicrobial peptide (GH9)

<400> SEQUENCE: 48

His Gly His Gly His Gly His Gly His
1               5

<210> SEQ ID NO 49
<211> LENGTH: 3
<212> TYPE: PRT
<213> ORGANISM: Artificial Sequence
<220> FEATURE:
<223> OTHER INFORMATION: Synthetic cationic intrinsically disordered
      antimicrobial peptide (GR3)

<400> SEQUENCE: 49

Arg Gly Arg
1

<210> SEQ ID NO 50
<211> LENGTH: 5
<212> TYPE: PRT
<213> ORGANISM: Artificial Sequence
<220> FEATURE:
<223> OTHER INFORMATION: Synthetic cationic intrinsically disordered
      antimicrobial peptide (GR5)

<400> SEQUENCE: 50

Arg Gly Arg Gly Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic cationic intrinsically disordered
      antimicrobial peptide (GR7)

<400> SEQUENCE: 51

Arg Gly Arg Gly Arg Gly Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic cationic intrinsically disordered
      antimicrobial peptide (GR9)

<400> SEQUENCE: 52

Arg Gly Arg Gly Arg Gly Arg Gly Arg
1               5
```

<210> SEQ ID NO 53
<211> LENGTH: 23
<212> TYPE: PRT
<213> ORGANISM: Artificial Sequence
<220> FEATURE:
<223> OTHER INFORMATION: Peptide derived from human hornerin (HR 1-11)

<400> SEQUENCE: 53

His Gly Ser Arg Ser Gly Gln Ser Ser Arg Gly Glu Arg His Gly Ser
1               5                   10                  15

Ser Ser Gly Ser Ser Ser His
            20

<210> SEQ ID NO 54
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 3H3R)

<400> SEQUENCE: 54

Arg Gly Ser Arg Ser Gly Gln Ser Ser Arg Gly Glu Arg Arg Gly Ser
1               5                   10                  15

Ser Ser Gly Ser Ser Ser Arg
            20

<210> SEQ ID NO 55
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 E-G E2617G)

<400> SEQUENCE: 55

His Gly Ser Arg Ser Gly Gln Ser Ser Gly Gly Gly Arg His Gly Ser
1               5                   10                  15

Ser Ser Gly Ser Ser Ser His
            20

<210> SEQ ID NO 56
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 H1-GH2606G))

<400> SEQUENCE: 56

Gly Gly Ser Arg Ser Gly Gln Ser Ser Arg Gly Glu Arg His Gly Ser
1               5                   10                  15

Ser Ser Gly Ser Ser Ser His
            20

<210> SEQ ID NO 57
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 H2-G H2619G)

<400> SEQUENCE: 57

His Gly Ser Arg Ser Gly Gln Ser Ser Arg Gly Glu Arg Gly Gly Ser
1               5                   10                  15

Ser Ser Gly Ser Ser Ser His
            20

<210> SEQ ID NO 58
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 H3-G H2628G)

<400> SEQUENCE: 58

His Gly Ser Arg Ser Gly Gln Ser Ser Arg Gly Glu Arg His Gly Ser
1               5                   10                  15

Ser Ser Gly Ser Ser Ser Gly
            20

<210> SEQ ID NO 59
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 R1-G R2609G)

<400> SEQUENCE: 59

His Gly Ser Gly Ser Gly Gln Ser Ser Arg Gly Glu Arg His Gly Ser
1               5                   10                  15

Ser Ser Gly Ser Ser Ser His
            20

<210> SEQ ID NO 60
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 R2-G R2615G)

<400> SEQUENCE: 60

His Gly Ser Arg Ser Gly Gln Ser Ser Gly Gly Glu Arg His Gly Ser
1               5                   10                  15

Ser Ser Gly Ser Ser Ser His
            20

<210> SEQ ID NO 61
<211> LENGTH: 23
<212> TYPE: PRT
<213> ORGANISM: Artificial Sequence
<220> FEATURE:
<223> OTHER INFORMATION: Modified peptide derived from human hornerin
      (HR 1-11 R3-G R2618G)

<400> SEQUENCE: 61

His Gly Ser Arg Ser Gly Gln Ser Ser Arg Gly Glu Gly His Gly Ser
1               5                   10                  15

Ser Ser Gly Ser Ser Ser His
            20

<210> SEQ ID NO 62
<211> LENGTH: 14
<212> TYPE: PRT
<213> ORGANISM: Artificial Sequence

```
<220> FEATURE:
<223> OTHER INFORMATION: Modified peptide derived from human hornerin
      (HR 1-11s 2H2R-14)

<400> SEQUENCE: 62

Arg Gly Ser Arg Ser Gly Gln Ser Ser Arg Gly Glu Arg Arg
1               5                   10

<210> SEQ ID NO 63
<211> LENGTH: 19
<212> TYPE: PRT
<213> ORGANISM: Artificial Sequence
<220> FEATURE:
<223> OTHER INFORMATION: Modified peptide derived from human hornerin
      (HR 1-16 HRNR 2633-2651)

<400> SEQUENCE: 63

Gly Ser Gly Ser Arg Gln Ser Ser Gly His Gly Arg Gln Gly Ser Gly
1               5                   10                  15

Ser Gly Gln

<210> SEQ ID NO 64
<211> LENGTH: 29
<212> TYPE: PRT
<213> ORGANISM: Artificial Sequence
<220> FEATURE:
<223> OTHER INFORMATION: Peptide derived from human hornerin (HR 1-17)

<400> SEQUENCE: 64

Gly Arg His Gly Ser Gly Leu Gly His Ser Ser Ser His Gly Gln His
1               5                   10                  15

Gly Ser Gly Ser Gly Arg Ser Ser Ser Arg Gly Pro Tyr
            20                  25

<210> SEQ ID NO 65
<211> LENGTH: 29
<212> TYPE: PRT
<213> ORGANISM: Artificial Sequence
<220> FEATURE:
<223> OTHER INFORMATION: Modified peptide derived from human hornerin
      (HR 1-17 R2657G)

<400> SEQUENCE: 65

Gly Gly His Gly Ser Gly Leu Gly His Ser Ser Ser His Gly Gln His
1               5                   10                  15

Gly Ser Gly Ser Gly Arg Ser Ser Ser Arg Gly Pro Tyr
            20                  25

<210> SEQ ID NO 66
<211> LENGTH: 29
<212> TYPE: PRT
<213> ORGANISM: Artificial Sequence
<220> FEATURE:
<223> OTHER INFORMATION: Modified peptide derived from human hornerin
      (HR 1-17 R2677G)

<400> SEQUENCE: 66

Gly Arg His Gly Ser Gly Leu Gly His Ser Ser Ser His Gly Gln His
1               5                   10                  15

Gly Ser Gly Ser Gly Gly Ser Ser Ser Arg Gly Pro Tyr
            20                  25

<210> SEQ ID NO 67
<211> LENGTH: 29
<212> TYPE: PRT
```

```
<213> ORGANISM: Artificial Sequence
<220> FEATURE:
<223> OTHER INFORMATION: Modified peptide derived from human hornerin
      (HR 1-17 R2681G)

<400> SEQUENCE: 67

Gly Arg His Gly Ser Gly Leu Gly His Ser Ser His Gly Gln His
1               5                   10                  15

Gly Ser Gly Ser Gly Arg Ser Ser Ser Gly Gly Pro Tyr
            20                  25

<210> SEQ ID NO 68
<211> LENGTH: 29
<212> TYPE: PRT
<213> ORGANISM: Artificial Sequence
<220> FEATURE:
<223> OTHER INFORMATION: Modified peptide derived from human hornerin
      (HR 1-17 4H-4G all H vs G)

<400> SEQUENCE: 68

Gly Arg Gly Gly Ser Gly Leu Gly Gly Ser Ser Gly Gly Gln Gly
1               5                   10                  15

Gly Ser Gly Ser Gly Arg Ser Ser Ser Arg Gly Pro Tyr
            20                  25

<210> SEQ ID NO 69
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 4H-4R/9G-9S)

<400> SEQUENCE: 69

Ser Arg Arg Ser Ser Ser Leu Ser Arg Ser Ser Arg Ser Ser Arg
1               5                   10                  15

Ser Ser Ser Ser Ser Arg
            20

<210> SEQ ID NO 70
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 4H-4R/L-G)

<400> SEQUENCE: 70

Gly Arg Arg Gly Ser Gly Gly Arg Ser Ser Arg Gly Gly Arg
1               5                   10                  15

Gly Ser Gly Ser Gly Arg
            20

<210> SEQ ID NO 71
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 L-G/Q-G)

<400> SEQUENCE: 71

Gly Arg His Gly Ser Gly Gly Gly His Ser Ser His Gly Gly His
1               5                   10                  15

Gly Ser Gly Ser Gly Arg
```

20

<210> SEQ ID NO 72
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 L-G/Q-G/6S-6G)

<400> SEQUENCE: 72

Gly Arg His Gly Gly Gly Gly His Gly Gly Gly His Gly His
1               5                   10                  15

Gly Gly Gly Gly Gly Arg
            20

<210> SEQ ID NO 73
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 G+H)

<400> SEQUENCE: 73

Gly His His Gly Gly Gly Gly His Gly Gly Gly His Gly His
1               5                   10                  15

Gly Gly Gly Gly Gly His
            20

<210> SEQ ID NO 74
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 GR)

<400> SEQUENCE: 74

Gly Arg Arg Gly Gly Gly Gly Arg Gly Gly Gly Arg Gly Arg
1               5                   10                  15

Gly Gly Gly Gly Gly Arg
            20

<210> SEQ ID NO 75
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 HR)

<400> SEQUENCE: 75

Gly Arg Arg Gly Ser Gly Leu Gly Arg Ser Ser Ser Arg Gly Gln Arg
1               5                   10                  15

Gly Ser Gly Ser Gly Arg
            20

<210> SEQ ID NO 76
<211> LENGTH: 22
<212> TYPE: PRT
<213> ORGANISM: Artificial Sequence
<220> FEATURE:
<223> OTHER INFORMATION: Modified peptide derived from human hornerin
      (HR 1-18 G2656L)

```
<400> SEQUENCE: 76

Leu Arg His Gly Ser Gly Leu Gly His Ser Ser Ser His Gly Gln His
1               5                   10                  15

Gly Ser Gly Ser Gly Arg
            20

<210> SEQ ID NO 77
<211> LENGTH: 16
<212> TYPE: PRT
<213> ORGANISM: Artificial Sequence
<220> FEATURE:
<223> OTHER INFORMATION: Peptide derived from human hornerin (HR 1-25
      HRNR 2656-2671)

<400> SEQUENCE: 77

Gly Arg His Gly Ser Gly Leu Gly His Ser Ser Ser His Gly Gln His
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Peptide derived from human hornerin (HR 1-26
      HRNR 2657-2671)

<400> SEQUENCE: 78

Arg His Gly Ser Gly Leu Gly His Ser Ser Ser His Gly Gln His
1               5                   10                  15

<210> SEQ ID NO 79
<211> LENGTH: 12
<212> TYPE: PRT
<213> ORGANISM: Artificial Sequence
<220> FEATURE:
<223> OTHER INFORMATION: Peptide derived from human hornerin (HR 1-27
      HRNR 2657-2668)

<400> SEQUENCE: 79

Arg His Gly Ser Gly Leu Gly His Ser Ser Ser His
1               5                   10

<210> SEQ ID NO 80
<211> LENGTH: 29
<212> TYPE: PRT
<213> ORGANISM: Artificial Sequence
<220> FEATURE:
<223> OTHER INFORMATION: Peptide derived from human hornerin (HR 1-36
      HRNR 2663-2690)

<400> SEQUENCE: 80

Leu Gly His Ser Ser Ser His Gly Gln His Gly Ser Gly Ser Gly Arg
1               5                   10                  15

Ser Ser Ser Arg Gly Pro Tyr Glu Ser Arg Leu Gly His
            20                  25

<210> SEQ ID NO 81
<211> LENGTH: 13
<212> TYPE: PRT
<213> ORGANISM: Artificial Sequence
<220> FEATURE:
<223> OTHER INFORMATION: Peptide derived from human hornerin (HR 1-37
      HRNR 2656-2668)

<400> SEQUENCE: 81

Gly Arg His Gly Ser Gly Leu Gly His Ser Ser Ser His
```

```
<210> SEQ ID NO 82
<211> LENGTH: 14
<212> TYPE: PRT
<213> ORGANISM: Artificial Sequence
<220> FEATURE:
<223> OTHER INFORMATION: Peptide derived from human hornerin (HR 1-38
      HRNR 2664-2677)

<400> SEQUENCE: 82

His Ser Ser Ser His Gly Gln His Gly Ser Gly Ser Gly Arg
1               5                   10

<210> SEQ ID NO 83
<211> LENGTH: 19
<212> TYPE: PRT
<213> ORGANISM: Artificial Sequence
<220> FEATURE:
<223> OTHER INFORMATION: Peptide derived from human hornerin (HR 1-4
      HRNR 2619-2637)

<400> SEQUENCE: 83

His Gly Ser Ser Ser Gly Ser Ser Ser His Tyr Gly Gln His Gly Ser
1               5                   10                  15

Gly Ser Arg

<210> SEQ ID NO 84
<211> LENGTH: 20
<212> TYPE: PRT
<213> ORGANISM: Artificial Sequence
<220> FEATURE:
<223> OTHER INFORMATION: Peptide derived from human hornerin (HR 1-8
      HRNR2658-2677)

<400> SEQUENCE: 84

His Gly Ser Gly Leu Gly His Ser Ser Ser His Gly Gln His Gly Ser
1               5                   10                  15

Gly Ser Gly Arg
            20

<210> SEQ ID NO 85
<211> LENGTH: 26
<212> TYPE: PRT
<213> ORGANISM: Artificial Sequence
<220> FEATURE:
<223> OTHER INFORMATION: Peptide derived from human hornerin (HR 2-11
      HRNR 1132-1157)

<400> SEQUENCE: 85

Gly Ser Gly Ser Arg Gln Ser Pro Ser Tyr Gly Arg His Gly Ser Gly
1               5                   10                  15

Ser Gly Arg Ser Ser Ser Ser Gly Gln His
            20                  25

<210> SEQ ID NO 86
<211> LENGTH: 15
<212> TYPE: PRT
<213> ORGANISM: Artificial Sequence
<220> FEATURE:
<223> OTHER INFORMATION: Peptide derived from human hornerin (HR 2-14
      HRNR 1136-1150)

<400> SEQUENCE: 86

Arg Gln Ser Pro Ser Tyr Gly Arg His Gly Ser Gly Ser Gly Arg
1               5                   10                  15
```

<210> SEQ ID NO 87
<211> LENGTH: 14
<212> TYPE: PRT
<213> ORGANISM: Artificial Sequence
<220> FEATURE:
<223> OTHER INFORMATION: Modified peptide derived from human hornerin
      (HR 2-15 HRNR 1136-1150 S1148R)

<400> SEQUENCE: 87

Ser Arg Gln Ser Pro Ser Tyr Gly Arg His Gly Ser Gly Arg
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Modified peptide derived from human hornerin
      (HR 2-16 HRNR1128-1144)

<400> SEQUENCE: 88

His Ser Gln Arg Gly Ser Gly Ser Arg Gln Ser Pro Ser Tyr Gly Arg
1               5                   10                  15

His

<210> SEQ ID NO 89
<211> LENGTH: 19
<212> TYPE: PRT
<213> ORGANISM: Artificial Sequence
<220> FEATURE:
<223> OTHER INFORMATION: Modified peptide derived from human hornerin
      (HR 2-4H HRNR 1132-1150  Y1141H)

<400> SEQUENCE: 89

Gly Ser Gly Ser Arg Gln Ser Pro Ser His Gly Arg His Gly Ser Gly
1               5                   10                  15

Ser Gly Arg

<210> SEQ ID NO 90
<211> LENGTH: 19
<212> TYPE: PRT
<213> ORGANISM: Artificial Sequence
<220> FEATURE:
<223> OTHER INFORMATION: Modified peptide derived from human hornerin
      (HR 2-4L HRNR 1132-1150  P1139L)

<400> SEQUENCE: 90

Gly Ser Gly Ser Arg Gln Ser Leu Ser Tyr Gly Arg His Gly Ser Gly
1               5                   10                  15

Ser Gly Arg

<210> SEQ ID NO 91
<211> LENGTH: 19
<212> TYPE: PRT
<213> ORGANISM: Artificial Sequence
<220> FEATURE:
<223> OTHER INFORMATION: Modified peptide derived from human hornerin
      (HR 2-4Q HRNR 1132-1150  H1144Q)

<400> SEQUENCE: 91

Gly Ser Gly Ser Arg Gln Ser Pro Ser Tyr Gly Arg Gln Gly Ser Gly
1               5                   10                  15

Ser Gly Arg

<210> SEQ ID NO 92
<211> LENGTH: 19
<212> TYPE: PRT
<213> ORGANISM: Artificial Sequence
<220> FEATURE:
<223> OTHER INFORMATION: Modified peptide derived from human hornerin
      (HR 2-4R HRNR 1132-1150 Y1141R)

<400> SEQUENCE: 92

Gly Ser Gly Ser Arg Gln Ser Pro Ser Arg Gly Arg His Gly Ser Gly
1               5                   10                  15

Ser Gly Arg

<210> SEQ ID NO 93
<211> LENGTH: 19
<212> TYPE: PRT
<213> ORGANISM: Artificial Sequence
<220> FEATURE:
<223> OTHER INFORMATION: Modified peptide derived from human hornerin
      (HR 2-4S HRNR 1132-1150 P1139S)

<400> SEQUENCE: 93

Gly Ser Gly Ser Arg Gln Ser Ser Ser Tyr Gly Arg His Gly Ser Gly
1               5                   10                  15

Ser Gly Arg

<210> SEQ ID NO 94
<211> LENGTH: 12
<212> TYPE: PRT
<213> ORGANISM: Artificial Sequence
<220> FEATURE:
<223> OTHER INFORMATION: Peptide derived from human hornerin (HR 2-8)

<400> SEQUENCE: 94

Gly Ser Gly Ser Arg Gln Ser Pro Ser Tyr Gly Arg
1               5                   10

<210> SEQ ID NO 95
<211> LENGTH: 29
<212> TYPE: PRT
<213> ORGANISM: Artificial Sequence
<220> FEATURE:
<223> OTHER INFORMATION: Peptide derived from human hornerin (HRNR
      1013-1041)

<400> SEQUENCE: 95

Gly Arg His Gly Ser Gly Ser Gly Gln Ser Ser Ser Tyr Gly Pro Tyr
1               5                   10                  15

Arg Ser Gly Ser Gly Trp Ser Ser Ser Arg Gly Pro Tyr
            20                  25

<210> SEQ ID NO 96
<211> LENGTH: 29
<212> TYPE: PRT
<213> ORGANISM: Artificial Sequence
<220> FEATURE:
<223> OTHER INFORMATION: Peptide derived from human hornerin (HRNR
      1952-1980)

<400> SEQUENCE: 96

Gly Arg His Gly Ser Gly Ser Gly Gln Ser Ser Ser Tyr Gly Pro Tyr
1               5                   10                  15

Gly Ser Gly Ser Gly Trp Ser Ser Ser Arg Gly Pro Tyr
            20                  25

<210> SEQ ID NO 97
<211> LENGTH: 22
<212> TYPE: PRT
<213> ORGANISM: Artificial Sequence
<220> FEATURE:
<223> OTHER INFORMATION: Peptide derived from human hornerin (HRNR 2186-2207)

<400> SEQUENCE: 97

Gly Arg His Gly Ser Gly Ser Gly His Ser Ser His Gly Gln His
1               5                   10                  15

Gly Ser Gly Ser Gly Arg
            20

<210> SEQ ID NO 98
<211> LENGTH: 63
<212> TYPE: PRT
<213> ORGANISM: Artificial Sequence
<220> FEATURE:
<223> OTHER INFORMATION: Peptide derived from human hornerin (HRNR 232-294)

<400> SEQUENCE: 98

Ser Gln His Lys Ser Ser Ser Gly Gln Ser Ser Gly Tyr Ser Gln His
1               5                   10                  15

Gly Ser Gly Ser Gly His Ser Ser Gly Tyr Gly Gln His Gly Ser Arg
            20                  25                  30

Ser Gly Gln Ser Ser Arg Gly Asp Arg His Arg Ser Ser Ser Gly Ser
        35                  40                  45

Ser Ser Ser Tyr Gly Gln His Gly Ser Gly Ser Arg Gln Ser Leu
    50                  55                  60

<210> SEQ ID NO 99
<211> LENGTH: 26
<212> TYPE: PRT
<213> ORGANISM: Artificial Sequence
<220> FEATURE:
<223> OTHER INFORMATION: Peptide derived from human hornerin (HRNR 2422-2447)

<400> SEQUENCE: 99

Gly Arg His Gly Ser Gly Ser Gly Gln Ser Ser Ser Tyr Ser Pro Tyr
1               5                   10                  15

Gly Ser Gly Ser Gly Trp Ser Ser Ser Arg
            20                  25

<210> SEQ ID NO 100
<211> LENGTH: 29
<212> TYPE: PRT
<213> ORGANISM: Artificial Sequence
<220> FEATURE:
<223> OTHER INFORMATION: Peptide derived from human hornerin (HRNR 2422-2450)

<400> SEQUENCE: 100

Gly Arg His Gly Ser Gly Ser Gly Gln Ser Ser Ser Tyr Ser Pro Tyr
1               5                   10                  15

Gly Ser Gly Ser Gly Trp Ser Ser Ser Arg Gly Pro Tyr
            20                  25

<210> SEQ ID NO 101
<211> LENGTH: 67
<212> TYPE: PRT
<213> ORGANISM: Artificial Sequence

```
<220> FEATURE:
<223> OTHER INFORMATION: Peptide derived from human hornerin (HRNR
      295-361)

<400> SEQUENCE: 101

Gly His Gly Arg Gln Gly Ser Gly Ser Arg Gln Ser Pro Ser His Val
1               5                   10                  15

Arg His Gly Ser Gly Ser Gly His Ser Ser His Gly Gln His Gly
            20                  25                  30

Ser Gly Ser Ser Tyr Ser Tyr Ser Arg Gly His Tyr Glu Ser Gly Ser
        35                  40                  45

Gly Gln Thr Ser Gly Phe Gly Gln His Glu Ser Gly Ser Gly Gln Ser
    50                  55                  60

Ser Gly Tyr
65

<210> SEQ ID NO 102
<211> LENGTH: 62
<212> TYPE: PRT
<213> ORGANISM: Artificial Sequence
<220> FEATURE:
<223> OTHER INFORMATION: Peptide derived from human hornerin (HRNR
      933-994)

<400> SEQUENCE: 102

Gly His Lys Ser Ser Gly Gln Ser Ser Gly Tyr Thr Gln His Gly
1               5                   10                  15

Ser Gly Ser Gly His Ser Ser Ser Tyr Glu Gln His Gly Ser Arg Ser
            20                  25                  30

Gly Gln Ser Ser Arg Ser Glu Gln His Gly Ser Ser Ser Gly Ser Ser
        35                  40                  45

Ser Ser Tyr Gly Gln His Gly Ser Gly Ser Arg Gln Ser Leu
    50                  55                  60

<210> SEQ ID NO 103
<211> LENGTH: 62
<212> TYPE: PRT
<213> ORGANISM: Artificial Sequence
<220> FEATURE:
<223> OTHER INFORMATION: Peptide derived from human hornerin (HRNR
      995-1056)

<400> SEQUENCE: 103

Leu Gly His Gly Gln His Gly Ser Gly Ser Gly Gln Ser Pro Ser Pro
1               5                   10                  15

Ser Arg Gly Arg His Gly Ser Gly Ser Gly Gln Ser Ser Tyr Gly
            20                  25                  30

Pro Tyr Arg Ser Gly Ser Gly Trp Ser Ser Ser Arg Gly Pro Tyr Glu
        35                  40                  45

Ser Gly Ser Gly His Ser Ser Gly Leu Gly His Arg Glu Arg
    50                  55                  60

<210> SEQ ID NO 104
<211> LENGTH: 13
<212> TYPE: PRT
<213> ORGANISM: Artificial Sequence
<220> FEATURE:
<223> OTHER INFORMATION: Synthetic cationic intrinsically disordered
      antimicrobial peptide (K-GR13)

<400> SEQUENCE: 104

Gly Lys Lys Gly Gly Lys Gly Gly Lys Gly Lys Gly Lys
```

<210> SEQ ID NO 105
<211> LENGTH: 11
<212> TYPE: PRT
<213> ORGANISM: Artificial Sequence
<220> FEATURE:
<223> OTHER INFORMATION: Peptide derived from human late cornified
      envelope protein 1B (LCE1B 78-88)

<400> SEQUENCE: 105

Ser His His Arg Arg Arg Arg Ser His Cys His
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Peptide derived from human late cornified
      envelope protein 2A (LCE2A 70-82)

<400> SEQUENCE: 106

Ser His His Arg Pro Arg Leu Phe His Arg His Arg His
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Peptide derived from human late cornified
      envelope protein 2B (LCE2B 74-86)

<400> SEQUENCE: 107

Ser His His Arg Pro Arg Leu Phe His Arg Arg Arg His
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Peptide derived from human late cornified
      envelope protein 3A (LCE3A 50-60)

<400> SEQUENCE: 108

Ser His His Arg Cys Arg Arg Ser His Arg Cys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Peptide derived from human late cornified
      envelope protein 3C (LCE3C 55-66)

<400> SEQUENCE: 109

Ser His His Arg His Phe Arg Ser His Gln Cys Arg
1               5                   10

<210> SEQ ID NO 110
<211> LENGTH: 21
<212> TYPE: PRT
<213> ORGANISM: Artificial Sequence
<220> FEATURE:
<223> OTHER INFORMATION: Peptide derived from human late cornified envelope protein 3C (LCE3C 55-75)

<400> SEQUENCE: 110

Ser His His Arg His Phe Arg Ser His Gln Cys Arg Arg Gln Arg Ser
1               5                   10                  15

Asn Ser Cys Asp Arg
            20

<210> SEQ ID NO 111
<211> LENGTH: 10
<212> TYPE: PRT
<213> ORGANISM: Artificial Sequence
<220> FEATURE:
<223> OTHER INFORMATION: Peptide derived from human late cornified
      envelope protein 3D (LCE3D 55-64)

<400> SEQUENCE: 111

Asn His His Arg Arg His His Arg Cys Arg
1               5                   10

<210> SEQ ID NO 112
<211> LENGTH: 22
<212> TYPE: PRT
<213> ORGANISM: Artificial Sequence
<220> FEATURE:
<223> OTHER INFORMATION: Myristoylated peptide derived from human
      hornerin (Myr-HR 1-18)
<220> FEATURE:
<221> NAME/KEY: LIPID
<222> LOCATION: (1)..(1)
<223> OTHER INFORMATION: MYRISTATE

<400> SEQUENCE: 112

Gly Arg His Gly Ser Gly Leu Gly His Ser Ser Ser His Gly Gln His
1               5                   10                  15

Gly Ser Gly Ser Gly Arg
            20

<210> SEQ ID NO 113
<211> LENGTH: 22
<212> TYPE: PRT
<213> ORGANISM: Artificial Sequence
<220> FEATURE:
<223> OTHER INFORMATION: Myristoylated modified peptide derived from
      human hornerin (Myr-HR 1-18 HR)
<220> FEATURE:
<221> NAME/KEY: LIPID
<222> LOCATION: (1)..(1)
<223> OTHER INFORMATION: MYRISTATE

<400> SEQUENCE: 113

Gly Arg Arg Gly Ser Gly Leu Gly Arg Ser Ser Ser Arg Gly Gln Arg
1               5                   10                  15

Gly Ser Gly Ser Gly Arg
            20

<210> SEQ ID NO 114
<211> LENGTH: 13
<212> TYPE: PRT
<213> ORGANISM: Artificial Sequence
<220> FEATURE:
<223> OTHER INFORMATION: Synthetic cationic intrinsically disordered
      antimicrobial peptide (Orn-GR13)
<220> FEATURE:
<221> NAME/KEY: MOD_RES
<222> LOCATION: (2)..(3)
<223> OTHER INFORMATION: Orn
<220> FEATURE:

```
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (13)..(13)
<223> OTHER INFORMATION: Orn

<400> SEQUENCE: 114

Gly Xaa Xaa Gly Gly Xaa Gly Gly Xaa Gly Xaa Gly Xaa
1               5                   10

<210> SEQ ID NO 115
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GK4)
<220> FEATURE:
<221> NAME/KEY: LIPID
<222> LOCATION: (1)..(1)
<223> OTHER INFORMATION: PALMITATE

<400> SEQUENCE: 115

Gly Lys Gly Lys
1

<210> SEQ ID NO 116
<211> LENGTH: 4
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-GOrn4)
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 116

Gly Xaa Gly Xaa
1

<210> SEQ ID NO 117
<211> LENGTH: 22
<212> TYPE: PRT
<213> ORGANISM: Artificial Sequence
<220> FEATURE:
<223> OTHER INFORMATION: Palmitoylated modified peptide derived from
      human hornerin (Pal-HR 1-18 4H-4R)
<220> FEATURE:
<221> NAME/KEY: LIPID
<222> LOCATION: (1)..(1)
<223> OTHER INFORMATION: PALMITATE

<400> SEQUENCE: 117
```

```
Gly Arg Arg Gly Ser Gly Leu Gly Arg Ser Ser Arg Gly Gly Arg
1               5                   10                  15

Gly Ser Gly Ser Gly Arg
                20

<210> SEQ ID NO 118
<211> LENGTH: 13
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-K-GR13)
<220> FEATURE:
<221> NAME/KEY: LIPID
<222> LOCATION: (1)..(1)
<223> OTHER INFORMATION: PALMITATE

<400> SEQUENCE: 118

Gly Lys Lys Gly Gly Lys Gly Gly Lys Gly Lys Gly Lys
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Palmitoylated peptide derived from human late
      cornified envelope protein 3B (Pal-LCE3B)
<220> FEATURE:
<221> NAME/KEY: LIPID
<222> LOCATION: (1)..(1)
<223> OTHER INFORMATION: PALMITATE

<400> SEQUENCE: 119

Ser His His Arg Pro Arg Leu Phe His Arg Arg Arg His
1               5                   10

<210> SEQ ID NO 120
<211> LENGTH: 21
<212> TYPE: PRT
<213> ORGANISM: Artificial Sequence
<220> FEATURE:
<223> OTHER INFORMATION: Palmitoylated peptide derived from human late
      cornified envelope protein 3C (Pal-LCE3C 55-75)
<220> FEATURE:
<221> NAME/KEY: LIPID
<222> LOCATION: (1)..(1)
<223> OTHER INFORMATION: PALMITATE

<400> SEQUENCE: 120

Ser His His Arg His Phe Arg Ser His Gln Cys Arg Arg Gln Arg Ser
1               5                   10                  15

Asn Ser Cys Asp Arg
                20

<210> SEQ ID NO 121
<211> LENGTH: 13
<212> TYPE: PRT
<213> ORGANISM: Artificial Sequence
<220> FEATURE:
<223> OTHER INFORMATION: Palmitoylated synthetic cationic intrinsically
      disordered antimicrobial peptide (Pal-Orn-GR13)
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (2)..(3)
```

```
<223> OTHER INFORMATION: Orn
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (13)..(13)
<223> OTHER INFORMATION: Orn

<400> SEQUENCE: 121

Gly Xaa Xaa Gly Gly Xaa Gly Gly Xaa Gly Xaa Gly Xaa
1               5                   10

<210> SEQ ID NO 122
<211> LENGTH: 22
<212> TYPE: PRT
<213> ORGANISM: Artificial Sequence
<220> FEATURE:
<223> OTHER INFORMATION: Peptide with reverse sequence to 18 amino acid
      peptide derived from human hornerin (revHR 1-18)

<400> SEQUENCE: 122

Arg Gly Ser Gly Ser Gly His Gln Gly His Ser Ser Ser His Gly Leu
1               5                   10                  15

Gly Ser Gly His Arg Gly
            20

<210> SEQ ID NO 123
<211> LENGTH: 24
<212> TYPE: PRT
<213> ORGANISM: Artificial Sequence
<220> FEATURE:
<223> OTHER INFORMATION: Peptide derived from human repetin (RPTN
      747-770)

<400> SEQUENCE: 123

Thr His Glu His Glu Gln Ser His Gln Arg Arg Asp Arg Gln Thr His
1               5                   10                  15

Glu Asp Lys Gln Asn Arg Gln Arg
            20

<210> SEQ ID NO 124
<211> LENGTH: 22
<212> TYPE: PRT
<213> ORGANISM: Artificial Sequence
<220> FEATURE:
<223> OTHER INFORMATION: Peptide with scrambled amino acid sequence of a
      18 amino acid peptide derived from human hornerin (scrHR 1-18)

<400> SEQUENCE: 124

Ser Leu Ser Ser Gly His Gly Ser Gly His Gly His Gln Arg Gly Gly
1               5                   10                  15

His Arg Ser Gly Ser Gly
            20

<210> SEQ ID NO 125
<211> LENGTH: 30
<212> TYPE: PRT
<213> ORGANISM: Artificial Sequence
```

```
<220> FEATURE:
<223> OTHER INFORMATION: S-palmitoylated peptide derived from human
      hornerin (S-Pal-HRNR 1089-1117)
<220> FEATURE:
<221> NAME/KEY: LIPID
<222> LOCATION: (1)..(1)
<223> OTHER INFORMATION: PALMITATE (THIOETHER BOND)

<400> SEQUENCE: 125

Cys Gly Gln His Gly Ala Thr Ser Ser Gly Gln Ser Ser Ser His Gly
1               5                   10                  15

Gln His Gly Ser Gly Ser Ser Gln Ser Ser Gly Tyr Gly Arg
            20                  25                  30

<210> SEQ ID NO 126
<211> LENGTH: 26
<212> TYPE: PRT
<213> ORGANISM: Artificial Sequence
<220> FEATURE:
<223> OTHER INFORMATION: S-palmitoylated peptide derived from human
      hornerin (S-Pal-HRNR 1389-1414)
<220> FEATURE:
<221> NAME/KEY: LIPID
<222> LOCATION: (26)..(26)
<223> OTHER INFORMATION: PALMITATE (THIOETHER BOND)

<400> SEQUENCE: 126

Gly Arg His Gly Ser Gly Ser Gly Gln Ser Ser Gly Phe Gly His His
1               5                   10                  15

Glu Ser Ser Ser Trp Gln Ser Ser Gly Cys
            20                  25

<210> SEQ ID NO 127
<211> LENGTH: 31
<212> TYPE: PRT
<213> ORGANISM: Artificial Sequence
<220> FEATURE:
<223> OTHER INFORMATION: S-palmitoylated peptide derived from human
      hornerin (S-Pal-HRNR 1748-1778)
<220> FEATURE:
<221> NAME/KEY: LIPID
<222> LOCATION: (31)..(31)
<223> OTHER INFORMATION: PALMITATE (THIOETHER BOND)

<400> SEQUENCE: 127

Ser Gly His Ser Ser Val Phe Gly Gln His Glu Ser Gly Ser Gly His
1               5                   10                  15

Ser Ser Ala Tyr Ser Gln His Gly Ser Gly Ser Gly His Phe Cys
            20                  25                  30

<210> SEQ ID NO 128
<211> LENGTH: 26
<212> TYPE: PRT
<213> ORGANISM: Artificial Sequence
<220> FEATURE:
<223> OTHER INFORMATION: S-palmitoylated peptide derived from human
      hornerin (S-Pal-HRNR 598-623)
<220> FEATURE:
<221> NAME/KEY: LIPID
<222> LOCATION: (26)..(26)
<223> OTHER INFORMATION: PALMITATE (THIOETHER BOND)

<400> SEQUENCE: 128

Gly Gln His Gly Ser Ser Ser Gly His Ser Ser Thr His Gly Gln His
1               5                   10                  15

Gly Ser Thr Ser Gly Gln Ser Ser Ser Cys
            20                  25
```

```
<210> SEQ ID NO 129
<211> LENGTH: 26
<212> TYPE: PRT
<213> ORGANISM: Artificial Sequence
<220> FEATURE:
<223> OTHER INFORMATION: S-palmitoylated peptide derived from human
      hornerin (S-Pal-HRNR 623-648)
<220> FEATURE:
<221> NAME/KEY: LIPID
<222> LOCATION: (1)..(1)
<223> OTHER INFORMATION: PALMITATE (THIOETHER BOND)

<400> SEQUENCE: 129

Cys Gly Gln His Gly Ala Thr Ser Gly Gln Ser Ser Ser His Gly Gln
1               5                   10                  15

His Gly Ser Gly Ser Ser Gln Ser Ser Arg
            20                  25

<210> SEQ ID NO 130
<211> LENGTH: 26
<212> TYPE: PRT
<213> ORGANISM: Artificial Sequence
<220> FEATURE:
<223> OTHER INFORMATION: S-palmitoylated peptide derived from human
      hornerin (S-Pal-HRNR 2004-2029)
<220> FEATURE:
<221> NAME/KEY: LIPID
<222> LOCATION: (26)..(26)
<223> OTHER INFORMATION: PALMITATE (THIOETHER BOND)

<400> SEQUENCE: 130

Gly Gln His Gly Ser Ser Ser Gly His Ser Thr His Gly Gln His
1               5                   10                  15

Gly Ser Ala Ser Gly Gln Ser Ser Ser Cys
            20                  25

<210> SEQ ID NO 131
<211> LENGTH: 20
<212> TYPE: PRT
<213> ORGANISM: Artificial Sequence
<220> FEATURE:
<223> OTHER INFORMATION: Synthetic

<400> SEQUENCE: 131

His Gly Ser Arg Ser Gly Gln Ser Ser Arg Gly Glu Arg His Gly Ser
1               5                   10                  15

Ser Ser Gly Ser
            20

<210> SEQ ID NO 132
<211> LENGTH: 25
<212> TYPE: PRT
<213> ORGANISM: Artificial Sequence
<220> FEATURE:
<223> OTHER INFORMATION: Synthetic

<400> SEQUENCE: 132

Gly Ser Gly Ser Arg Gln Ser Ser Gly His Gly Arg Gln Gly Ser Gly
1               5                   10                  15

Ser Gly Gln Ser Pro Ser Arg Gly Arg
            20                  25

<210> SEQ ID NO 133
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 133

His Gly Ser Gly Leu Gly His
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

His Gly Gln His Gly Ser Gly Ser Gly Arg
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Arg His Gly Ser Gly Leu Gly His
1               5
```